US011000578B2

(12) United States Patent
McNeel et al.

(10) Patent No.: US 11,000,578 B2
(45) Date of Patent: May 11, 2021

(54) TREATMENT OF PROSTATE CANCER WITH PAP VACCINE AND PD-1 INHIBITOR CO-THERAPY

(71) Applicant: Madison Vaccines Inc., Madison, WI (US)

(72) Inventors: Doug McNeel, Madison, WI (US); Richard Lesniewski, Madison, WI (US)

(73) Assignee: Madison Vaccines Inc., Madison, WI (US)

( * ) Notice: Subject to any disclaimer, the term of this patent is extended or adjusted under 35 U.S.C. 154(b) by 0 days.

(21) Appl. No.: 15/430,012

(22) Filed: Feb. 10, 2017

(65) Prior Publication Data

US 2017/0182139 A1 Jun. 29, 2017

Related U.S. Application Data

(60) Provisional application No. 62/404,252, filed on Oct. 15, 2016, provisional application No. 62/294,349, filed on Feb. 12, 2016.

(51) Int. Cl.
| | |
|---|---|
| *A61K 39/00* | (2006.01) |
| *C07K 16/28* | (2006.01) |
| *A61P 35/04* | (2006.01) |
| *A61P 35/00* | (2006.01) |
| *A61K 39/395* | (2006.01) |
| *C07K 16/30* | (2006.01) |

(52) U.S. Cl.
CPC .. *A61K 39/001193* (2018.08); *A61K 39/0011* (2013.01); *A61K 39/001163* (2018.08); *A61K 39/3955* (2013.01); *A61P 35/00* (2018.01); *A61P 35/04* (2018.01); *C07K 16/2818* (2013.01); *A61K 2039/505* (2013.01); *A61K 2039/53* (2013.01); *A61K 2039/545* (2013.01); *A61K 2039/55516* (2013.01); *A61K 2039/884* (2018.08); *C07K 16/3069* (2013.01); *C07K 2317/24* (2013.01); *C07K 2317/76* (2013.01)

(58) Field of Classification Search
CPC .... A61K 39/001193; A61K 39/001163; A61K 39/3955; A61K 39/0011; A61K 2039/884; A61K 2039/55516; A61K 2039/505; A61K 2039/53; A61K 2039/545; A61P 35/04; A61P 35/00; C07K 16/2818; C07K 16/3069; C07K 2317/24; C07K 2317/76
See application file for complete search history.

(56) References Cited

U.S. PATENT DOCUMENTS

| | | | |
|---|---|---|---|
| 8,962,590 B2 | 2/2015 | McNeel et al. | |
| 9,339,538 B2 | 5/2016 | McNeel et al. | |
| 9,433,668 B2 | 9/2016 | McNeel et al. | |
| 2002/0183251 A1 | 12/2002 | Xu et al. | |
| 2004/0142890 A1* | 7/2004 | McNeel | A61K 39/0011 514/44 R |
| 2007/0123487 A1 | 5/2007 | McNeel | |
| 2007/0232558 A1 | 10/2007 | McNeel et al. | |
| 2008/0063654 A1 | 3/2008 | McNeel et al. | |
| 2008/0206289 A1 | 8/2008 | McNeel et al. | |
| 2009/0304711 A1 | 12/2009 | Pardoll et al. | |
| 2010/0092523 A1 | 4/2010 | Disis et al. | |
| 2010/0124755 A1 | 5/2010 | McNeel et al. | |
| 2011/0301052 A1 | 12/2011 | McNeel et al. | |
| 2012/0020912 A1 | 1/2012 | McNeel et al. | |
| 2012/0177581 A1 | 7/2012 | McNeel et al. | |
| 2014/0105853 A1 | 4/2014 | McNeel et al. | |
| 2014/0161818 A1 | 6/2014 | McNeel et al. | |
| 2015/0210769 A1 | 7/2015 | Freeman et al. | |
| 2015/0306197 A1 | 10/2015 | McNeel et al. | |
| 2016/0129098 A1 | 5/2016 | McNeel et al. | |
| 2016/0166686 A1 | 6/2016 | McNeel et al. | |
| 2016/0238606 A1 | 8/2016 | McNeel et al. | |
| 2016/0263218 A1 | 9/2016 | McNeel et al. | |
| 2017/0014498 A1 | 1/2017 | McNeel et al. | |

FOREIGN PATENT DOCUMENTS

| | | |
|---|---|---|
| WO | WO 01/25272 A2 * | 4/2001 |
| WO | 2015/103602 | 7/2015 |
| WO | 2017/139755 | 8/2017 |

OTHER PUBLICATIONS

Muniyan et al. Human prostatic acid phosphatase: structure, function and regulation. Int J Mol Sci. 14(5): 10438-10464, published online May 21, 2013.*
Iams et al. My Cancer Genome, pp. 1-5, Nov. 24, 2015.*
Lee et al. Table 1 within Transl Lung Cancer Res. Dec. 2014; 3(6): 408-410.*
University of Wisconsin, School of Medicine and Public Health. 1 page, published Aug. 19, 2015.*
ClinicalTrials.gov Vaccine therapy and pembrolizumab in treating patients with hormone-resistant, metastatic prostate cancer. 13 pages. Posted Jul. 16, 2015.*
International Search Report, International Patent Application No. PCT/US2017/017445, dated Jun. 6, 2017, six pages.
Hammerstrom et al. "Cancer Immunotherapy: Sipuleucel-T and Beyond" Pharamcotherapy. Aug. 2011; 31(8): 813-828.
European Search Report, EP Patent Application No. 17750860.3, dated Oct. 25, 2019, 11 pages.
Plieth, Jacob "PD-1/PDL1 Combination therapies" Evaluate, Nov. 2015, 18 pages.
Rekoske, B. et al. Abstract CN04-03: DNA vaccines as treatment for prostate cancer—understanding mechanisms of resistance, Molecular Cancer Therapeutics, Nov. 2015, 4 pages.

(Continued)

*Primary Examiner* — Alana Harris Dent
(74) *Attorney, Agent, or Firm* — Casimir Jones S.C.; J. Mitchell Jones

(57) ABSTRACT

Provided herein is technology relating to cancer treatment and prevention and particularly, but not exclusively, to compositions and methods related to therapies for prostate cancer.

16 Claims, 6 Drawing Sheets

Specification includes a Sequence Listing.

(56) References Cited

OTHER PUBLICATIONS

Alam, S. and McNeel, D. G. (2010). "DNA vaccines for the treatment of prostate cancer." Expert Rev Vaccines 9: 731-45.
Boikos and Antonarakis "Immunotherapy for Prostate Cancer Enters Its Golden Age", Clin Med Insights Oncol. 2012;6:263-73.
Bot et al. "Programmed cell death-1 (PD-1) at the heart of heterologous prime-boost vaccines and regulation of CD8+ T cell immunit"y, J Transl Med. 2010; 8: 132.
Cha and Fong "Immunotherapy for Prostate Cancer: Biology and Therapeutic Approaches", J Clin Oncol. Sep. 20, 2011;29(27):3677-85.
Le DT, Uram JN, Wang H, et al. "PD-1 Blockade in Tumors with Mismatch-Repair Deficiency". N. Engl J Med. Jun. 25, 2015;372(26):2509-2520.
McNeel et al. "DNA Vaccines for Prostate Cancer" Curr Cancer Ther Rev. Nov. 1, 2012, 8(4):254-263.
McNeel, D. G. (2007). "Cellular immunotherapies for prostate cancer." Biomed Pharmacother 61: 315-22.
McNeel, D. G. (2007). "Prostate cancer immunotherapy." Curr Opin Urol 17: 175-81.
McNeel, D. G., et al. (2014). "Real-time immune monitoring to guide plasmid DNA vaccination schedule targeting prostatic acid phosphatase in patients with castration-resistant prostate cancer." Clin Cancer Res 20: 3692-704.
McNeel, D. G., et al. (2001). "Naturally occurring prostate cancer antigen-specific T cell responses of a Th1 phenotype can be detected in patients with prostate cancer." Prostate 47: 222-9.
McNeel, D. G., et al. (2000). "Antibody immunity to prostate cancer-associated antigens can be detected in the serum of patients with prostate cancer." J. Urol. 164: 1825-9.
Olson, B. M. and McNeel, D. G. (2011). "Sipuleucel-T: immunotherapy for advanced prostate cancer." Open Acc. J. Urol. 3: 49-60.
Rekoske BT, et al. "Antitumor vaccination of prostate cancer patients elicits PD-1/PD-L1 regulated antigen-specific immune responses". Oncoimmunology. Jun. 2016;5(6):e1165377.
Rekoske BT, et al. "PD-1 or PD-L1 Blockade Restores Antitumor Efficacy Following SSX2 Epitope-Modified DNA Vaccine Immunization. Cancer immunology research." Aug. 2015;3(8):946-955.
Smith, H. A., et al. (2014). "DNA vaccines encoding altered peptide ligands for SSX2 enhance epitope-specific CD8+ T-cell immune responses." Vaccine 32: 1707-15.
Vanneman and Dranoff "Combining Immunotherapy and Targeted Therapies in Cancer Treatment" Nat Rev Cancer, 2014, 12(4): 237-251.
Ward, J. E and McNeel, D. G. (2007). "GVAX: an allogeneic, whole-cell, GM-CSF-secreting cellular immunotherapy for the treatment of prostate cancer." Expert Opin Biol Ther 7: 1893-902.
Westdorp et al. Immunotherapy for Prostate Cancer: Lessons from Responses to Tumor-Associated Antigens, Front Immunol. 2014; 5: 191.

\* cited by examiner

TREATMENT OF PROSTATE CANCER WITH PAP VACCINE AND PD-1 INHIBITOR CO-THERAPY

CROSS-REFERENCE TO RELATED APPLICATIONS

This application claims the benefit of U.S. Prov. Appl. 62/294,349, filed Feb. 12, 2016, and U.S. Prov. Appl. 62/404,252, filed Oct. 5, 2016, each of which is incorporated herein by reference in its entirety.

STATEMENT REGARDING FEDERALLY SPONSORED RESEARCH OR DEVELOPMENT

This invention was made with government support under Grant No. W81XWH-08-1-0341 awarded by the Department of Defense and Grant No. CA 142608 awarded by the National Institutes of Health. The government has certain rights in the invention.

FIELD

Provided herein is technology relating to cancer treatment and prevention and particularly, but not exclusively, to compositions and methods related to therapies for prostate cancer.

BACKGROUND

Prostate cancer is the most common tumor among men, and the second leading cause of male cancer-related death in the United States [1]. Despite advances in screening and early detection, over 30,000 U.S. men are estimated to die as a result of prostate cancer in 2014 [1]. Treatment with surgery and radiation remain effective for presumed organ-confined disease, however approximately one third of these patients will have progressive or metastatic disease at 10 years [2]. Prostate cancer, once it becomes metastatic, is not curable and is generally initially treated with androgen deprivation, and androgen deprivation remains the cornerstone on which other therapies are added [3]. Unfortunately, within typically 2-3 years the disease becomes refractory to androgen deprivation, and castrate-resistant prostate cancer is the lethal phenotype of the disease. Within the last several years, several therapies have been approved by FDA based on their ability to prolong overall survival in this population of patients. Specifically, docetaxel was approved in 2004 after two large randomized trials showed a 2-3 month median improvement in overall survival compared with mitoxantrone [4, 5]. Cabazitaxel was approved in 2010 for patients with disease refractory to docetaxel after an international trial demonstrated a similar 2-3 month median improvement in overall survival compared with mitoxantrone [6]. Also in 2010, sipuleucel-T (Provenge®, Dendreon Corporation) was approved for patients with minimally symptomatic castrate-resistant, metastatic prostate cancer based on the results of a prospectively randomized, blinded, phase III placebo-controlled clinical trial and supporting data from previous phase III clinical trials demonstrating a median 4-month improvement in overall survival [7]. Finally, in 2011 and 2013, abiraterone and enzalutamide, agents targeting androgen synthesis or signaling, were similarly approved in the setting of docetaxel-refractory, castrate-resistant metastatic prostate cancer following a prospectively randomized, blinded, placebo-controlled trial demonstrating a 2-3-month median improvement in overall survival [8, 9]. These recent advances have clearly improved the situation for patients with advanced prostate cancer; however, the recent advances have also presented new challenges in terms of the optimal sequence and approach to the management of castrate-resistant disease. Despite the impact of chemotherapies for advanced prostate cancer, many patients and treating physicians believe that the small overall survival benefit provided by chemotherapy may not justify its use in all patients, in part due to potential side effects [10]. Thus, new and improved prostate cancer treatments are needed.

SUMMARY

Vaccine-based strategies, also known as active immunotherapies, provide improved treatments. For example, the trials that led to the approval of sipuleucel-T showed fewer adverse events than are typically seen with chemotherapy agents [7]. Many vaccines for prostate cancer are in clinical development, all of which have demonstrated similar safety profiles, and some of which have demonstrated anti-tumor activity [11, 12, 13, 14]. There has also been interest in developing antigen non-specific immune-activating therapies, such as those with activities associated with T-cell checkpoint blockade. Inhibitors of PD/PD-L1 or CTLA-4, for example, have demonstrated remarkable efficacy alone or in combination for metastatic melanoma [15, 16, 17], and PD/PD-L blockade inhibitors have demonstrated activity as single agents for several solid tumor types [18, 19]. Targeting PD-1, in particular, should be a universal therapy, as it targets the T-cell compartment rather than the tumor directly. However, in separate phase I trials with PD-1 blocking antibodies, there has been no objective response observed in patients (n=25) with metastatic prostate cancer [18, 19]. The difference in response to certain tumors, with higher frequencies of responses observed in patients with renal cell cancer, melanoma, and non-small cell lung cancer compared to prostate cancer, for example, suggest that differences are likely due to differences in the T-cells of responding and non-responding patients. In addition, early phase clinical trials using PD-1 or PD-L1 have identified that the expression of at least one of the ligands for PD-1 (PD-L1) on the target tumor cell by biopsy is associated with clinical response to therapy [18]. This is expected, given that tissue-infiltrating T cells can induce the expression of PD-L1 via the expression of IFNγ. Notwithstanding, some tumors that are known to express PD-L1, such as prostate cancer [20], have demonstrated little response to treatment with PD-1 blockade as single-agent therapies [18, 19].

During experiments testing a vaccine targeting a tumor antigen in a murine model, data were collected indicating that immunization with a DNA vaccine encoding synovial sarcoma X breakpoint 2 (SSX2) leads to the generation of CD8+ T cells having cytolytic activity and expressing PD-1. Moreover, immunization leads to a compensatory response in the tumor to increase expression of PD-L1. In further studies, efforts to increase the number and avidity of CD8+ T cells with cytolytic activity by means of changes introduced into the DNA vaccine led to an unanticipated inferior anti-tumor immune response due to this PD-1/PD-L1 upregulation. Blockade of this pathway using antibodies blocking either PD-1 or PD-L1 restored the anti-tumor activity of the vaccine encoding the tumor-specific target antigen in this murine model, an effect not observed with anti-PD-1 treatment alone, as monotherapy had no demonstrable effect. Importantly, immunization with the vaccine encoding the native (unmodified) antigen in combination with an antibody blocking PD-1 similarly demonstrated an improved anti-tumor response compared to vaccination alone (see, e.g., Rekoske et al. (2015) "PD-1 or PD-L1 Blockade Restores Antitumor Efficacy Following SSX2 Epitope-Modified DNA Vaccine Immunization", *Cancer Immunol Res* 3: 946-55). As a result, active immunotherapies administered in combination with PD-1 checkpoint inhibitors provide further improvements for the efficacy of therapies and may have durable, objective anti-tumor responses in patients with metastatic cancer [21].

Prostatic acid phosphatase (PAP) is a model antigen for vaccine-based treatment strategies targeting prostate cancer. PAP is a well-defined protein whose expression is essentially restricted to normal and malignant prostate tissue [22]. It is also one of only a few known prostate-specific proteins for which there is a rodent homologue, thereby providing an animal model for evaluating vaccine strategies and assessing toxicity [23]. Data from independent labs have demonstrated that, in a rat model, vaccine strategies targeting PAP can result in PAP-specific CD8+ T-cells, the presumed population mediating tumor cell destruction, and anti-tumor responses [24, 25, 26, 27]. PAP is the target antigen of the autologous antigen-presenting cell sipuleucel-T vaccine in which autologous peripheral blood mononuclear cells are loaded ex vivo with a PAP-GM-CSF fusion protein. A separate phase I clinical trial evaluated dendritic cells loaded with a murine homologue of PAP, and demonstrated immunogenicity of this approach [28]. In rodent studies, experiments indicated that PAP can be immunologically targeted using genetic vaccines, such as a plasmid DNA vaccine in particular [25, 26]. Results have been reported of a phase I/II trial conducted in patients with early, PSA-recurrent (clinical stage D0) prostate cancer using this same DNA vaccine (pTVG-HP). No significant adverse events were observed in 22 subjects treated over a 12-week period of time. Moreover, several patients developed evidence of PAP-specific CD4+ and CD8+ T-cells, and several patients experienced a prolongation in the PSA doubling time, demonstrating immunological efficacy and suggesting a possible anti-tumor effect [29]. The presence of long-term IFNγ-secreting immune responses to PAP, detectable at multiple times throughout a period of months after immunization, were associated with increases in PSA doubling time, suggesting this might serve as a rational biomarker for efficacy [30]. Moreover, it was found that immune responses could be augmented months later with repeated immunizations, suggesting that DNA vaccines might provide a simple means of eliciting tumor-specific CD8+ T cells [31]. Finally, further studies indicated that patients previously treated with pTVG-HP have circulating PAP-specific CD8+ T cells with PD-1 expression and circulating EpCam+ circulating epithelial cells (CEC) with increased PD-L1 expression, analogous to findings in murine models.

Accordingly, these findings indicate that the pTVG-HP vaccine specifically elicits CD8+ T cells specific for prostate tumors and, further, that the efficacy of the pTVG-HP vaccine might be augmented by treatment with a PD-1 and/or PD-L1 inhibitor.

Thus, the technology provided herein provides a cancer therapy in which patients are treated with the DNA vaccine either together with (e.g., concurrently), or in sequence with, a PD-1 pathway inhibitor (e.g., pembrolizumab or nivolumab) or PD-L1 inhibitor, which produces a clinical response in the patient, such as, e.g., an objective disease response, a decline in serum PSA, and/or a prolonged time to disease progression. In some embodiments, the subjects have castration-resistant metastatic prostate cancer.

Further, it is contemplated that the technology comprises vaccines to other antigens for the treatment of prostate cancer. For instance, in some embodiments, a cancer therapy is provided in which patients are treated with the DNA vaccine either together with (e.g., concurrently), or in sequence with, an inhibitor of cytotoxic T-lymphocyte-associated protein 4 ("CTLA-4"; also known as CD152 (cluster of differentiation 152), e.g., a CTLA-4 inhibitor or CTLA-4 pathway inhibitor (e.g., an anti-CTLA-4 antibody (e.g., an anti-CTLA-4 monoclonal antibody)). Some embodiments comprise treatment with the DNA vaccine either together with (e.g., concurrently), or in sequence with, both a CTLA-4 inhibitor or CTLA-4 pathway inhibitor and a PD-1 inhibitor or PD-1 pathway inhibitor. Some embodiments comprise treatment with the DNA vaccine either together with (e.g., concurrently), or in sequence with, both a CTLA-4 inhibitor or CTLA-4 pathway inhibitor and a PD-L1 inhibitor or PD-L1 pathway inhibitor.

Accordingly, provided herein are embodiments of a method for treating prostate cancer in a subject, the method comprising administering to a subject a vaccine comprising a nucleic acid comprising a nucleotide sequence from a prostatic acid phosphatase (PAP) gene; and administering to the subject a human programmed death receptor-1 (PD-1) inhibitor and/or a human programmed death-ligand 1 (PD-L1). In some embodiments, the subjects have castration-resistant metastatic prostate cancer. In some embodiments, the nucleic acid further comprises a transcriptional regulatory element, e.g., in some embodiments the nucleotide sequence from a PAP gene is operatively linked to a transcriptional regulatory element (e.g., a nucleic acid comprising a transcriptional regulatory element, e.g., a nucleic acid comprising a nucleotide sequence encoding a transcriptional regulatory element (e.g., a core promoter, a proximal promoter, an enhancer, a locus control region, a transcription factor binding site, an activator, a coactivator, etc.)).

The technology is not limited in the source of the nucleic acid comprising a nucleotide sequence from a PAP gene. For instance, in some embodiments the nucleic acid comprises a nucleotide sequence from a human PAP gene and in some embodiments the nucleic acid comprises a nucleotide sequence from a rodent PAP gene. In some embodiments, the nucleic acid comprises a nucleotide sequence that encodes a polypeptide comprising an amino acid sequence provided by one of SEQ ID NO: 1, SEQ ID NO: 2, or SEQ ID NO: 3, or a portion or substituted variant thereof. In some embodiments, the nucleic acid is pTVG4-HP or comprises pTVG-HP. In some embodiments, the nucleic acid comprises a nucleotide sequence that encodes a polypeptide comprising an amino acid sequence that is at least 80% identical (e.g., at least 81%, 82%, 83%, 84%, 85%, 86%, 87%, 88%, 89%, 90%, 91%, 92%, 93%, 94%, 95%, 96%, 97%, 98%, or at least 99% identical) to an amino acid sequence provided by one of SEQ ID NO: 1, SEQ ID NO: 2, or SEQ ID NO: 3.

Further, the technology relates to treating a subject having a cancer (e.g., a prostate cancer) or who is at risk for having a cancer (e.g., a prostate cancer). In some embodiments, the subject is a human. In some embodiments, the subject is a human in need of a treatment for a cancer, e.g., in some embodiments the subject is a human in need of a treatment for a prostate cancer.

The technology is not limited in the PD-1 inhibitor that is administered. For instance, in some embodiments, the PD-1 inhibitor is an antibody (e.g., a monoclonal antibody) or an antigen-binding fragment of an antibody. In some embodiments, the PD-1 inhibitor is a monoclonal antibody that is, e.g., pembrolizumab or nivolumab.

Further, some embodiments relate to compositions comprising a PD-L1 inhibitor, methods comprising use (e.g., administration, etc.) of a PD-L1 inhibitor, etc. Accordingly, embodiments comprise antibodies (e.g., monoclonal antibodies), or an antigen-binding fragment of an antibody, that blocks PD-1 or PD-L1 and methods related to use of such antibodies and/or antibody fragments that block PD-1 or PD-L1. Accordingly, it is contemplated that, in some embodiments, PD-L1 inhibitors find use throughout the technologies described herein in place of PD-1 inhibitors (e.g., technologies comprising use of PD-1 inhibitors are contemplated in some embodiments to have PD-L1 inhibitors substituted for the PD-1 inhibitors). See, e.g., see, e.g., Rekoske et al. (2015) Cancer Immunol Res 3: 946-55, indicating antitumor activity of a DNA vaccine is increased when combined with an inhibitor of PD-1 or an inhibitor of PD-L1 (e.g., an anti-PD-1 antibody or an anti-PD-L1 antibody).

The technology provides several dosing schedules for administration of the vaccine and the PD-1 inhibitor. In some embodiments, the vaccine and the PD-1 inhibitor are administered concurrently (e.g., on the same day; e.g., administering the vaccine occurs within 1 to 5 and up to 24 hours of administering the PD-1 inhibitor).

In other embodiments, the PD-1 inhibitor is administered after the final dose of the vaccine has been administered, e.g., once a first dose of the PD-1 inhibitor has been administered, the vaccine is not administered during the dosing schedule for the PD-1 inhibitor. For example, in some embodiments the PD-1 inhibitor is administered more than 1, 2, 3, 4, 5, 6, 7, 8, 9, 10, 11, or more than 12 hours after the ultimate dose of the nucleic acid vaccine is administered to the subject.

The technology provides for the administration of the vaccine and the PD-1 inhibitor over a range of doses to provide an effective dose for a subject (e.g., a dose appropriate for the subject's weight, disease state, medical history, administration in concert with other drugs, etc.). For example, in some embodiments the PD-1 inhibitor is administered at a dose of from 1 to 5 mg/kg. And, in some embodiments, the vaccine is administered in an amount of approximately 100 µg. Further, the technology is not limited in the route of administration of the vaccine and the PD-1 inhibitor. For instance, in some embodiments the PD-1 inhibitor is administered intravenously. And, in some embodiments, the vaccine is administered intradermally. Further, embodiments provide that the PD-1 inhibitor is administered over a period of time (e.g., by an intravenous infusion). For instance, embodiments provide that the PD-1 inhibitor is administered over 30 minutes.

Further, embodiments of methods relate to dosage schedules that coordinate the administration of the vaccine with the PD-1 inhibitor in a series of administrations over multiple days, weeks, and/or months. In some embodiments of exemplary dosing schedules, the PD-1 inhibitor is administered every 3 weeks and/or the PD-1 inhibitor is administered 4 times. And, in some embodiments, the nucleic acid vaccine is administered every two weeks and/or the vaccine is administered 6 times.

Accordingly, in some embodiments, the vaccine and the PD-1 inhibitor are administered a plurality of times in an overlapping administration schedule. In some embodiments, the subjects have castration-resistant metastatic prostate cancer. In some embodiments, the first time the vaccine and the PD-1 inhibitor are administered concurrently (i.e., at day 1 of the treatment schedule within 24 hours of one another) and thereafter the vaccine is administered every 10 to 20 or 21, preferably about every 14 days and the PD-1 inhibitor is administered every 17 to 24 days, preferably about every 21 days for a period of up to 90 days. In some embodiments, the methods further comprise administering the vaccine every 10 to 20 or 21 days, preferably about every 14 days, and the PD-1 inhibitor every 17 to 24 days, preferably about every 21 days, for a period of from 91 days to 365 days. In some embodiments, patients that exhibit a decrease in PSA or tumor regression after 90 days are selected for the administration of the vaccine every 10 to 20 or 21 days and the PD-1 inhibitor every 17 to 24 days for a period of from 91 days to 365 days. In some embodiments, the methods further comprise administering the vaccine every 10 to 20 or 21 days, preferably about every 14 days, and the PD-1 inhibitor every 17 to 24 days, preferably about every 21 days, for a period of from 366 days to 730 days. In some embodiments, patients that exhibit a decrease in PSA or tumor regression after 365 days are selected for the administration of the vaccine every 10 to 20 or 21 days and the PD-1 inhibitor every 17 to 24 days for a period of from 366 days to 730 days. In some embodiments, the vaccine and the PD-1 inhibitor are administered in an overlapping schedule every 10 to 28 days, preferably every 10 to 20 or 21 days or 10 to 24 days, and most preferably about every 14 days or 21 days for a period of up to 90 days. In some embodiments, the methods further comprise administering the vaccine and the PD-1 inhibitor in an overlapping schedule every 10 to 28 days, preferably every 10 to 20 or 21 days or 10 to 24 days, and most preferably about every 14 days for a period of from 91 days to 365 days. In some embodiments, patients that exhibit a decrease in PSA or tumor regression after 90 days are selected for the administration of the vaccine and the PD-1 inhibitor in an overlapping schedule every 10 to 28 days, preferably every 10 to 20 or 21 days or 10 to 24 days, and most preferably about every 14 days for a period of from 91 days to 365 days. In some embodiments, the methods further comprise administering the vaccine and the PD-1 inhibitor in an overlapping schedule every 10 to 28 days, preferably every 10 to 20 or 21 days or 10 to 24 days, and most preferably about every 14 days for a period of from 366 days to 730 days. In some embodiments, patients that exhibit a decrease in PSA or tumor regression after 365 days are selected for the concurrent administration of the vaccine and the PD-1 inhibitor every 10 to 28 days, preferably every 10 to 20 or 21 days or 10 to 24 days, and most preferably about every 14 days for a period of from 366 days to 730 days. In some embodiments, the vaccine and PD-1 inhibitor are administered concurrently within the overlapping administration schedule. Concurrent administration encompasses administering the vaccine and the PD-1 inhibitor in the same composition (e.g., a solution), or where the agents are administered separately, administration in the same day and preferably administration within from about 1 minute to about 5 hours or 24 hours of one another or from about 30 minutes to about 5 hours or 24 hours of one another.

In further embodiments, the present invention provides methods for treating prostate cancer in a subject, the method comprising: (a) administering to a subject a vaccine comprising a nucleic acid comprising a nucleotide sequence from a prostatic acid phosphatase (PAP) gene; and (b) administering to the subject a human programmed death receptor-1 (PD-1) inhibitor, wherein the vaccine and the PD-1 inhibitor are administered a plurality of times on an overlapping schedule after the first administration of said vaccine and said PD-1 inhibitor. In some embodiments, the subjects have castration-resistant metastatic prostate cancer. In some embodiments, the vaccine is administered in advance of the PD-1 inhibitor when the first administered. In some embodiments, the vaccine and said PD-1 inhibitor are administered within 12, 24, 48 or 72 hours of one another at the beginning of the overlapping schedule. In some embodiments, after the first administration of the vaccine and the PD-1 inhibitor, the vaccine is administered every 10 to 20 or 21 days and the PD-1 inhibitor is administered every 17 to 24 days for a period of up to 90 days. In some embodiments, the methods further comprise administering the vaccine every 10 to 20 or 21 days and the PD-1 inhibitor every 17 to 24 days for a period of from 91 days to 365 days. In some embodiments, patients that exhibit a decrease in PSA or tumor regression after 90 days are selected for the administration of the vaccine every 10 to 20 or 21 days and the PD-1 inhibitor every 17 to 24 days for a period of from 91 days to 365 days. In some embodiments, the methods further comprise administering the vaccine every 10 to 20 or 21 days and the PD-1 inhibitor every 17 to 24 days for a period of from 366 days to 730 days. In some embodiments, patients that exhibit a decrease in PSA or tumor regression after 365 days are selected for the administration of the vaccine every 10 to 20 or 21 days and the PD-1 inhibitor every 17 to 24 days for a period of from 91 days to 365 days.

Further, one of ordinary skill in the art is able to provide a suitable pharmaceutical composition that comprises the nucleic acid vaccine and a suitable pharmaceutical composition that comprises the PD-1 inhibitor. For instance, in some embodiments the vaccine further comprises an adjuvant, e.g., GM-CSF, e.g., recombinant human GM-CSF.

Embodiments of the methods described elicit various physiological and immunological changes and responses in the subject. For instance, in some embodiments the method produces an anti-tumor response in the subject that is improved relative to administration of the nucleic acid vaccine alone. In particular embodiments, the method increases the number of PAP-specific T cells, increases the expression of PD-1 on circulating CD4+ or CD8+ T cells; decreases the amount of circulating tumor cells in the subject's blood, increases the amount of PAP-specific antibodies in the subject, elicits an immune response to non-PAP prostate associated antigens, increases expression of PD-L1 on circulating tumor cells in the subject's blood, and/or increases expression of PD-L1 on T-cells. In some embodiments, the physiological and immunological changes and responses in the subject are associated with changes in the levels or characteristics of biomarkers in the subject. For instance, in some embodiments the methods modulate the expression of TIM3, BTLA, CD160, CD244, and/or LAG3 on tumor-specific circulating T-cells or tumor-resident T-cells; modulate expression of HVEM, phosphatidyl serine, or PD-L2 on tumor cells; and/or modulate the amount of PD-1-regulated PAP-specific T-cells.

In some embodiments, methods comprise measuring PD-1 and/or PD-L1 expression, e.g., by measuring one or more of the following: 1) circulating PAP-specific CD8+ T-cell expressing PD-1 relative to circulating peripheral blood mononuclear cells; 2) tumor-resident PAP-specific CD8+ T-cells expressing PD-1; 3) circulating CD8+ T-cells expressing PD-1 (non-PAP-specific) relative to circulating peripheral blood mononuclear cells; 4) tumor-resident CD8+ T-cells expressing PD-1 (non-PAP-specific); 5) circulating PAP-specific CD8+ T-cell expressing PD-L1 relative to circulating peripheral blood mononuclear cells; 6) tumor-resident PAP-specific CD8+ T-cells expressing PD-L1; 7) circulating CD8+ T-cells expressing PD-L1 (non-PAP-specific) relative to circulating peripheral blood mononuclear cells; 8) tumor-resident CD8+ T-cells expressing PD-L1 (non-PAP-specific); 9) circulating PAP-specific CD4+ T-cell expressing PD-1 relative to circulating peripheral blood mononuclear cells; 10) tumor-resident PAP-specific CD4+ T-cells expressing PD-1; 11) circulating CD4+ T-cells expressing PD-1 (non-PAP-specific) relative to circulating peripheral blood mononuclear cells; 12) tumor-resident CD4+ T-cells expressing PD-1 (non-PAP-specific); 13) circulating PAP-specific CD4+ T-cell expressing PD-L1 relative to circulating peripheral blood mononuclear cells; 14) tumor-resident PAP-specific CD4+ T-cells expressing PD-L1; 15) circulating CD4+ T-cells expressing PD-L1 (non-PAP-specific) relative to circulating peripheral blood mononuclear cells; and/or 16) tumor-resident CD4+ T-cells expressing PD-L1 (non-PAP-specific).

In some preferred embodiments, PD-L1 provides a biomarker indicating that the combination therapy is or will be effective. That is, an increase in PD-L1 (e.g., an increased number of cells expressing PD-L1, either measured absolutely or relative to another biomarker) following administration of the vaccine comprising a nucleic acid comprising a nucleotide sequence from a prostatic acid phosphatase (PAP) gene provides an indication that administering to the subject a human programmed death receptor-1 (PD-1) inhibitor (e.g., an anti-PD-1 antibody) and/or a human programmed death-ligand 1 (PD-L1) inhibitor (e.g., an anti-PD-L1 antibody) will be a successful treatment. Thus, in some embodiments measurement of PD-L1 is made from a patient sample prior to treatment with the vaccine comprising a nucleic acid comprising a nucleotide sequence from a prostatic acid phosphatase (PAP) gene and a measurement of PD-L1 is made from a patient sample after treatment with the vaccine comprising a nucleic acid comprising a nucleotide sequence from a prostatic acid phosphatase (PAP) gene. An increase in the value for PD-L1 indicates an increased expectation of success that the human programmed death receptor-1 (PD-1) inhibitor (e.g., an anti-PD-1 antibody) and/or a human programmed death-ligand 1 (PD-L1) inhibitor (e.g., an anti-PD-L1 antibody) will be successful.

In some embodiments, a PD-L1 value is the number of circulating PD-L1 positive cells from a patient blood sample. In some embodiments, a PD-L1 value is a percentage of circulating PD-L1 positive cells relative to PBMC in the patient blood sample. In some embodiments, the number of CD45 negative, EPCAM positive viable cells that are PD-L1 positive is measured in a patient blood sample, e.g., enumerated or as a percentage of PBMC in the patient blood sample. In some embodiments, the presence of CD45 negative, EPCAM positive viable cells that are PD-L1 positive or a detected increase of CD45 negative, EPCAM positive viable cells that are PD-L1 positive indicates that the treatment will produce a long-term Th-1 biased phenotype of T-cells (e.g., either CD4+ or CD8+ T-cells), e.g., that secrete gamma interferon, and/or indicates that the treated patient will be progression free at 2 years.

In some embodiments, a PD-L1 value is measured in a tumor (e.g., in the tumor microenvironment). For example, in some embodiments, the number of PD-L1 positive cells in a patient tumor is measured as a percentage of cells taken in a sample from the tumor (e.g., a number of PD-L1 positive cells relative to all cells viewed in a microscope field).

In some embodiments, the subject has a low level of PD-L1, a level of PD-L1 in need of an increase, and/or a level of PD-L1 below a target level of PD-L1 (e.g., as appropriate for the PD-L1 inhibitor to be effective). For instance, in some embodiments the subject has a level of PD-L1 that is less than a measured, empirically established, or previously known cutoff for a low level of PD-L1; in some embodiments the subject has a level of PD-L1 that is less than a measured, empirically established, or previously known lower bound of a target range for PD-L1. In some embodiments methods comprise measuring a PD-L1 level of the subject (e.g., to determine if the subject has a low level of PD-L1, to determine the dose of the DNA vaccine to administer (e.g., to increase the PD-L1 level to be within a target range, etc.)), e.g., in some embodiments the methods comprise measuring the level of PD-L1 in a sample from the subject. In some embodiments, the result of measuring the PD-L1 level is used to inform subsequent administrations of the DNA vaccine, e.g., to adjust the dose, e.g., to increase the PD-L1 level to be within a target range. Accordingly, in some embodiments methods further comprise a second administering to the subject of the vaccine comprising a nucleic acid comprising a nucleotide sequence from a prostatic acid phosphatase (PAP) gene. The technology is not limited in the series of administering and measuring, e.g., in some embodiments methods comprise one or more steps of administering the vaccine and/or one or more steps of measuring a PD-L1 level on the subject.

For example, in some embodiments, the subject has a low or undetectable level of circulating tumor cells or tumor-resident cells expressing PD-L1 prior to vaccination and the number of circulating tumor cell or tumor-resident cells expressing PD-L1 increases after vaccination. For instance, in some embodiments, a subject prior to vaccination has less than 1 circulating tumor cell expressing PD-L1 per 1000 circulating peripheral blood mononuclear cells and the subject has more than 1 circulating tumor cell expressing PD-L1 per 1000 circulating peripheral blood mononuclear cells after vaccination according to the technology provided herein. In some embodiments, a subject prior to vaccination has less than 1 circulating tumor cell expressing PD-L1 per 5000 circulating peripheral blood mononuclear cells and the subject has more than 1 circulating tumor cell expressing PD-L1 per 5000 circulating peripheral blood mononuclear cells after vaccination according to the technology provided herein. In some embodiments, a subject prior to vaccination has less than 1 circulating tumor cell expressing PD-L1 per 10,000 circulating peripheral blood mononuclear cells and the subject has more than 1 circulating tumor cell expressing PD-L1 per 10,000 circulating peripheral blood mononuclear cells after vaccination according to the technology provided herein. In some embodiments, a subject prior to vaccination has less than 1 circulating tumor cell expressing PD-L1 per 50,000 circulating peripheral blood mononuclear cells and the subject has more than 1 circulating tumor cell expressing PD-L1 per 50,000 circulating peripheral blood mononuclear cells after vaccination according to the technology provided herein. In some embodiments, a subject prior to vaccination has less than 1 circulating tumor cell expressing PD-L1 per 100,000 circulating peripheral blood mononuclear cells and the subject has more than 1 circulating tumor cell expressing PD-L1 per 100,000 circulating peripheral blood mononuclear cells after vaccination according to the technology provided herein. In some embodiments, a subject prior to vaccination has less than 1 circulating tumor cell expressing PD-L1 per 500,000 circulating peripheral blood mononuclear cells and the subject has more than 1 circulating tumor cell expressing PD-L1 per 500,000 circulating peripheral blood mononuclear cells after vaccination according to the technology provided herein. And, in some embodiments, a subject prior to vaccination has less than 1 circulating tumor cell expressing PD-L1 per 1,000,000 circulating peripheral blood mononuclear cells and the subject has more than 1 circulating tumor cell expressing PD-L1 per 1,000,000 circulating peripheral blood mononuclear cells after vaccination according to the technology provided herein.

In some embodiments a subject prior to vaccination with the technology described herein is an unvaccinated subject and in some embodiments a subject prior to vaccination with the technology described herein is a subject having been vaccinated according to the technology provided one or more times.

Thus, in some embodiments, a subject prior to vaccination has a low percentage of circulating tumor cells or tumor-resident cells expressing PD-L1; a percentage of circulating tumor cells or tumor-resident cells expressing PD-L1 in need of an increase; and/or a percentage of circulating tumor cells or tumor-resident cells expressing PD-L1 below a target percentage of circulating tumor cells or tumor-resident cells expressing PD-L1 (e.g., as appropriate for the PD-L1 inhibitor to be effective). For instance, in some embodiments, the subject has a percentage of circulating tumor cells or tumor-resident cells expressing PD-L1 that is less than 0.1%, 0.02%, 0.01%, 0.002%, 0.001%, 0.0002%, or 0.0001% of the total circulating peripheral blood mononuclear cells (e.g., providing a cutoff for a lower level and/or a lower bound of a target range).

In some embodiments, a subject after vaccination has an increased percentage of circulating tumor cells or tumor-resident cells expressing PD-L1; and/or a percentage of circulating tumor cells or tumor-resident cells expressing PD-L1 above a target percentage of circulating tumor cells or tumor-resident cells expressing PD-L1 (e.g., as appropriate for the PD-1 and/or PD-L1 inhibitor to be effective). For instance, in some embodiments, the subject has a percentage of circulating tumor cells or tumor-resident cells expressing PD-L1 that is greater than 0.1%, 0.02%, 0.01%, 0.002%, 0.001%, 0.0002%, or 0.0001% of the total circulating peripheral blood mononuclear cells after treatment.

In some embodiments, methods comprise measuring a percentage of circulating tumor cells or tumor-resident cells expressing PD-L1 in a sample from a subject. In some embodiments, the methods comprise measuring a percentage of circulating tumor cells or tumor-resident cells expressing PD-L1 in a sample from a subject prior to vaccination. In some embodiments, the methods comprise measuring a percentage of circulating tumor cells or tumor-resident cells expressing PD-L1 in a sample from a subject after vaccination. In some embodiments, the methods comprise measuring a percentage of circulating tumor cells or tumor-resident cells expressing PD-L1 in a sample from a subject one or more times prior to vaccination and one or more times after vaccination.

In some embodiments, the result of measuring the percentage of circulating tumor cells or tumor-resident cells expressing PD-L1 in a sample from a subject is used to identify a subject having a low percentage of circulating tumor cells or tumor-resident cells expressing PD-L1, e.g., to identify a subject in need of vaccination according to the technology provided herein, to determine the dose of the DNA vaccine to administer (e.g., to increase the percentage of circulating tumor cells or tumor-resident cells expressing PD-L1 to be within a target range, etc.) In some embodiments, the result of measuring the percentage of circulating tumor cells or tumor-resident cells expressing PD-L1 is used to inform subsequent administrations of the DNA vaccine, e.g., to adjust the dose and/or dose schedule, e.g., to increase the percentage of circulating tumor cells or tumor-resident cells expressing PD-L1 to be within a target range.

In some embodiments, the result of measuring the percentage of circulating tumor cells or tumor-resident cells expressing PD-L1 in a sample from a subject is used to identify a subject having an increased amount (e.g., an increased percentage) of circulating tumor cells or tumor-resident cells expressing PD-L1, e.g., to identify a subject in which the vaccination has been effective.

The technology is not limited in the assay used to measure (count, quantify, characterize, etc.) cell numbers. In some embodiments, cells expressing a biomarker (e.g., PD-1 or PD-L1) are measured. In some embodiments, the number of circulating tumor cells or tumor-resident cells expressing a biomarker is measured. In some embodiments, cell numbers are measured relative to another type of cell or all cells detectable. For instance, in some embodiments the number of circulating tumor cells expressing a biomarker (e.g., PD-1, PD-L1, or another biomarker or combination of biomarkers as described herein) is measured relative to the number of circulating peripheral blood mononuclear cells. Or, in some embodiments the number of tumor-resident cells expressing a biomarker (e.g., PD-1, PD-L1, or another biomarker or combination of biomarkers as described herein) is measured as a percentage of cells taken from a tumor (e.g., the number of tumor-resident cells is measured as a percentage of cells viewed in the field of a microscope view field), e.g., to measure the percentage of circulating tumor cells or tumor-resident cells expressing a biomarker. For instance, in some embodiments the number of circulating tumor cells or tumor-resident cells expressing a biomarker and/or the number of circulating peripheral blood mononuclear cells expressing a biomarker are measured using flow cytometry. In some embodiments, measuring cells expressing a biomarker comprises measuring a mean fluorescence intensity (MFI) of the cells for the biomarker (e.g., measuring a MFI for a biomarker such as, e.g., PD-1 and/or PD-L1, in a population of cells.) In some embodiments, the number of circulating tumor cells or tumor-resident cells expressing a biomarker and/or the number of circulating peripheral blood mononuclear cells are measured using an certain dyes or stains (e.g., in some embodiments a dye or stain attached to an antibody specific for the biomarker).

In some embodiments, circulating tumor cells are identified using a flow-based assay. For example, in some embodiments, cells are identified based on identification of live single cells that are CD45−, EpCAM+, and express the PD-1 or PD-L1 biomarker.

In some embodiments, the number of circulating tumor cells or tumor-resident cells expressing a biomarker and/or the number of circulating peripheral blood mononuclear cells are measured using an immunoassay or other technologies known in the art for counting cells, types of cells, cells expressing one or more specified biomarkers. In some embodiments, the number of circulating tumor cells or tumor-resident cells expressing a biomarker and/or the number of circulating peripheral blood mononuclear cells are measured using an immunoassay or other technologies known in the art for counting cells, types of cells, cells expressing one or more specified biomarkers, etc. Some embodiments for enumerating circulating tumor cells comprise techniques that rely on CTC expression of epithelial markers (EpCAM, cytokeratin), depletion of cells expressing a common leukocyte marker (CD45), selection of cells with specific physical properties (cell size, density, deformity), microfluidic platforms (e.g., to select or identify CTC by size and/or deformity), or a combination of epitope and physical property selection. For example, in some embodiments EpCAM and CD45 are stained on cells (e.g., with one or more fluorescent antibodies). In some embodiments, the living EpCAM positive cells are detected and enumerated microscopically. In some embodiments, live cells are identified using a dead/live staining dye, e.g., propidium iodide. Kits for enumerating cells that are based on such technologies are available commercially, e.g., as the MAINTRAC (SIMFO GmbH, Bayreuth, Germany) blood test for circulating tumor cells. In some embodiments, detection of CTC comprises use of both protein biomarkers (e.g., as detected by immunofluorescence) and genetic (e.g., as detected by FISH, NGS) biomarkers. In some embodiments, CTC are identified by a plurality of antibodies targeting cytokeratins (CK) and CD45, and the dye 4',6-diamidino-2-phenylindole, dihydrochloride (DAPI), e.g., as available commercially from Epic Sciences (see, e.g., Werner et al. (2015) "Analytical Validation and Capabilities of the Epic CTC Platform: Enrichment-Free Circulating Tumour Cell Detection and Characterization", J Circ Biomark, 2015, 4:3. In some embodiments, CTC of epithelial origin are enumerated by detecting cells that are CD45−, EpCAM+, and display the cytokeratins 8, 18+, and/or 19+) in whole blood (e.g., as provided commercially as the CELLSEARCH® Circulating Tumor Cell Kit by Janssen Diagnostics, LLC, Raritan, N.J.).

Further embodiments are related to kits for treating a subject having prostate cancer or who is at risk of having prostate cancer. Embodiments of kits comprise one or more vessels comprising pharmaceutical formulations for administration to a subject. For instance, in some embodiments, kits comprise a first pharmaceutical composition comprising a vaccine comprising a nucleic acid comprising a nucleotide sequence from a PAP gene; and a second pharmaceutical composition comprising a PD-1 inhibitor. As discussed herein, in various embodiments the nucleic acid comprises a nucleotide sequence from a PAP gene, e.g., a PAP gene from a human or a rodent (e.g., the nucleic acid comprises a nucleotide sequence that encodes a polypeptide or a peptide provided by an amino acid sequence according to SEQ ID NO: 1, SEQ ID NO: 2, or SEQ ID NO: 3), though the technology is not limited in the genome, organism, strain, etc. from which the PAP gene or gene sequence is obtained. In some embodiments, the nucleic acid consists of or comprises pTVG-HP. In some embodiments, the second pharmaceutical composition comprises an antibody (e.g., a monoclonal antibody), e.g., pembrolizumab and/or nivolumab. Some kit embodiments provide the first and second pharmaceutical compositions as single doses, e.g., to provide convenience for administration and, further, to eliminate and/or reduce errors in measuring and/or administering a dose. In some embodiments, the kit comprises multiple doses of the vaccine and/or PD-1 inhibitor to provide the multiple doses for a dosing schedule. Accordingly, in some embodiments the kit comprises an amount (e.g., in a number of doses) of the first pharmaceutical composition and an amount (e.g., in a number of doses) of the second pharmaceutical composition sufficient to provide enough doses for a dosing schedule in which the nucleic acid vaccine and the PD-1 inhibitor are administered multiple times. In some embodiments, the doses are provided in individual volumes (e.g., one volume and/or one vessel per dose, e.g., each dose is provided in a separate volume and/or vessel) and in some embodiments multiple doses are provided in the same volume and/or vessel).

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
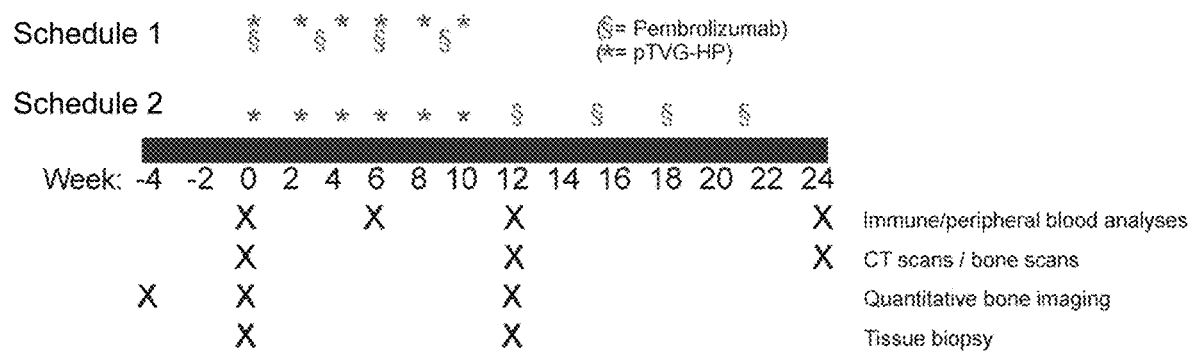
FIG. 1: Schematic showing embodiments of two dosage schedules described herein.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to cancer treatment and prevention and particularly, but not exclusively, to compositions and methods related to therapies for prostate cancer. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the "best overall response" is the best response recorded from baseline until disease progression/recurrence, taking as reference for progressive disease the smallest measurements recorded after baseline.

As used herein, the "first documentation of response" refers to the time between initiation of therapy and first documentation of a partial response or complete response to therapy as defined herein.

As used herein, the "duration of response" refers to the period measured from the time that measurement criteria are met for complete or partial response (whichever status is recorded first) until the first date that recurrent or progressive disease is objectively documented, taking as reference the smallest measurements recorded since treatment started.

As used herein, the "duration of overall complete response" refers to the period measured from the time measurement criteria are met for complete response until the first date that recurrent disease is objectively documented.

As used herein, the "duration of stable disease" refers to a measurement from baseline until the criteria for disease progression is met, taking as reference the smallest measurements recorded since baseline.

As used herein, "survival" refers to the time interval from initiation of a treatment according to the technology described to death from any cause or to the last follow-up in censored patients.

As used herein, the terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein. Where the term "amino acid sequence" is recited herein to refer to an amino acid sequence of a protein molecule, "amino acid sequence" and like terms such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. Conventional one and three-letter amino acid codes are used herein as follows—Alanine: Ala, A; Arginine: Arg, R; Asparagine: Asn, N; Aspartate: Asp, D; Cysteine: Cys, C; Glutamate: Glu, E; Glutamine: Gln, Q; Glycine: Gly, G; Histidine: His, H; Isoleucine: Ile, I; Leucine: Leu, L; Lysine: Lys, K; Methionine: Met, M; Phenylalanine: Phe, F; Proline: Pro, P; Serine: Ser, S; Threonine: Thr, T; Tryptophan Trp, W; Tyrosine: Tyr, Y; Valine: Val, V. As used herein, the codes Xaa and X refer to any amino acid.

The term "portion" when used in reference to a protein (as in "a portion of a given protein") refers to fragments of that protein, such as "peptides" of the protein. The fragments may range in size from four amino acid residues to the entire amino sequence minus one amino acid (for example, the range in size includes 4, 5, 6, 7, 8, 9, 10, or more amino acids up to the entire amino acid sequence minus one amino acid).

The term "homolog" or "homologous" when used in reference to a polypeptide refers to a high degree of sequence identity between two polypeptides, or to a high degree of similarity between the three-dimensional structure, or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine More rarely, a variant may have "non-conservative" changes (e.g., replacement of a glycine with a tryptophan). Similar minor variations may also include amino acid deletions or insertions (e.g., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The nomenclature used to describe variants of nucleic acids or proteins specifies the type of mutation and base or amino acid changes. For a nucleotide substitution (e.g., 76A>T), the number is the position of the nucleotide from the 5' end, the first letter represents the wild type nucleotide, and the second letter represents the nucleotide which replaced the wild type. In the given example, the adenine at the 76th position was replaced by a thymine. If it becomes necessary to differentiate between mutations in genomic DNA, mitochondrial DNA, complementary DNA (cDNA), and RNA, a simple convention is used. For example, if the 100th base of a nucleotide sequence is mutated from G to C, then it would be written as g.100G>C if the mutation occurred in genomic DNA, m.100G>C if the mutation occurred in mitochondrial DNA, c.100G>C if the mutation occurred in cDNA, or r.100g>c if the mutation occurred in RNA. For amino acid substitution (e.g., D111E), the first letter is the one letter code of the wild type amino acid, the number is the position of the amino acid from the N-terminus, and the second letter is the one letter code of the amino acid present in the mutation. Nonsense mutations are represented with an X for the second amino acid (e.g. D111X). For amino acid deletions (e.g. ΔF508, F508del), the Greek letter Δ (delta) or the letters "del" indicate a deletion. The letter refers to the amino acid present in the wild type and the number is the position from the N terminus of the amino acid where it is present in the wild type. Intronic mutations are designated by the intron number or cDNA position and provide either a positive number starting from the G of the GT splice donor site or a negative number starting from the G of the AG splice acceptor site. g.3' +7G>C denotes the G to C substitution at nt +7 at the genomic DNA level. When the full-length genomic sequence is known, the mutation is best designated by the nucleotide number of the genomic reference sequence. See den Dunnen & Antonarakis, "Mutation nomenclature extensions and suggestions to describe complex mutations: a discussion". Human Mutation 15: 7-12 (2000); Ogino S, et al., "Standard Mutation Nomenclature in Molecular Diagnostics: Practical and Educational Challenges", J. Mol. Diagn. 9(1): 1-6 (February 2007), incorporated herein by reference in their entireties for all purposes.

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include the transmembrane domains, and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The terms encompass sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, Adv. Appl. Math. 2: 482 (1981)] by the homology alignment algorithm of Needleman and Wunsch [Needleman and Wunsch, J. Mol. Biol. 48:443 (1970)], by the search for similarity method of Pearson and Lipman [Pearson and Lipman, Proc. Natl. Acad. Sci. (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process.

As used herein, the "level" of a biomarker or a "level" of expression of a biomarker (e.g., a biomarker including but not limited to PD-1, PD-L1, EpCam, CD4, CD8, CD45, CTLA-4, or a biomarker as produced by a stain such as DAPI or a live/dead stain) refers to the number of cells expressing the biomarker (e.g., as an absolute number or calculated relative to another cell population (e.g., total cells)) or the average per-cell expression of the biomarker on the surface of a population of cells.

"Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the term "operably linked" is intended to mean that the transcription or translation of a nucleotide sequence is under the influence of another functional nucleotide sequence, such as a promoter, an enhancer, a transcription factor binding site, etc. "Operably linked" is also intended to mean the joining of two nucleotide sequences such that the coding sequence of each DNA fragment remains in the proper reading frame. In this manner, the nucleotide sequences for promoters, enhancers, etc. are provided in DNA constructs along with the nucleotide sequence of interest, e.g., a nucleotide sequence encoding PAP, for expression in the subject. The term "heterologous nucleotide sequence" is intended to mean a sequence that is not naturally operably linked with the promoter sequence. While this nucleotide sequence is heterologous to the promoter sequence, it may be homologous ("native") or heterologous ("foreign") to the subject.

As used herein, the term "treatment" is defined as the application or administration of a therapeutic agent described herein (e.g., a DNA vaccine, a PD-1 inhibitor), or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, the term "at risk for disease" refers to a subject that is predisposed to experiencing a particular disease (e.g., prostate cancer). This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk, nor is it intended that the present invention be limited to any particular disease.

As used herein, a "stable" compound is a compound that can be prepared and isolated and whose structure and properties remain or can be caused to remain essentially unchanged for a period of time sufficient to allow use of the compound for the purposes described herein (e.g., therapeutic, prophylactic, and/or diagnostic administration to a subject).

Compositions according to the technology can be administered in the form of pharmaceutically acceptable salts. The term "pharmaceutically acceptable salt" refers to a salt that possesses the effectiveness of the parent compound and is not biologically or otherwise undesirable (e.g., is neither toxic nor otherwise deleterious to the recipient thereof). Suitable salts include acid addition salts that may, for example, be formed by mixing a solution of the compound of the present technology with a solution of a pharmaceutically acceptable acid such as hydrochloric acid, sulfuric acid, acetic acid, trifluoroacetic acid, or benzoic acid. Certain of the compounds employed in the present technology may carry an acidic moiety (e.g., COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (COOH) or alcohol group being present, pharmaceutically acceptable esters can be employed to modify the solubility or hydrolysis characteristics of the compound. For example, pharmaceutically acceptable salts include both the metallic (inorganic) salts and organic salts, a list of which is given in Remington's Pharmaceutical Sciences, 17th Edition, pg. 1418 (1985). It is well known to one skilled in the art that an appropriate salt form is chosen based on physical and chemical properties. As will be understood by those skilled in the art, pharmaceutically acceptable salts include, but are not limited to salts of inorganic acids such as hydrochloride, sulfate, phosphate, diphosphate, hydrobromide, and nitrate; or salts of an organic acid such as malate, maleate, fumarate, tartrate, succinate, citrate, acetate, lactate, methanesulfonate, p-toluenesulfonate or palmoate, salicylate, and stearate. Similarly pharmaceutically acceptable cations include, but are not limited to sodium, potassium, calcium, aluminum, lithium, and ammonium (especially ammonium salts with secondary amines). Also included within the scope of this technology are crystal forms, hydrates, and solvates.

The term "administration" and variants thereof (e.g., "administering" a compound, vaccine, drug, etc.) in reference to a compound mean providing the compound or a prodrug of the compound to the individual in need of treatment or prophylaxis. When a compound of the technology or a prodrug thereof is provided in combination with one or more other active agents, "administration" and its variants are each understood to include provision of the compound or prodrug and other agents at the same time or at different times. As used herein, the term "concurrent administration" refers to the administration of two agents, preferably within 24 hours of one another. When the agents of a combination are administered "concurrently" (e.g., within 24 hours of one another), they can be administered together in a single composition or they can be administered separately. In instances where they are administered separately, the first agent such as a PAP vaccine, is administered, the patient is monitored, and then the second agent such as PD-1 inhibitor is administered within a specified time period, preferably 24 hours. As used herein, the term "composition" is intended to encompass a product comprising the specified ingredients in the specified amounts, as well as any product that results, directly or indirectly, from combining the specified ingredients in the specified amounts.

As used herein, the terms "co-administration" and "co-administering" refer to the administration of at least two agent(s) (e.g., a DNA vaccine and a PD-1 inhibitor) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutically acceptable" means that the ingredients of the pharmaceutical composition are compatible with each other and not deleterious to the recipient thereof.

The term "subject" as used herein refers to an animal, preferably a mammal, most preferably a human, who has been the object of treatment, observation, or experiment.

The term "effective amount" as used herein means that amount of active compound or pharmaceutical agent that elicits the biological or medicinal response in a cell, tissue, organ, system, animal, or human that is being sought by a researcher, veterinarian, medical doctor, or other clinician. In some embodiments, the effective amount is a "therapeutically effective amount" for the alleviation of the symptoms of the disease or condition being treated. In some embodiments, the effective amount is a "prophylactically effective amount" for prophylaxis of the symptoms of the disease or condition being prevented. When the active compound is administered as the salt, references to the amount of active ingredient are to the free form (the non-salt form) of the compound.

In the method of the present technology, compounds, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the technology can, for example, be administered orally, parenterally (including subcutaneous injections, intravenous, intramuscular, intrasternal injection, or infusion techniques), by inhalation spray, or rectally, in the form of a unit dosage of a pharmaceutical composition containing an effective amount of the compound and conventional non-toxic pharmaceutically-acceptable carriers, adjuvants, and vehicles. Liquid preparations suitable for oral administration (e.g., suspensions, syrups, elixirs, and the like) can be prepared according to techniques known in the art and can employ any of the usual media such as water, glycols, oils, alcohols, and the like. Solid preparations suitable for oral administration (e.g., powders, pills, capsules, and tablets) can be prepared according to techniques known in the art and can employ such solid excipients as starches, sugars, kaolin, lubricants, binders, disintegrating agents, and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution, or a solution containing a mixture of saline and glucose. Further description of methods suitable for use in preparing pharmaceutical compositions for use in the present technology and of ingredients suitable for use in the compositions is provided in *Remington's Pharmaceutical Sciences,* 18th edition, edited by A. R. Gennaro, Mack Publishing Co., 1990. Compounds of the present technology can be made by a variety of methods depicted in the synthetic reaction schemes provided herein. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*, Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40.

As used herein, the term "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reactions that occur within a natural environment.

As used herein, the term "a composition for inducing an immune response" refers to a composition that, once administered to a subject (e.g., once, twice, three times or more (e.g., separated by weeks, months or years)), stimulates, generates, and/or elicits an immune response in the subject (e.g., resulting in the production of antibodies). In some embodiments, the composition comprises a nucleic acid and one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response.

As used herein, the term "adjuvant" refers to any substance that can stimulate an immune response. Some adjuvants can cause activation of a cell of the immune system (e.g., an adjuvant can cause an immune cell to produce and secrete a cytokine). Examples of adjuvants that can cause activation of a cell of the immune system include, but are not limited to, Granulocyte-macrophage colony-stimulating factor (GM-CSF), saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present technology are administered with one or more adjuvants.

As used herein, the term "an amount effective to induce an immune response" (e.g., of a composition for inducing an immune response), refers to the dosage level required (e.g., when administered to a subject) to stimulate, generate, and/or elicit an immune response in the subject. An effective amount can be administered in one or more administrations (e.g., via the same or different route), applications, or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens or self-antigens recognized as foreign). Thus, it is to be understood that, as used herein, "immune response" refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen as well as acquired (e.g., memory) responses that are a result of an adaptive immune response).

As used herein, the terms "immunogen" and "antigen" refer to an agent (e.g., a PAP polypeptide) and/or portion or component thereof (e.g., a peptide from a PAP polypeptide) that is capable of eliciting an immune response in a subject.

As use herein, the term "disease progression" refers to the appearance of new evidence of advancement of disease by a diagnostic assay such as a molecular assay or imaging assay, for example, the appearance of new lesions on bone scan.

Description

Although the disclosure herein refers to certain illustrated embodiments, it is to be understood that these embodiments are presented by way of example and not by way of limitation.

PAP

Prostatic acid phosphatase (PAP) is a tumor antigen in prostate cancer and PAP-specific CD8+ CTL can lyse prostate cancer cells. PAP was first identified in 1938 and was initially used as a serum marker for the detection of prostate cancer [22, 32]. PAP expression in normal and malignant prostate cells is well-documented, and is still used in immunohistochemical staining to establish a prostate origin of metastatic carcinoma [33]. The ubiquitous expression of PAP in prostate tissue makes it an appealing antigen as a potential "universal" target for immune-directed therapies of prostate cancer, unlike specific oncogenes that may or may not be expressed by a particular tumor. Moreover, it has been demonstrated that some patients with prostate cancer have preexisting antibody and T-cell responses to PAP, suggesting that tolerance to this "self" protein can be circumvented in vivo [34, 35]. In particular, Th1-like immune responses specific for PAP indicate that an immune environment permissive of an anti-tumor response exists in patients even without immunization [36]. Moreover, experiments have previously demonstrated that CD8+ T cells specific for PAP, with cytolytic activity for prostate cancer cells, exist in patients with prostate cancer and can be augmented with vaccination [30, 36].

PD-1 and/or PD-L1 Blockade

A major mechanism by which tumors avoid immune detection is by expressing PD-L1 or PD-L2, which are ligands for the T-cell receptor PD-1. Activation of PD-1 by PD-L1 or PD-L2 decreases T-cell function and increases immune tolerance. There is currently great enthusiasm to develop PD/PD-L (e.g., PD-1 and/or PD-L1) inhibitors given the relative paucity of adverse events observed with these agents in clinical trials and long-term disease response observed in some instances in early phase clinical trials. Targeting PD-1, in particular, should be a universal therapy, as it targets the T-cell compartment rather than the tumor directly. However, clinical trial experience to date suggests that patients with some solid tumor types (notably renal cell cancer, melanoma, and non-small cell lung cancer) experience more benefit than patients with other histologies, including prostate cancer [18, 19]. Differences in the T-cells of responding and non-responding patients may be the basis of this disparity. In particular, higher frequencies of tumor-infiltrating lymphocytes (TIL) are typically observed in patients with renal cell cancer and melanoma than prostate cancer. In addition, early phase clinical trials using PD-1 or PD-L1 have identified that the expression of at least one of the ligands for PD-1 (PD-L1) on the target tumor cell by biopsy is associated with clinical response to therapy [18]. This is expected, given that tissue-infiltrating T cells can induce the expression of PD-L1 via the expression of IFNγ, and ligand binding of PD-1 leads to decrease in T-cell effector function. It has been demonstrated that prostate cancers can express PD-L1, and can have infiltrating PD-1-expressing T cells [20]. Taken together, these results indicate that the efficacy of anti-tumor immunotherapy would be increased for prostate cancer by combining agents able to increase the number of tumor-specific T cells, such as through vaccination, and by PD blockade and/or by PD-L blockade (e.g., PD-1 and/or PD-L1 blockade), e.g., by a PD inhibitor and/or by a PD-L inhibitor (e.g., a PD-1 inhibitor (e.g., an anti-PD-1 antibody) and/or a PD-L1 inhibitor (e.g., an anti-PD-L1 antibody)).

Given the anti-tumor responses observed in early phase clinical trials with antibodies targeting either PD-1 or PD-L1, several pharmaceutical companies have been developing related agents. Currently, one agent has been approved as a therapy, pembrolizumab (KEYTRUDA, Merck). Specifically, pembrolizumab was approved in September 2014 for the treatment of ipilimumab-refractory advanced melanoma as a "breakthrough" therapy on the basis of an open-label, international, multicenter expansion cohort of a phase I trial of patients with advanced (metastatic) melanoma whose disease had progressed following treatment with ipilimumab [37]. In that trial, 173 patients received pembrolizumab at one of two doses (2 mg/kg or 10 mg/kg) at 3-week intervals until disease progression or intolerable toxicity. An overall response rate of 26% was observed, irrespective of dose [37]. Grade 3 fatigue was the only drug-related grade 3 or 4 adverse event reported in more than one patient. Given these findings, pembrolizumab is currently FDA approved for the treatment of patients with ipilimumab-refractory melanoma, dosed at 2 mg/kg intravenously every 3 weeks until disease progression or intolerable adverse effects. Of note, however, earlier phase clinical trials have suggested that treatment can lead to prolonged responses even after discontinuing treatment [15].

DNA Vaccines Elicit Antigen-Specific Th1/CTL Immune Responses

Over the last decade, there has been considerable interest in the development of plasmid DNA-based vaccines, a strategy that offers several distinct advantages over other methods of antigen delivery. DNA can be rapidly and inexpensively purified and DNA is greatly more soluble than peptides and recombinant proteins. In addition, because the DNA in nucleic acid vaccines has been demonstrated to be taken up and expressed by host tissues and presented by host antigen-presenting cells (APC) directly [38, 39, 40], antigen presentation occurs through naturally processed epitopes, and does not require autologous cell processing. DNA vaccines can therefore be theoretically employed in an HLA-independent fashion unlike peptide-based vaccines that are necessarily HLA-restricted. This strategy is ideal in the HLA-diverse human situation. In many ways, this method of immunization is similar to the use of viral immunization vectors, however without the additional foreign antigens introduced with a viral vector and consequently less of a risk of an overwhelming immune response to the vector itself [26, 41]. Of importance in tumor immunization models, several groups have demonstrated that immunization with plasmid DNA encoding a target antigen is a potent means of eliciting Th1-biased immune responses [42] and CD8+ T-cells specific for the targeted antigen [38, 43, 44, 45, 46]. In animal models, the use of an intradermal route of vaccine administration, in particular, tends to promote this Th1/CTL-biased immune response [42, 47, 48]. It should also be acknowledged that the clinical efficacy of a DNA vaccine encoding tyrosinase for the treatment of canine melanoma was approved by the USDA in early 2010 based on the results of clinical studies demonstrating an improved survival of companion dogs with oral melanoma [49, 50]. In fact, this represents the first vaccine approved in the U.S. for the treatment of existing cancer. Thus, this approach bears further investigation in human clinical trials.

DNA Vaccine Encoding PAP (pTVG-HP) Elicits Antigen-Specific CD4+ and CD8+ T Cells in Patients with Prostate Cancer It has been previously reported that DNA vaccines encoding either the human or rat homologue of PAP elicits PAP-specific CD4+ and CD8+ T cells in rats, suggesting a feasible means of eliciting PAP-specific anti-tumor immune responses in patients [25, 26]. Subsequently, data have been reported from a phase I/II clinical trial in which subjects with non-castrate, non-metastatic prostate cancer were immunized six times at two-week intervals with this same DNA vaccine. These data were collected to evaluate the safety and immunological efficacy of the pTVG-HP DNA vaccine in patients with clinical stage D0 prostate cancer [51]. This was a dose-escalation study, with an expanded cohort of subjects treated at the maximum tolerated dose. In the dose-escalation portion, nine subjects were treated in three dose cohorts of 100 µg, 500 µg, or 1500 µg DNA, administered intradermally every two weeks for six total immunizations. 200 µg GM-CSF was co-administered as a vaccine adjuvant with each immunization. 13 additional subjects were treated in an expanded cohort at the 1500 µg DNA dose. No serious adverse events were observed, and no significant laboratory anomalies were observed. Common events observed were grade 1/2 fevers, chills, and local site reactions lasting typically less than 24 hours. The primary immunological endpoint of this study was the induction of PAP-specific IFNγ-secreting effector CD8+ T cells detectable two weeks following the final immunization. As previously reported, three patients had a significant increase in the number of PAP-specific IFNγ-secreting CD8+ T cells after immunization compared with pre-immunization, one patient from each dose cohort [29]. Several individuals experienced a prolongation in PSA doubling time over one year following treatment compared with pre-treatment. Overall the median PSA doubling time was 6.5 months in the four months pre-treatment and 8.5 months in the 4-month on-treatment period (p=0.033). Long-term PAP-specific IFNγ-secreting T-cell responses were observed in several patients up to one year after immunization; the presence of this persistent immunity was associated with favorable changes in PSA doubling time [30].

A second set of experiments evaluated different schedules of immunization in patients with castrate-resistant, non-radiographically metastatic prostate cancer. This study was designed to answer the question of whether six immunizations were insufficient in some individuals to develop an immune response, and whether ongoing repetitive immunization might be necessary. This study demonstrated that PAP-specific immune responses developed in some individuals after as few as 3-6 immunizations, and some individuals developed no detectable immune responses after even 24 biweekly immunizations [31]. Favorable changes in PSA doubling time were again observed, and tended to be greatest in patients with evidence of long-term immunity [31]. The findings from both of the trials above have provided the rationale for a randomized phase II clinical trial evaluating this same DNA vaccine to determine whether vaccination prolongs time to disease progression, a multicenter trial that is currently underway (NCT01341652).

In some embodiments, the DNA vaccine technology (e.g., relating to compositions, methods, etc.) is as described in U.S. Pat. App. Pub. No. 20040142890 A1, which is explicitly incorporated herein by reference in its entirety.

PD-1 Pathway Inhibitor

In some embodiments, the PD-1 pathway inhibitor is a monoclonal antibody.

In some embodiments, the monoclonal antibody is pembrolizumab (marketed under the trade name "Keytruda®"). Pembrolizumab is a human programmed death receptor-1 (PD-1)-blocking antibody indicated for the treatment of patients with unresectable or metastatic melanoma and disease progression following ipilimumab and, if BRAF V600 mutation positive, a BRAF inhibitor. Accordingly, in some embodiments the same dose and schedule is used as has been used for the approved melanoma indication. For example, in some embodiments pembrolizumab is administered at 2 mg/kg (rounded to the nearest 50 mg) as an intravenous infusion over 30 minutes every 3 weeks (up to four maximum doses). Pembrolizumab is available in single-use vials, consisting of 50 mg lyophilized powder for injection. It is prepared by addition of 2.3 mL of sterile water for injection, USP, to the vial to prepare a 25 mg/mL solution. In some embodiments, it is transferred to an IV bag containing 0.9% sodium chloride injection, USP such that the final concentration of the diluted solution is between 1 mg/mL and 10 mg/mL. Accordingly, in some embodiments it is administered as an intravenous infusion, e.g., over 30 minutes using an IV line containing a sterile, non-pyrogenic, low-protein binding 0.2 µm to 5 µm in-line or add-on filter.

In some embodiments, the monoclonal antibody is nivolumab (marketed under the trade name "Opdivo®"). Nivolumab is a human IgG4 anti-PD-1 monoclonal antibody that acts as an immunomodulator by blocking ligand activation of the programmed cell death 1 (PD-1) receptor on activated T cells. In particular, nivolumab acts by blocking a negative regulator of T-cell activation and response, thus allowing the immune system to attack the tumor. That is, nivolumab blocks PD-L1 from binding to PD-1, allowing the T cell to function in tumor attack.

The present invention also contemplates the use of other PD-1 antagonists in the methods and kits of the present invention, including, but not limited to: BMS-936559 (Bristol-Myers Squibb); MEDI0680 (Medlmmune/AstraZeneca); MEDI4736 (Medlmmune/AstraZeneca); MPDL3280A (Genentech/Roche), MSB0010718C (EMD Serono); and Pidilizumab (CureTech).

DNA Vaccines

DNA vaccines, like peptide-based vaccines, are advantageous in being relatively easy and inexpensive to manufacture, and are not individualized for patients, as are dendritic cell-based vaccines. Unlike recombinant protein vaccines, in which the antigen is taken up by antigen presenting cells and expressed predominantly in the context of MHC class II, DNA in nucleic acid vaccines is taken up and expressed by antigen-presenting cells directly, leading to antigen presentation through both naturally processed MHC class I and II epitopes [38].

The present technology provides DNA-based vaccines that express a protein antigen, prostatic acid phosphatase (PAP), and methods for treating prostate cancers in an animal using the vaccines in combination with a PD-1 inhibitor. PAP genes are known and have been cloned from human, mouse, and rat (see, e.g., SEQ ID NO: 1, SEQ ID NO: 2, and SEQ ID NO: 3, respectively). As will be readily recognized by one of ordinary skill in the art, any DNA sequence that encodes a PAP gene is suitable for the present invention, and any other PAP genes from other animals, as they become identified, characterized, and cloned are also suitable for the present invention. Dogs and non-human primates are known to have PAP genes. It is readily recognizable that a PAP gene of any origin, or any of its derivatives, equivalents, variants, mutants etc., is suitable for the instant technology, as long as the protein encoded by the genes, or derivatives, equivalents, variants, or mutants thereof induce an immune reaction in the host animal substantially similar to that induced by an autoantigenic or xenoantigenic PAP protein in the animal.

In some embodiments, the derivatives, equivalents, variants, fragments, or mutants of a PAP polypeptide are at least 85% identical in sequence to the human PAP sequence of SEQ ID NO:1. More preferably, the identity is at least 88%, preferably at least 90%, still more preferably at least 95%, and still more preferably at least 95%. Identity between amino acid sequences or between nucleotide sequences may be determined either manually by one skilled in the art, or by using computer-based sequence comparison and identification tools that employ algorithms such as BLAST (Basic Local Alignment Search Tool; Altschul et al. (1993) J. Mol. Biol. 215:403-410).

In some embodiments, fragments of the full-length genes which encode portions of the full-length PAP protein are constructed. These fragments peptides that elicits humoral or cytotoxic reaction, or both, against the protein antigen, and are considered functional equivalents.

In some embodiments, the PAP gene is ligated into an expression vector that has been specifically optimized for polynucleotide vaccinations. Features of a suitable expression vector include, e.g., a transcriptional promoter, immunogenic epitopes, immunostimulatory sequences, and additional cistrons encoding immunoenhancing or immunomodulatory genes, with their own promoters, transcriptional terminators, bacterial origin of replication, and antibiotic resistance genes, as well known to those skilled in the art. Optionally, in some embodiments the vector contains internal ribosome entry sites (IRES) for the expression of polycistronic mRNA.

In some embodiments of the technology, a gene encoding a PAP protein is directly linked to a transcriptional promoter. In some embodiments, a tissue-specific promoter or enhancer (e.g., the muscle creatine kinase (MCK) enhancer element) finds use to limit expression of the polynucleotide to a particular tissue type. For example, myocytes are terminally differentiated cells that do not divide. Integration of foreign DNA into chromosomes appears to be promoted by both cell division and protein synthesis. Thus, limiting protein expression to non-dividing cells such as myocytes may be preferable. In addition, in some embodiments a PSA promoter is used to limit expression of the protein to prostate tissue. In some embodiments, tissue-specific or cell-specific promoters are used to target the expression of the protein to antigen-presenting cells. For example, in some embodiments an alpha-fetoprotein (AFP) promoter (see e.g. Peyton et al. 2000, Proc. Natl. Acad. Sci., USA. 97:10890-10894) is used to limit expression to liver tissues. However, use of the CMV promoter is adequate for achieving expression in many tissues into which the plasmid DNA vaccine is introduced.

In various embodiments, suitable vectors include any plasmid DNA construct encoding a PAP antigen or a functional equivalent or derivative thereof, operatively linked to a eukaryotic promoter. Examples of such vectors include the pCMV series of expression vectors, commercially available from Stratagene (La Jolla, Calif.); or the pCDNA or pREP series of expression vectors by Invitrogen Corporation (Carlsbad, Calif.).

There are many embodiments of the instant invention that those skilled in the art can appreciate from the specification. Thus, in the various embodiments different transcriptional promoters, terminators, and other transcriptional regulatory elements are used. Examples of other eukaryotic transcription promoters include the Rous sarcoma virus (RSV) promoter, the simian virus 40 (SV40) promoter, the human elongation factor-1 alpha (EF-1 alpha) promoter, and the human ubiquitin C (UbC) promoter.

In some embodiments, "naked" plasmid DNA expressing a transgene finds use, e.g., in some embodiments the naked plasmid DNA is directly injected intradermally or intramuscularly, taken up, and expressed (see e.g. Wolff et al., 1990, Science 247:1465-8). The efficiency of this approach may be low, with only a small percentage of myocytes being directly transformed in vivo, and within only a limited area of muscle tissue targeted by this directed delivery. Various alternative approaches yielding a higher efficiency gene delivery method are known (see e.g. Acsadi et al., 1991, New Biol. 3:71-81; Wolff et. al., 1991, Biotechniques 11:474-85; Budker et. al., 1996, Nat. Biotechnol. 14:760-4; Davis et al., 1993, Hum. Gene Ther. 4:151-9; Danko et al., 1994, Gene Ther. 1:114-21; Manthorpe et al., 1993, Hum. Gene Ther. 4:419-31).

In some embodiments, the DNA vaccine is pTVG-HP (e.g., pTVG4 vector containing cDNA for human PAP). pTVG-HP is a plasmid DNA, produced in E. coli, that encodes the cDNA for human prostatic acid phosphatase (PAP). In particular, the pTVG-HP plasmid was constructed from the plasmid vector pNGVL3 (e.g., as obtained from the National Gene Vector Laboratory at the University of Michigan). This vector, similar to the pCDNA3.1 expression vector, drives transcription from the CMV promoter, but also includes the CMV intron A sequence to enhance protein expression (Lee et al., 1997, Mol. Cells 7:495-501). The vector also contains a multi-cloning site, and does not express a eukaryotic antibiotic resistance gene, such that the only protein expression expected in a eukaryotic system is the one driven from the CMV promoter, unlike the pCDNA vector. To this vector has been added 2 copies of a 36-bp immunostimulatory (ISS) fragment containing the 5'-GTCGTT-3' motif previously identified (Hartmann et al., 2000, J. Immunol. 164:1617-24) (e.g., a polynucleotide comprising a TpC dinucleotide at the 5' end followed by three 6-mer CpG motifs (5'-GTCGTT-3') separated by TpT dinucleotides), to create the vector pTVG4. The coding sequence for human PAP was cloned into this vector, and expression of PAP was confirmed by in vitro expression studies. This construct is named pTVG-HP. Thus, in some embodiments the DNA vaccine comprises CpG immunostimulatory sequences. In some embodiments, the immunostimulatory sequence is TCG TCG TTT TGT CGT TTT GTC GTT (SEQ ID NO: 4).

As described above, the cDNA coding sequence for human PAP was cloned into pTVG to produce the construct pTVG-HP. Transient transfection of Chinese Hamster Ovary (CHO) cells followed by capture ELISA confirmed that PAP is expressed in vitro. In addition, PAP is expressed in vivo and produces an immunological response in humans. See, e.g., U.S. Pat. App. Pub. No. 20040142890 A1, which is expressly incorporated herein by reference, e.g., in the examples.

The sequence of the pTVG-HP DNA obtained from the master cell bank bacterial strain expressing the vaccine is confirmed by standard DNA sequencing. The biological activity of each vaccine lot is tested in rodent studies demonstrating that T-cell immune responses specific for PAP are elicited in vivo following immunization. Lots are tested for appearance, plasmid homogeneity, DNA identity by restriction endonuclease evaluation, protein contamination, RNA contamination, genomic DNA contamination, sterility, endotoxin, and pH, and criteria for each of these have been established for lot release. In some embodiments, the vaccine is supplied in single-use vials containing 0.6 mL 0.2 mg/mL pTVG-HP in phosphate-buffered saline. Vials ale stored at −80° C. until the day of use.

GM-CSF

GM-CSF (Leukine®, Sargramostim) is a vaccine adjuvant. In particular, GM-CSF is a growth factor that supports the survival, clonal expansion and differentiation of hematopoietic progenitor cells including dendritic antigen presenting cells. GM-CSF has been shown to be safe and serve as an effective adjuvant for the induction of antibody and T-cell responses to the immunized antigen [58, 59]. The use of GM-CSF is associated with little toxicity [60, 61, 62]. GM-CSF is a sterile, white, preservative-free, lyophilized powder supplied in 250 μg-dose vials. Recombinant human GM-CSF (rhGM-CSF), when administered intravenously or subcutaneously is generally well tolerated at doses ranging from 50 to 500 µg/m2/day.

In specific embodiments of the technology, vials are thawed and the plasmid DNA vaccine is used to reconstitute the GM-CSF. For example, for each DNA immunization, 0.6 mL of 0.2 mg/mL pTVG-HP is withdrawn and used to reconstitute 250 µg GM-CSF. 0.25 mL is then drawn into each of two tuberculin syringes. This effectively provides a 100-µg dose of DNA and 208 µg GM-CSF.

Combination Vaccine Technology

Previous results indicated no objective disease response in patients treated with PD-1 blockade alone; and data collected during the development of embodiments of the technology demonstrated that in a similar murine model of tumor cells that express PD-L1 there was no evidence of tumor growth delay or eradication unless PD pathway blockade was combined with tumor antigen-specific vaccination.

Accordingly, some embodiments of the technology provided herein relate to use of: 1) a plasmid DNA vaccine encoding PAP (e.g., pTVG-HP) to induce and/or augment therapeutic T-cells specific for the prostate tumor antigen PAP in patients with castrate-resistant, metastatic prostate cancer; and 2) a PD pathway inhibitor (e.g., pembrolizumab or nivolumab). In some embodiments, the DNA vaccine is administered concurrently with the PD pathway inhibitor as discussed herein (see, e.g., dosing schedules described in detail herein). In some embodiments, the DNA vaccine is administered prior to treatment with the PD pathway inhibitor (see, e.g., dosing schedules described in detail herein).

It is further contemplated that identifying (e.g., detecting) antigen-specific PD-1-regulated T-cells is predictive for response to combined treatment.

Thus, some embodiments of the technology relate to administering pembrolizumab or nivolumab in combination (e.g., concurrently or sequentially) with pTVG-HP in cancer patients (e.g., patients with castration-resistant, metastatic prostate cancer). Some embodiments relate to compositions comprising pembrolizumab and pTVG-HP; some embodiments relate to kits comprising pembrolizumab or nivolumab and pTVG-HP.

In some embodiments, patients are tested before and/or after administration of the DNA vaccine (e.g., pTVG-HP). In some embodiments, patients are tested before and/or after administration of the PD pathway inhibitor (e.g., pembrolizumab or nivolumab). In some embodiments, testing comprises, e.g., imaging methods (e.g., radiographic methods, bone imaging), measuring anti-tumor response rates (objective response rate and/or PSA response rate, using PCWG2 criteria), measuring the magnitude of PAP-specific T-cell responses, measuring PD-1 expression on circulating T cells, measuring PD-L1 expression on circulating epithelial cells (CEC) and/or on tumor biopsies, measuring tumor growth rates, measuring the amounts of PAP-specific antibodies, measuring the amounts of prostate-associated antigens (e.g., PSA and/or PAP).

In some embodiments, biomarkers are monitored, e.g., to follow the course of treatment and/or as predictors of the efficacy of treatment. Exemplary biomarkers include PD-L1 expression on CEC or tumor biopsies, expression of other regulatory molecules on tumor-specific T cells (e.g. TIM3, BTLA, and LAG3) or tumor cells (e.g. HVEM, phosphatidyl serine, PD-L2), and PD-1-regulated antigen-specific T cells (e.g., identified by trans vivo DTH testing).

Pharmaceutical Formulations

It is generally contemplated that the DNA vaccine and PD-1 inhibitor are formulated for administration to a mammal, and especially to a human with a condition that is responsive to the administration of such compounds (e.g., a human subject having a prostate cancer). Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents.

With respect to administration to a subject, it is contemplated that the compounds be administered in a pharmaceutically effective amount. One of ordinary skill in the art recognizes that a pharmaceutically effective amount varies depending on the therapeutic agent used, the subject's age, condition, and sex, and on the extent of the disease in the subject. Generally, the dosage should not be so large as to cause adverse side effects, such as hematological problems, pulmonary problems, colitis, hepatitis, nephritis, hypophisitis, impaired thyroid function, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Accordingly, in some embodiments, the immunotherapeutic agent is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a transdermal dissolvable microneedle formulation (e.g., provided in a patch); a sterile solution; a sterile solution prepared for use as an intramuscular, intradermal, or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the compound over time.

In some embodiments, the compositions are formulated so that the active ingredient is embedded in a matrix of an insoluble substance (e.g., various acrylics, chitin) such that the dissolving compound finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the compound dissolves into the matrix and the matrix physically swells to form a gel, allowing the compound to exit through the gel's outer surface. In some embodiments, the formulations are in a micro-encapsulated form, e.g., which is used in some embodiments to produce a complex dissolution profile. For example, by coating the compound around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein means nano- or microparticles (or in some instances larger) that can consist in whole or in part of the compounds as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, non-erodible, biodegradable, or nonbiodegradable materials or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of the compounds or salts thereof to inhibit formation of degradation products. A solution is provided that contains the compound or salts thereof and at least one inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the compound is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the compound is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate.

Still other chelating agents include niacinamide and derivatives thereof and sodium desoxycholate and derivatives thereof.

In some embodiments, the compound is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compound is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the compound is formulated with an isotonicity agent. The isotonicity agent can be any pharmaceutically acceptable isotonicity agent. This term is used in the art interchangeably with isoosmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the compound is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Methods of Measurement and Assays

In various embodiments, data are collected using various techniques and observables, e.g., to measure a baseline for a subject and/or to monitor the efficacy of a treatment. For instance, some embodiments comprise imaging-based evaluation of a subject. In some particular embodiments, imaging techniques comprise computed tomography (CT). In some particular embodiments, imaging techniques comprise magnetic resonance imaging (MRI). In some embodiments, CT and/or MRI provide accurate and reproducible methods for measuring target lesions. In some embodiments, CT and MRI are performed with contiguous cuts of 10 mm or less in slice thickness. In some embodiments, spiral CT is performed using a 5 mm contiguous reconstruction algorithm, e.g., for tumors of the chest, abdomen, and pelvis.

In some embodiments, a tumor marker is measured. For example, in some embodiments PSA is measured. In some embodiments, PSA values are collected for separate reporting of PSA kinetics. In some embodiments, a value of PSA that declines to <0.2 ng/mL for a subject indicates a complete clinical response when all tumor lesions have disappeared. In some embodiments, serum PAP is measured. In some embodiments, serum concentrations of PAP and/or PSA stabilize after vaccination and/or decline after vaccination and provide a measurement of vaccine efficacy. In some embodiments, the ratio of serum PSA to serum PAP is calculated and provides a measure of vaccine efficacy. Without being bound by theory and with an understanding that an understanding of the mechanism or theory is not required to practice the technology, in some embodiments the PSA:PAP ratio increases with therapy because therapy selectively depletes PAP-producing cells relative to PSA-producing cells, thus causing PAP concentrations to fall faster than PSA concentrations.

In some embodiments, a clinical examination is performed on a subject. In some embodiments, a clinically detected lesion is considered measurable when it is superficial (e.g., skin nodules and palpable lymph nodes). In some embodiments, skin lesions are documented by color photography, including a ruler to estimate size of the lesion.

Histopathology Evaluation

In some embodiments, tissue biopsies are obtained from metastatic lesions (e.g., the same lesion per patient) prior to treatment and after treatment (e.g., from 1 to 20 weeks after treatment is initiated, e.g., during week 1, 2, 3, 4, 5, 6, 7, 8, 9, 10, 11, 12, 13, 14, 14, 16, 17, 18, 19, or 20). In some embodiments, tests are performed to evaluate how immunization affects PD-L1 expression in the tumor. Without being bound by theory and acknowledging that an understanding of the mechanism is not required to practice the technology, it is contemplated that immunization affects PD-L1 expression in the tumor by eliciting tumor antigen-specific T cells secreting IFNγ. Furthermore, tests are performed to assess whether concurrent treatment with anti-PD-1 mAb leads to an increase in infiltration of CD8+ T cells and whether treatment increases expression of other T-cell regulatory ligands on T cells (PD-1, CTLA-4, TIM-3, BTLA, LAG-3) or tumors (e.g. HVEM, phosphatidyl serine, PD-L2). Consequently, biopsy specimens obtained pre-treatment and after initiation of treatment are stained with antibodies specific for CD3, CD4, CD8, FoxP3, PD-1, CTLA-4, TIM3, BTLA, LAG-3, PD-L1, PD-L2, phosphatidyl serine, and/or HVEM, and/or other markers. Staining and quantification are reviewed by a pathologist blinded to the treatment groups to determine CD8+ T cells per field, CD4+FoxP3+ (Treg):CD8+ T cell ratio, PD-L1 expression (e.g., as indicated by at least 5 PD-L1 positive cells per field), and to compare these parameters measured before and after treatment to identify any of these measured or calculated parameters that changed as a result of treatment.

Circulating Tumor Cell (CTC) Evaluation

In some embodiments, CTC are enumerated and characterized, e.g., in some embodiments, at the same time points as for immune evaluation (e.g., pre-treatment, after 1 to 6 weeks (e.g., after 1, 2, 3, 4, 5, or 6 weeks), and at intervals for up to one year (e.g., monthly, quarterly) using flow cytometry. For example, in some embodiments PBMC obtained at these time points are stained, e.g., with fluorochrome-labeled antibodies specific for at least one or more of CD45, EpCAM, PD-1, PD-L1, CTLA-4, and DAPI. CTC are defined as CD45−EpCAM+DAPI− cells, and the percentage of these events among all live cellular events are determined at the different time points. The percentages of CTC expressing PD-1, PD-L1, or CTLA-4 are also determined. Results are reported from the different time points and general trends are assessed. In some embodiments, results quantitative and in some embodiments results are qualitative (e.g., in some embodiments, obtaining multiple replicates to determine standard deviation are not feasible). The technology encompasses other methods of CTC capture and enumeration.

Subjects

In some embodiments, the combination therapy is administered to a subject. For example, in some embodiments, the subject is a cancer patient, e.g., a prostate cancer patient, e.g., a patient having with castrate-resistant, metastatic prostate cancer. In some embodiments, the subject is an adult (e.g., is aged 18 years or more). In some embodiments, the subject has prostate cancer that has been confirmed by histology. In some embodiments, the subject has metastatic disease, e.g., the presence of soft tissue and/or bone metastases (e.g., as detected by imaging (CT (e.g., of abdomen/pelvis), bone scintigraphy, etc.)). In some embodiments, the subject has castrate-resistant disease, e.g., in some embodiments, subjects have received androgen deprivation treatment (e.g., surgical castration, GnRH analogue, or antagonist treatment). In some embodiments, subjects receive a GnRH analogue or antagonist during treatment with the combination therapy (e.g., DNA vaccine and PD-1 inhibitor) described herein. In some embodiments, subjects have been treated previously with a nonsteroidal antiandrogen; in some embodiments, subjects have not been treated previously with a nonsteroidal antiandrogen. In some embodiments in which subjects have been previously treated with an antiandrogen, the subjects have discontinued use of anti-androgen for at least 4 weeks (for flutamide) or 6 weeks (for bicalutamide or nilutamide) prior to treatment with the combination therapy described herein. Moreover, in some embodiments, PSA is monitored in subjects, e.g., for subjects who demonstrated an anti-androgen withdrawal response (e.g., a >25% decline in PSA within 4-6 week of stopping a nonsteroidal antiandrogen), the combination therapy described herein is administered when the subject PSA rises above the nadir observed after antiandrogen withdrawal. In some embodiments, the castration level of testosterone is <50 ng/dL within 6 weeks the beginning of treatment.

In some embodiments, subjects are characterized by having progressive disease while receiving androgen deprivation therapy defined by any one of the following as per the Prostate Cancer Clinical Trials Working Group 2 (PCWG2) criteria [64]: a) at least two consecutive rises in serum PSA, obtained at a minimum of 1-week intervals, with the final PSA value >2.0 ng/mL; b) >50% increase in the sum of the cross products of all measurable lesions or the development of new measurable lesions (the diameter of a target lymph node must be at least 2.0 cm by CT to be considered a target lesion); or the appearance of two or more new areas of uptake on bone scan consistent with metastatic disease compared to previous imaging during castration therapy (the increased uptake of pre-existing lesions on bone scan will not be taken to constitute progression, and ambiguous results must be confirmed by other imaging modalities (e.g. X-ray, CT, MRI, PET (e.g., $^{18}$F NaF PET), SPECT, etc.)).

In some embodiments, subjects have been previously treated with abiraterone or enzalutamide and, in some embodiments, subjects have been off (e.g., discontinued) prior corticosteroid treatment for at least 3 months. In some embodiments, subjects have an ECOG performance status of 0, 1, or 2. In some embodiments, subjects have adequate hematologic, renal, and liver function (e.g., WBC>2000/mm$^3$; ANC>1000/mm$^3$; HgB>9.0 gm/dL; platelets >100,000/mm$^3$; creatinine <2.0 mg/dL; and/or AST, ALT<2.5× institutional upper limit of normal). In some embodiments, subjects have no history of HIV 1 and 2, HTLV-1, or active Hepatitis B or Hepatitis C. In some embodiments, subjects have not had other treatments for at least 4 weeks and have recovered (to <Grade 2) from acute toxicity attributed to prior treatment. In some embodiments, subjects have had a biopsy.

As described below, a "level" of a biomarker (e.g., PD-1, PD-L1, etc.) or a "level of expression" of a biomarker (e.g., PD-1, PD-L1, etc.) is described as useful according to embodiments of the technology. In some embodiments, a "level" is determined, e.g., by enumerating a number of cells expressing a particular biomarker, by calculating a number of cells expressing a particular biomarker relative to another cell population (e.g., all cells, all cells in a microscope field, all live cells, PBMCs, epithelial cells, or any other cell population, etc.), or the number or concentration (e.g., average number or concentration) of a particular biomarker expressed (e.g., per-cell) on the cell surface.

In some embodiments, the subject has a low level of PD-1 and/or PD-L1 expression. As used herein, a "low level of expression" (e.g., a "low level of PD-1 expression" and/or "low level of PD-L1 expression") refers to a level (e.g., amount, number, concentration) of PD-1 that is one of the following: less than the level of PD-1 in a patient who has not received the DNA vaccine; less than the level of PD-1 in a subject that provides for an effective treatment of the subject with the PD-1 and/or PD-L1 inhibitor; and/or less than the level (e.g., amount, number, concentration) of PD-1 that is within the target range of PD-1; or refers to a level (e.g., amount, number, concentration) of PD-L1 that is one of the following: less than the level of PD-L1 in a patient who has not received the DNA vaccine; less than the level of PD-L1 in a subject that provides for an effective treatment of the subject with the PD-1 and/or PD-L1 inhibitor; and/or less than the level (e.g., amount, number, concentration) of PD-L1 that is within the target range of PD-L1 (see below).

In some embodiments, the subject has a level of PD-1 that is lower than a target range of PD-1. Accordingly, in some embodiments the subject has a level of PD-1 (e.g., a level of PD-1 that is normal) that is in need of being increased to a target range according to the technology provided herein. For example, in some embodiments the PD-1 inhibitor administered to the subject is effective when administered to a subject having a PD-1 level that is within the target range.

In some embodiments, the subject has a level of PD-L1 that is lower than a target range of PD-L1. Accordingly, in some embodiments the subject has a level of PD-L1 (e.g., a level of PD-L1 that is normal) that is in need of being increased to a target range according to the technology provided herein. For example, in some embodiments the PD-L1 inhibitor administered to the subject is effective when administered to a subject having a PD-L1 level that is within the target range.

Accordingly, in some embodiments a subject (e.g., a sample from a subject) is tested to measure a level of PD-1 and/or PD-L1 in the subject. Such testing is performed, e.g., by assaying or measuring a biomarker, a metabolite, a physical symptom, an indication, etc., to measure an amount, concentration, number, etc. of PD-1 and/or PD-L1 in the subject or in a sample from the subject. In some embodiments, a subject's PD-1 and/or PD-L1 level is measured by an immunohistochemical method (e.g., using an antibody that specifically binds to PD-1, using an antibody that specifically binds to PD-L1). In some embodiments, a subject's PD-1 and/or PD-L1 level is measured by a hybridization method, e.g., using a labeled nucleic acid probe to measure the level of mRNA encoding PD-1 and/or PD-L1. In some embodiments, a subject's PD-1 and/or PD-L1 level is tested prior to administration of the DNA vaccine described herein. In some embodiments, a subject's PD-1 and/or PD-L1 level is tested after administration of the DNA vaccine described herein.

In some embodiments, methods comprise administration of the DNA vaccine to increase the level of PD-1 in a subject. Some embodiments of methods comprise testing a subject to measure the subject's PD-1 level and administering the DNA vaccine to increase the subject's PD-1 level. Some embodiments of methods comprise testing a subject to measure the subject's PD-1 level prior to administering the DNA vaccine, administering the DNA vaccine to increase the subject's PD-1 level, and testing the subject after administering the DNA vaccine to measure the subject's PD-1 level. In some embodiments, a subject is treated with a DNA vaccine, a sample is obtained from the subject and the level of PD-1 is measured, the subject is treated again with the DNA vaccine based on the level of PD-1 that was measured, and then another sample is obtained and the level of PD-1 is measured. In some embodiments, other tests (e.g., not based on measuring the level of PD-1) are also used at various stages, e.g., before the initial treatment with a DNA vaccine, e.g., to provide a guide for the initial dose and/or dosing schedule of the DNA vaccine. Accordingly, in some embodiments, the dose and/or dosing schedule of the DNA vaccine is adjusted based on one or more measured amounts of PD-1 measured for the subject prior to administration of the DNA vaccine. In some embodiments, a subsequent treatment with the DNA vaccine is adjusted based on a test result, e.g., the dosage amount and/or dosage schedule of the DNA vaccine is changed. In some embodiments, a subsequent treatment with the DNA vaccine is adjusted based on a test result, e.g., a test result that antigen-specific cells were responsive to PD-1 blockade.

In some embodiments, a patient's PD-1 level is measured, the DNA vaccine is administered to the subject, and then the PD-1 level is measured again to monitor the response of the subject to the DNA vaccine and/or to change the dosage amount or dosage schedule of the DNA vaccine. In some embodiments, cycles of measuring and administering occur without limitation to the pattern of measuring and administering, the periodicity, or the duration of the interval between each measuring and administering phase. As such, the technology contemplates various combinations of measuring the PD-1 level and administering the DNA vaccine without limitation, e.g., measure/administer, administer/measure, measure/administer/measure, administer/measure/administer, measure/administer/measure/administer, measure/administer/measure/administer/measure, measure/administer/measure/measure/administer/administer/ administer/measure, administer/administer/measure/administer, measure/administer/administer/measure/administer/administer, etc.

For instance, cycles of measuring PD-1 and administering the DNA vaccine can be used to increase the subject's PD-1 level to a target range. In some embodiments, an initial measured value of a subject's PD-1 level indicates the dose of the DNA vaccine to administer to the subject to increase the subject's PD-1 level to the target range. In some embodiments, the subject's PD-1 level is measured after administration of one or more doses of the DNA vaccine, e.g., to confirm that the subject's PD-1 level is within the target range. In some embodiments, the target range is a general range for all subjects (e.g., for all prostate cancer patients) and in some embodiments the target range is determined on an individualized basis for each subject.

In some embodiments, testing comprises testing for a response to PD-1 blockade (e.g., rather than testing for an increase or decrease in PD-1 expression). For example, in some embodiments, testing comprises testing cells in vitro for a PAP-specific response (e.g., IFN gamma secretion) in the presence of a PD-1 blockade. In some embodiments, testing comprises a footpad delayed type hypersensitivity assay.

In some embodiments, methods comprise administration of the DNA vaccine to increase the level of PD-L1 in a subject. Some embodiments of methods comprise testing a subject to measure the subject's PD-L1 level and administering the DNA vaccine to increase the subject's PD-L1 level. Some embodiments of methods comprise testing a subject to measure the subject's PD-L1 level prior to administering the DNA vaccine, administering the DNA vaccine to increase the subject's PD-L1 level, and testing the subject after administering the DNA vaccine to measure the subject's PD-L1 level. In some embodiments, a subject is treated with a DNA vaccine, a sample is obtained from the subject and the level of PD-L1 is measured, the subject is treated again with the DNA vaccine based on the level of PD-L1 that was measured, and then another sample is obtained and the level of PD-L1 is measured. In some embodiments, other tests (e.g., not based on measuring the level of PD-L1) are also used at various stages, e.g., before the initial treatment with a DNA vaccine, e.g., to provide a guide for the initial dose of the DNA vaccine. Accordingly, in some embodiments, the dose of the DNA vaccine is adjusted based on one or more measured amounts of PD-L1 measured for the subject prior to administration of the DNA vaccine. In some embodiments, a subsequent treatment with the DNA vaccine is adjusted based on a test result, e.g., the dosage amount or dosage schedule of the DNA vaccine is changed. In some embodiments, a subsequent treatment with the DNA vaccine is adjusted based on a test result, e.g., a test result that antigen-specific cells were responsive to PD-L1 blockade.

In some embodiments, a patient's PD-L1 level is measured, the DNA vaccine is administered to the subject, and then the PD-L1 level is measured again to monitor the response of the subject to the DNA vaccine and/or to change the dosage amount or dosage schedule of the DNA vaccine. In some embodiments, cycles of measuring and administering occur without limitation to the pattern of measuring and administering, the periodicity, or the duration of the interval between each measuring and administering phase. As such, the technology contemplates various combinations of measuring the PD-L1 level and administering the DNA vaccine without limitation, e.g., measure/administer, administer/measure, measure/administer/measure, administer/measure/administer, measure/administer/measure/administer, measure/administer/measure/administer/measure, measure/administer/measure/measure/administer/administer/ administer/measure, administer/administer/measure/ administer, measure/administer/administer/measure/ administer/administer, etc.

For instance, cycles of measuring PD-L1 and administering the DNA vaccine can be used to increase the subject's PD-L1 level to a target range. In some embodiments, an initial measured value of a subject's PD-L1 level indicates the dose of the DNA vaccine to administer to the subject to increase the subject's PD-L1 level to the target range. In some embodiments, the subject's PD-L1 level is measured after administration of one or more doses of the DNA vaccine, e.g., to confirm that the subject's PD-L1 level is within the target range. In some embodiments, the target range is a general range for all subjects (e.g., for all prostate cancer patients) and in some embodiments the target range is determined on an individualized basis for each subject.

In some embodiments, testing comprises testing for a response to PD-L1 blockade (e.g., rather than testing for an increase or decrease in PD-L1 expression). For example, in some embodiments, testing comprises testing cells in vitro for a PAP-specific response (e.g., IFN gamma secretion) in the presence of a PD-L1 blockade. In some embodiments, testing comprises a footpad delayed type hypersensitivity assay.

Administration, Treatments, Dosages, and Dosing Schedules

In some embodiments, the technology relates to methods of administering a DNA vaccine and a PD-1 inhibitor to a subject. In some embodiments, the technology relates to methods of administering a DNA vaccine and a PD-L1 inhibitor to a subject. The methods comprise the general steps of administering a DNA vaccine and a PD-1 inhibitor to a subject according to the technology. In some embodiments, a DNA vaccine and/or a PD-1 inhibitor, a derivative thereof, or a pharmaceutically acceptable salt thereof, is administered in a pharmaceutically effective amount. In some embodiments, a DNA vaccine and/or a PD-1 inhibitor, a derivative thereof, or a pharmaceutically acceptable salt thereof, is administered in a therapeutically effective dose.

The dosage amount and frequency are selected to create an effective level of the compound without substantially harmful effects. When administered orally, intradermally, transdermally, or intravenously, the dosage of the DNA vaccine and/or a PD-1 inhibitor will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrasternal injection, intravenous, intradermal, and infusion routes. In some embodiments, the compound, a derivative thereof, or a pharmaceutically acceptable salt thereof, is administered orally.

In some embodiments, a single dose of a compound or a related compound is administered to a subject. In other embodiments, multiple doses are administered over two or more time points, separated by hours, days, weeks, etc. In some embodiments, compounds are administered over a long period of time (e.g., chronically), for example, for a period of weeks, months, or years (e.g., 1, 2, 3, 4, 5, 6, 7, 8, 9, 10, 11, 12, or more weeks, months, or years). In such embodiments, compounds may be taken on a regular scheduled basis (e.g., daily, weekly, fortnightly, etc.) for the duration of the extended period.

The technology also relates to methods of treating a subject with a DNA vaccine and a PD-1 inhibitor. According to another aspect of the technology, a method is provided for treating a subject in need of such treatment with an effective amount of a DNA vaccine and/or a PD-1 inhibitor or one or more salts thereof. The method involves administering to the subject an effective amount of a DNA vaccine and/or a PD-1 inhibitor or a salt thereof in any one of the pharmaceutical preparations described above, detailed herein, and/or set forth in the claims. The subject can be any subject in need of such treatment. In the foregoing description, the technology is in connection with a compound or salts thereof. Such salts include, but are not limited to, bromide salts, chloride salts, iodide salts, carbonate salts, and sulfate salts. It should be understood, however, that the compound is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "compound" appears.

In some embodiments, a subject is tested to assess the presence, the absence, or the level of a malady and/or a condition such as prostate cancer. Such testing is performed, e.g., by assaying or measuring a biomarker, a metabolite, a physical symptom, an indication, etc., to determine the risk of or the presence of the malady or condition. In some embodiments, the subject is treated with a DNA vaccine and/or a PD-1 inhibitor based on the outcome of the test. In some embodiments, a subject is treated with a DNA vaccine and/or a PD-1 inhibitor, a sample is obtained, and the level of detectable agent is measured, and then the subject is treated again with a DNA vaccine and/or a PD-1 inhibitor based on the level of detectable agent that was measured. In some embodiments, a subject is treated with a DNA vaccine and/or a PD-1 inhibitor, a sample is obtained and the level of detectable agent is measured, the subject is treated again with a DNA vaccine and/or a PD-1 inhibitor based on the level of detectable agent that was measured, and then another sample is obtained and the level of detectable agent is measured. In some embodiments, other tests (e.g., not based on measuring the level of detectable agent) are also used at various stages, e.g., before the initial treatment with a DNA vaccine and/or a PD-1 inhibitor as a guide for the initial dose. In some embodiments, a subsequent treatment with a DNA vaccine and/or a PD-1 inhibitor is adjusted based on a test result, e.g., the dosage amount, dosage schedule, identity of the drug, etc. is changed.

In some embodiments, a patient is tested, treated, and then tested again to monitor the response to therapy and/or change the therapy. In some embodiments, cycles of testing and treatment may occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/test/treat, test/treat/test/treat, test/treat/test/test/treat/treat/treat/test, treat/treat/test/treat, test/treat/treat/test/treat/treat, etc.

The technology is not limited in the dosing and dosing schedule used to administer the DNA vaccine and the PD-1 inhibitor. For example, in some embodiments the DNA vaccine (e.g., pTVG-HP (e.g., 100 µg) with rhGM-CSF (e.g., 208 µg)) is administered intradermally biweekly 6 times beginning at day 1 and the PD-1 inhibitor (e.g., pembrolizumab or nivolumab at 2 mg/kg) is administered intravenously every 3 weeks 4 times, beginning at day 1. In some embodiments, the DNA vaccine (e.g., pTVG-HP (e.g., 100 µg) with rhGM-CSF (e.g., 208 µg)) is administered intradermally biweekly 6 times beginning at day 1 and the PD-1 inhibitor (e.g., pembrolizumab or nivolumab at 2 mg/kg) is administered intravenously biweekly 6 times with the first dose being administered two weeks after the last pTVG-HP vaccination.

Thus, in some embodiments the DNA vaccine (e.g., pTVG-HP) is administered in an amount of approximately 100 µg (e.g., 10, 20, 30, 40, 50, 60, 70, 80, 90, 100, 110, 120, 130, 140, 150, 160, 170, 180, 190, 200, 300, 400, 500, 600, 700, 800, 900, or 1000 or more µg). In some embodiments, the DNA vaccine is administered in combination with an adjuvant, e.g., GM-CSF (e.g., rhGM-CSF), e.g., in an amount of approximately 200 µg (e.g., 100 to 500 µg, e.g., 100, 110, 120, 130, 140, 150, 160, 170, 180, 190, 200 (e.g., in some embodiments 208), 210, 220, 230, 240, 250, 260, 270, 280, 290, 300, 400, 500, 600, 700, 800, 900, or 1000 or more µg). As noted above, in some embodiments, the DNA vaccine is administered intradermally (e.g., on the deltoid area of the lateral arm). In some embodiments, the DNA vaccine is administered in a volume of approximately 0.25 mL (e.g., 100 to 500 µl, e.g., 100, 110, 120, 130, 140, 150, 160, 170, 180, 190, 200, 210, 220, 230, 240, 250, 260, 270, 280, 290, 300, 400, 500, 600, 700, 800, 900, or 1000 µl or more). In some embodiments, the volume of the DNA vaccine is administered at each of two adjacent sites. In some embodiments, the DNA vaccine is administered biweekly (e.g., approximately every two weeks, e.g., approximately every 14 days (e.g., 14±3 days (e.g., 11 to 17 days)). In some embodiments, the DNA vaccine is administered 6 times (e.g., 3 to 9 times, e.g., 3, 4, 5, 6, 7, 8, or 9 times).

Further, in some embodiments, the PD-1 pathway inhibitor (e.g., pembrolizumab or nivolumab) is administered at a dose of 2 mg/kg (e.g., 1 to 5 mg/kg, e.g., 1, 1.5, 2, 2.5, 3, 3.5, 4, 4.5, or 5 mg/kg). In some embodiments, the PD-1 pathway inhibitor is administered intravenously. In some embodiments, the PD-1 pathway inhibitor is administered (e.g., intravenously) over 30 minutes (e.g., from 15 minutes to 2 hours, e.g., for 15, 30, 45, 60, 75, 90, 105, or 120 minutes). In some embodiments, the PD-1 pathway inhibitor is administered every 3 weeks (e.g., every week, every 1.5 weeks, every 2 weeks, every 2.5 weeks, every 3 weeks (e.g., every 21±3 days (e.g., 18 to 24 days)), every 3.5 weeks, every 4 weeks, or every 5 weeks). In some embodiments, the PD-1 pathway inhibitor is administered 4 times (e.g., 2 to 9 times, e.g., 2, 3, 4, 5, 6, 7, 8, or 9 times). In some embodiments, the PD-1 pathway inhibitor is administered concurrently with the DNA vaccine, e.g., on Day 1 before, with, or after the first vaccination with the DNA vaccine. In some embodiments in which the PD-1 pathway inhibitor is administered concurrently with the DNA vaccine, the PD-1 pathway inhibitor is administered in a first composition and the DNA vaccine is administered in a second separate composition. In some embodiments in which the PD-1 pathway inhibitor is administered concurrently with the DNA vaccine, the PD-1 pathway inhibitor and the DNA vaccine are administered in the same composition. In another exemplary embodiment, the PD-1 pathway inhibitor is administered subsequently to the administration of the DNA vaccine, e.g., from 1, 2, 3, 4 or more weeks after the ultimate vaccination with the DNA vaccine.

In some embodiments, the technology comprises administering the DNA vaccine and the PD-1 pathway inhibitors according to a schedule. For example, in some embodiments a subject is administered the DNA vaccine (e.g., pTVG-HP) and the PD-1 pathway inhibitor on the same day to initiate treatment (e.g., "Day 1"), e.g., the PD-1 pathway inhibitor is administered from 0 to 0.5 to 5 hours and up to 24 hours after administration of the DNA vaccine. Then, in some embodiments, the DNA vaccine and/or the PD-1 inhibitor is/are administered on several subsequent days after initiation of the treatment. For example, in some embodiments the DNA vaccine is administered on Day 15 (e.g., 15±3 days (e.g., 12 to 18 days) after the Day 1 administration of the DNA vaccine and the PD-1 inhibitor), on Day 29 (e.g., 14±3 days (e.g., 11 to 17 days) after the Day 15 administration of the DNA vaccine), on Day 43 (e.g., 14±3 days (e.g., 11 to 17 days) after the Day 29 administration of the DNA vaccine), on Day 57 (e.g., 14±3 days (e.g., 11 to 17 days) after the Day 43 administration of the DNA vaccine), and on Day 71 (e.g., 14±3 days (e.g., 11 to 17 days) after the Day 57 administration of the DNA vaccine); and the PD-1 inhibitor is administered on Day 22 (e.g., 7±3 days (e.g., 4 to 10 days) after the Day 15 administration of the DNA vaccine), on Day 43 (e.g., 0 to 0.5 to 5 hours after the Day 43 administration of the DNA vaccine), and on Day 64 (e.g., 7±3 days (e.g., 4 to 10 days) after the Day 57 administration of the DNA vaccine).

In some preferred embodiments, the vaccine and the PD-1 inhibitor are administered a plurality of times in an overlapping administration schedule. In some embodiments, the first time the vaccine and the PD-1 inhibitor are administered concurrently (i.e., at day 1 of the treatment schedule within 24 hours of one another) and thereafter the vaccine is administered every 10 to 20 or 21, preferably about every 14 days and the PD-1 inhibitor is administered every 17 to 24 days, preferably about every 21 days for a period of up to 90 days. In some embodiments, the methods further comprise administering the vaccine every 10 to 20 or 21 days, preferably about every 14 days, and the PD-1 inhibitor every 17 to 24 days, preferably about every 21 days, for a period of from 91 days to 365 days. In some embodiments, patients that exhibit a decrease in PSA or tumor regression after 90 days are selected for the administration of the vaccine every 10 to 20 or 21 days and the PD-1 inhibitor every 17 to 24 days for a period of from 91 days to 365 days. In some embodiments, the methods further comprise administering the vaccine every 10 to 20 or 21 days, preferably about every 14 days, and the PD-1 inhibitor every 17 to 24 days, preferably about every 21 days, for a period of from 366 days to 730 days. In some embodiments, patients that exhibit a decrease in PSA or tumor regression after 365 days are selected for the administration of the vaccine every 10 to 20 or 21 days and the PD-1 inhibitor every 17 to 24 days for a period of from 366 days to 730 days. In some embodiments, the vaccine and the PD-1 inhibitor are administered in an overlapping schedule every 10 to 28 days, preferably every 10 to 20 or 21 days or 10 to 24 days, and most preferably about every 14 days or 21 days for a period of up to 90 days. In some embodiments, the methods further comprise administering the vaccine and the PD-1 inhibitor in an overlapping schedule every 10 to 28 days, preferably every 10 to 20 or 21 days or 10 to 24 days, and most preferably about every 14 days for a period of from 91 days to 365 days. In some embodiments, patients that exhibit a decrease in PSA or tumor regression after 90 days are selected for the administration of the vaccine and the PD-1 inhibitor in an overlapping schedule every 10 to 28 days, preferably every 10 to 20 or 21 days or 10 to 24 days, and most preferably about every 14 days for a period of from 91 days to 365 days. In some embodiments, the methods further comprise administering the vaccine and the PD-1 inhibitor in an overlapping schedule every 10 to 28 days, preferably every 10 to 20 or 21 days or 10 to 24 days, and most preferably about every 14 days for a period of from 366 days to 730 days. In some embodiments, patients that exhibit a decrease in PSA or tumor regression after 365 days are selected for the concurrent administration of the vaccine and the PD-1 inhibitor every 10 to 28 days, preferably every 10 to 20 or 21 days or 10 to 24 days, and most preferably about every 14 days for a period of from 366 days to 730 days. In some embodiments, the vaccine and PD-1 inhibitor are administered concurrently within the overlapping administration schedule. Concurrent administration encompasses administering the vaccine and the PD-1 inhibitor in the same composition (e.g., a solution), or where the agents are administered separately, administration in the same day and preferably administration within from about 1 minute to about 5 hours or 24 hours of one another or from about 30 minutes to about 5 hours or 24 hours of one another.

In other embodiments of the dosing schedule, a subject is administered the DNA vaccine (e.g., pTVG-HP) to initiate treatment (e.g., "Day 1") and is not administered the PD-1 inhibitor on Day 1. Then, the DNA vaccine and/or the PD-1 inhibitor is/are administered on several subsequent days after initiation of the treatment. For example, in some embodiments the DNA vaccine is administered on Day 15 (e.g., 15±3 days (e.g., 12 to 18 days) after the Day 1 administration of the DNA vaccine), on Day 29 (e.g., 14±3 days (e.g., 11 to 17 days) after the Day 15 administration of the DNA vaccine), on Day 43 (e.g., 14±3 days (e.g., 11 to 17 days) after the Day 29 administration of the DNA vaccine), on Day 57 (e.g., 14±3 days (e.g., 11 to 17 days) after the Day 43 administration of the DNA vaccine), and on Day 71 (e.g., 14±3 days (e.g., 11 to 17 days) after the Day 57 administration of the DNA vaccine); and the PD-1 inhibitor is administered after the series of administrations of the DNA vaccine, e.g., on Day 85 (e.g., 14±3 days (e.g., 11 to 17 days) after the Day 71 administration of the DNA vaccine), on Day 106 (e.g., 21±3 days (e.g., 18 to 24 days) after the Day 85 administration of the PD-1 inhibitor), on Day 127 (e.g., 21±3 days (e.g., 18 to 24 days) after the Day 106 administration of the PD-1 inhibitor), and on Day 148 (e.g., 21±3 days (e.g., 18 to 24 days) after the Day 127 administration of the PD-1 inhibitor). See, e.g., FIG. 1.

In some embodiments, during any time of the dosing schedule, one or more tests may be performed on the subject or using a sample obtained from the subject. Exemplary tests include one or more tests, e.g., to measure the levels of chemicals, biomarkers, metabolites, etc. (e.g., sodium, potassium, bicarbonate, BUN, creatinine, glucose, ALT, AST, bilirubin, alkaline phosphatase, amylase, thyroid stimulating hormone (TSH), LDH, serum prostate specific antigen (PSA), serum PAP, serum testosterone; blood tests (e.g., CBC, e.g., including, in some embodiments, a differential and platelet count); and other tests including, e.g., CT scan; bone scan; physical examination; leukapheresis; antibody panel; CTC counts; tissue biopsy; pulse; blood pressure; respiratory rate; body temperature; T-cell response; PET scan; questionnaire; etc.

Response to Therapy and Monitoring

In some embodiments, the response to therapy with the combination therapy described herein causes a decrease in size of a neoplastic lesion, decreases the biological tumor burden of the subject, etc. For example, in some embodiments a subject's "measurable" lesions are identified and monitored prior to, during, and after treatment. In some embodiments, the subject's tumor burden after initial treatment is evaluated to set a baseline for monitoring the course of treatment, e.g., to provide a measurement to which subsequent measurements are compared. In some embodiments, "baseline" tumor burden is determined by imaging the subject. As used herein, a subject has "measurable disease" when the subject has at least one "measurable lesion". As used herein, a "measurable lesion" is a lesion that can be accurately measured in at least one dimension (longest diameter to be recorded) as >20 mm (2.0 cm) with conventional techniques or as >10 mm (1.0 cm) with spiral CT scan. For lymph node metastases, a "measurable lesion" is at least 2.0 cm in longest diameter by spiral CT or conventional techniques. In some embodiments, tumor lesions that are situated in a previously irradiated area are not considered measurable. As used herein, a "non-measurable" lesion is a lesion that does not "measureable", e.g., all other lesions, including small lesions (longest diameter <20 mm (2.0 cm) with conventional techniques or <10 mm (1.0 cm) with spiral CT scan), lymph nodes <2.0 cm, and lesions for which measurements cannot be obtained reliably (e.g., bone lesions, leptomeningeal disease, ascites, pleural/pericardial effusion, lymphangitis cutis/pulmonis, abdominal masses that are not confirmed and followed by imaging techniques, and cystic lesions).

In some embodiments, a lesion is measured with positron emission tomography (PET) (e.g., $^{18}$F NaF PET). $^{18}$F NaF PET finds use in producing 3-dimensional measurements of, e.g., tissues, and thus provides a volumetric quantification of lesion volumes and therefore a measurement of total tumor volume.

In some embodiments, response to therapy is monitored by monitoring the sizes of measurable lesions representative of involved organs. In some embodiments, RECIST 1.1 is used for evaluation of radiographic data. In some embodiments, Immune related Response Criteria (irRC) based on WHO criteria are used for evaluation of immune-oncology, e.g., the irRECIST criteria that are based on RECIST 1.1, irRC, and Nishino (2013) "Developing a common language for tumor response to immunotherapy: immune-related response criteria using unidimensional measurements.", Clin Cancer Res. 19(14): 3936-43, incorporated herein by reference.

In some embodiments, target lesions are selected on the basis of size (e.g., those with the longest diameters) and their suitability for accurate repeated measurements. In some embodiments, response to therapy is monitored by calculating the sum of the longest diameters of all target lesions to provide a sum longest diameter. In some embodiments, the sum longest diameter is used to characterize the tumor response. For lesions measurable in 2 or 3 dimensions, the longest diameter at the time of each assessment is used. Further, in some embodiments lymph node measurements are made using short axis measurements, e.g., as per RECIST 1.1 and/or irRECIST.

In some embodiments, a subject is placed in a class based on the subject's response to treatment. For instance, a subject is placed in a "Complete Response (CR)" class based on the disappearance of all target lesions. In some embodiments, to be assigned a status of complete response, changes in tumor measurements are confirmed by repeat assessments performed no less than four weeks after the criteria for response are first met. In some embodiments, PSA is <0.2 ng/mL. In some embodiments, lymph nodes that shrink to less than 1.0 cm are considered normal. A subject is placed in a "Partial Response (PR)" class based on at least a 30% decrease in the sum of the longest diameters of target lesions, taking as reference the baseline sum longest diameter. In some embodiments, to be assigned a status of partial response, changes in tumor measurements must be confirmed by repeat assessments performed no less than four weeks after the criteria for response are first met. In some embodiments, there are no new lesions. A subject is placed in a "Progressive Disease (PD)" class based on at least a 20% increase in the sum of the longest diameters of target lesions, and a 0.5 cm absolute minimum increase, taking as reference the smallest sum longest diameter recorded since the baseline measurements, or the appearance of one or more new lesion(s). A subject is placed in a "Stable Disease (SD)" class based on neither sufficient shrinkage to qualify for partial response nor sufficient increase to qualify for progressive disease. In some embodiments, to be assigned a status of stable disease, measurements meet the stable disease criteria at least once after study entry at a minimum interval of 12 weeks.

In some embodiments, monitoring the response to treatment comprises monitoring non-target lesions, e.g., all lesions or sites of disease that are not target lesions. In some embodiments, non-target lesions are monitored, e.g., by bone scintigraphy. In some embodiments, a subject is placed into a subject class based on monitoring of non-target lesions. For instance, a subject is placed in a "Complete Response (CR)" class based on the disappearance of all non-target lesions and undetectable PSA tumor marker levels. In some embodiments, to be assigned a status of complete response, changes in tumor measurements are confirmed by repeat assessments performed no less than four weeks after the criteria for response are first met. In some embodiments, a subject is placed in a "Incomplete Response/Stable Disease (SD)" class based on the persistence of one or more non-target lesion(s) and/or the persistence of detectable serum PSA tumor marker levels. In some embodiments, to be assigned a status of stable disease, measurements meet the stable disease criteria at least once after study entry at a minimum interval of 12 weeks. In some embodiments, a subject is placed in a "Progressive Disease (PD)" class based on the appearance of one or more new lesion(s) and/or unequivocal progression of existing nontarget lesions. In some embodiments, for lesions only detectable by bone scan, the appearance of >2 new lesions, with symptoms, constitutes disease progression. Without symptoms, and if no other evidence of disease progression (e.g., no progressive disease by PSA or measurable disease criteria), in some embodiments progression is documented with bone scintigraphy, e.g., at least 6 weeks later demonstrating >2 new lesions, to eliminate the possibility of flair responses seen on bone scans.

In some embodiments, PSA progression (e.g., based on PSA amounts and/or kinetics) is monitored to monitor a subject's response to treatment. In some embodiments, a subject is classified as "PSA Complete Response" based on a decrease in PSA to <0.2 ng/mL. In some embodiments, placement in the "PSA Complete Response" class is confirmed with a later PSA measurement, e.g., at a minimum of four weeks later (confirmed PSA CR). In some embodiments, placement in the "PSA Complete Response" is further based on no evidence of radiographic progression. In some embodiments, a subject is placed in a "PSA Partial Response" class based on a greater than or equal to 50% reduction in baseline PSA. In some embodiments, placement in the "PSA Partial Response" class comprises no evidence of radiographic progression. In some embodiments, time to PSA progression is used to monitor a subject's response to treatment. As used herein, PSA progression refers to a 50% increase in PSA over the nadir PSA, and >2 ng/mL above the nadir, confirmed by a second value 3 or more weeks later (e.g., a confirmed rising trend). If no on-study reduction has occurred, nadir is baseline value (e.g., pre-treatment).

In some embodiments, subjects' immunological systems are monitored, e.g., by assessing PAP-specific CD8+ T-cell effector immunity, by assessing PAP-specific memory T-cell immunity, by assessing PAP-specific T cells, by assessing antigen-specific antibodies (e.g., PAP-specific antibodies), by assessing antigen-specific regulatory immune responses, and/or by assessing antigen-spread to other prostate-associated antigens. In some embodiments, a subject is evaluated by enumerating and characterizing circulating tumor cells. In some embodiments, a subject is evaluated using histology, e.g., by examining a tissue biopsy. In some embodiments, a subject is evaluated by quantitative total bone imaging using PET and/or CT (e.g., NaF PET/CT).

In embodiments comprising use of immunological monitoring, blood is collected by either peripheral blood draw (up to 120 mL) or leukapheresis (50-100 mL) pre-immunization, at weeks 6, 12 and 24 of treatment, and at months 9 and 12 (quarterly intervals up to one year). From the heparinized blood, peripheral blood mononuclear cells (PBMC) are prepared by density centrifugation over Ficoll-Paque using standard techniques. PBMC are used directly for analysis, and residual material is cryopreserved in liquid nitrogen using 90% autologous are prepared from the red-top tubes and stored in aliquots at −80° C. for antibody analyses. IFNγ and granzyme B ELISPOT analysis, PAP-specific T-cell proliferation, flow cytometric assays of antigen-specific cytokine secretion, and ELISA tests for antigen-specific antibodies are analyzed. The primary antigens tested are PAP (experimental), PSA (negative control), and tetanus toxoid (positive control). The primary immune analysis is conducted at the 6-month time point and compared with the pre-treatment time point, and for patients to be evaluable for immune response (primary endpoint), blood (PBMC and serum) from this time point will be saved for analysis. Immune monitoring is conducted at appropriate time points to evaluate kinetic measures of immunity and evaluate whether durable immune responses of particular phenotypes are elicited and/or maintained. In some embodiments, assays are conducted at the time of sample collection (fresh) and/or batched and performed at one time from multiple cryopreserved samples collected at different time points. In some embodiments, other methods of effector and regulatory T-cell response to PAP and other human tissue antigens are used.

In some embodiments, data are collected to assess PAP-specific IFNγ-secreting and granzyme B-secreting T-cell precursor frequency. In some embodiments, PAP-specific IFNγ-secreting and granzyme B-secreting T-cell precursor frequencies are quantified by ELISPOT. ELISPOT is used to assess (e.g., quantify) PAP-specific CD8+ T-cell effector immunity because detects low-frequency events (LOD~1: 100,000 cells) and provides for the simultaneous analysis of cryopreserved batched specimens 1301. IFNγ and granzyme B are evaluated because they are specifically associated with inflammatory/tissue-destructive (Th1-type, cytolytic) immune responses. Specifically, cryopreserved PBMC collected from subjects at the various time points are thawed, rested, and then transferred to 96-well nitrocellulose microtiter (ELISPOT) plates previously coated with monoclonal capture antibodies specific for IFNγ or granzyme B. $10^5$ cells per well are cultured in the presence of media (e.g., RPMI 1640 supplemented with L glutamine, penicillin/streptomycin, β-mercaptoethanol and 10% human AB serum) only (no antigen), 2 µg/ml PAP protein, 2 µg/ml PSA protein (negative control), 2 µg/ml of peptide libraries specific for PAP or control, 250 ng/ml tetanus toxoid, or 2.5 µg/ml PHA (positive mitogenic control) for 24-48 hours. Plates are then washed with PBS containing 0.05% Tween-20 and incubated for 2.5 hours at room temperature with 50 µl/well PBS containing 5 µg/ml biotinylated detection antibodies for either IFNγ or granzyme B. After incubation, wells are washed with PBS, further incubated with 100 µl/well streptavidin-labeled alkaline phosphatase (BioRad, Hercules, Calif.), and then developed with 100 µl/well BCIP/NBT colorimetric substrate (BioRad). The colorimetric reaction is stopped by rinsing the plates under cool tap water, and wells are allowed to dry completely before spots are enumerated with an ELISPOT automatic plate reader.

In some embodiments, results are calculated as the mean (+/− standard deviation) number of spot-forming-units (sfu) per $10^6$ cells (frequency), calculated by subtracting the mean number of spots obtained from the no-antigen control wells from the mean number obtained in the experimental wells, normalized to $10^6$ starting PBMC, from 8-well replicate assays [31]. Comparison of experimental wells with control (no-antigen) wells is performed using a two-sample t-test, with $p<0.05$ (two-sided) defined as a significant antigen-specific T-cell response. In some embodiments, a significant antigen-specific response resulting from immunization is a PAP-specific response detectable at the 6-month post-treatment time point (or other post-treatment time point evaluated) that is significantly higher than to media only (as above), at least 3-fold higher than the mean baseline value, and with a frequency >10 per $10^6$ PBMC.

In some embodiments, data are collected to assess PAP-specific memory T-cell immunity, e.g., by evaluating the ability of T-cell lines to proliferate in response to antigenic stimulation. T-cell proliferation in response to antigen stimulation provides a measure of memory T-cell responses and is assessed in some embodiments by a PKH26 dye dilution assay [31]. Specifically, PBMC are labeled in vitro with PKH26 dye (Sigma, St. Louis, Mo.) according to the manufacturer's recommendation. T-cell cultures with and without antigens are established in replicates using $2\times10^5$ peripheral blood mononuclear cells (PBMC)/well, plated in 96-well round bottom microtiter plates (Corning, Cambridge, Mass.), in media comprising RPMI 1640 (Gibco) and supplemented with L glutamine, penicillin, streptomycin, β-mercaptoethanol, and 10% human AB serum (ICN Flow, Costa Mesa, Calif.). In various embodiments, antigens include 2 µg/ml of a pool of peptides spanning the amino acid sequence of PAP, 2 µg/ml PAP protein (Research Diagnostics Inc., Flanders, N.J.), 2 µg/ml PSA (Research Diagnostics Inc.), 250 ng/ml tetanus toxoid, and 2.5 µg/ml phytohemaglutinin (PHA). After 6-7 days of culture at 37° C./5% $CO_2$, cell surface markers are stained to characterize the T-cell phenotype and memory phenotype of proliferating cells (CD45RO, CCR7). Flow cytometry is used to identify and enumerate CD3+CD4+ and CD3+CD8+ T cells co-staining for PKH26. The frequency of antigen-specific CD3+CD4+ and CD3+CD8+ T cells is calculated by determining the precursor frequency of PKH26+ events among CD4+ or CD8+ events (e.g., as estimated from the number of cells and number of cell divisions by dye dilution using ModFit software, Verity Software House, Topsham, Me.), and subtracting the mean precursor frequency of proliferating cells under media-only conditions. In some embodiments, other cell surface markers are assessed, other antigens evaluated, and/or other methods of antigen-specific T-cell proliferation are used.

In some embodiments, data are calculated as a mean and standard deviation of antigen-specific (PAP-specific) proliferative precursors per $10^6$ PBMC using triplicate assessments for each antigen-stimulation condition [31]. Comparison of experimental wells with control (no antigen) wells is performed using a two-tailed Student's t test, with $p<0.05$ defined as a significant antigen-specific proliferative T-cell response. In some embodiments, a significant antigen-specific response resulting from immunization is a PAP-specific response detectable at the 6-month post-treatment time point (or other post-treatment time point evaluated) that is significantly higher than to media only (as above), at least 3-fold higher than the mean baseline value, and with a frequency >100 per $10^6$ CD4+ or CD8+ T cells.

In some embodiments, data are collected to assess PAP-specific T-cell cytokine expression, e.g., by intracellular cytokine staining. In some embodiments, as another method of evaluating AR LBD-specific T cell responses, intracellular cytokine staining is used. Specifically, fresh or cryopreserved PBMC from subjects at the various time points are rapidly thawed, cultured in 96-well microtiter plates in the presence of test antigens (e.g., PAP (protein or pool of overlapping 15-mer peptides), PSA, tetanus, PHA, or media only) for 4-24 hours, and then analyzed for intracellular cytokine expression. Specifically, stimulated cells are treated with monensin for 4-8 hours at 37° C./5% $CO_2$. Cells are then washed with PBS/3% FCS, followed by staining for surface molecules (e.g., CD3, CD4, and CD8 to identify T cell subsets, as well as CCR7 and CD45RO to identify memory populations, and potentially other cell surface markers). Cells are then fixed, permeabilized, and stained for intracellular expression of a panel of cytokines (e.g., including, but not limited to, IFNγ, TNFα, IL-2, IL-17, and IL-10), or control IgG labeled with the appropriate fluorochromes. Cells are analyzed on a flow cytometer, and results will be determined by identifying the frequency of T cells (e.g., either total T cells and/or T cell subsets, including CD4+ and CD8+ T cells, as well as various memory populations or regulatory populations) expressing each individual cytokine, or cells expressing multiple cytokines.

In some embodiments, data are reported as a mean and standard deviation of antigen-specific (e.g., PAP-specific) CD4+ or CD8+ T cells expressing one or more cytokines per $10^6$ PBMC using triplicate assessments for each antigen-stimulation condition, as previously reported [31]. Comparison of experimental wells with control (no antigen) wells is performed using a two-tailed Student's t test, with $p<0.05$ defined as a significant antigen-specific T-cell response. In some embodiments, a significant antigen-specific response resulting from immunization is a PAP-specific response detectable at the 6-month post-treatment time point (or other post-treatment time point evaluated) that is significantly higher than to media only (as above), at least 3-fold higher than the mean baseline value, and with a frequency >100 per $10^6$ CD4+ or CD8+ T cells.

In some embodiments, data are collected to assess antigen-specific antibody immunity. For example, in some embodiments enzyme-linked immunosorbent assay (ELISA) is used for the detection of antibodies responses to PAP. In particular embodiments, the presence of a coexisting humoral immune response to PAP (or other antigens) is evaluated by ELISA using an indirect method similar to that described previously [34]. Specifically, Immulon-4 ELISA plates (Dynex Technologies Inc.) are coated with 2 µg/ml purified PAP protein (Research Diagnostics, Inc., or other antigens or commercial sources) in 0.1 M $NaHCO_3/Na_2CO_3$ buffer (pH 9.6) overnight at 4° C. After blocking with PBS/1% BSA for 1 hour at room temperature, wells are washed with PBS and 0.05% Tween-20 (PBS-Tween), and then incubated for 1 hour with human sera diluted 1:25, 1:50, 1:100, and 1:200. After washing, plates are sequentially incubated with a peroxidase-conjugated anti-human IgG detection antibody (Amersham), followed by peroxidase enzyme TMB substrate (Kierkegaard and Perry Laboratories). The color reaction is stopped with 1N $H_2SO_4$ and the optical density measured at 450 nm. Antibody titers for PAP-specific IgG antibodies are determined as previously described [34].

In some embodiments, IgG response are reported graphically using sera dilution curves and by titer (e.g., defined as the highest sera dilution at which IgG responses are detectable above the mean+3 standard deviations of the negative control). In some embodiments, a positive IgG response resulting from immunization is an antigen-specific (anti-PAP) IgG titer at least 4-fold higher than the baseline titer detectable at the 6-month post-treatment time point (or other post-treatment time point evaluated).

In some embodiments, data are collected to assess antigen-specific regulatory immune responses, e.g., by a transvivo delayed-type hypersensitivity (tvDTH) evaluation. In some embodiments, 7.5 to $10\times10^6$ PBMC obtained from patients prior to and after immunization are co-injected into the footpads of 6-week to 8-week old SCID mice with 1 µg of PAP protein (Fitzgerald Industries, Acton, Mass.), or tetanus toxoid (TT/D; Aventis Pasteur, Bridgewater, N.J.) as a recall antigen, versus phosphate-buffered saline (PBS) alone as a negative control. In some embodiments, other antigens are also evaluated.

Antigen-driven swelling is determined as previously described [65]. DTH reactivity after 24 hours is shown as a change in footpad thickness, e.g., measured in multiples of $10^{-4}$ inches, measured using a dial thickness gauge (Mitutoyo, Japan), and net swelling is the antigen-specific swelling subtracted for the contribution obtained with PBMC plus PBS. To determine the effect of neutralizing antibodies, PBMC is mixed with 1 µg of PAP antigen and 25 µg of either control IgG or rabbit anti-human TGF-6, goat anti-human IL-10 (R&D Systems, Minneapolis, Minn.), 1 µg of mouse anti-human CTLA-4 monoclonal Ab (clone AS32, Ab Solutions, Mountain View, Calif.), or 1 µg of mouse anti-human PD-1 monoclonal Ab (or, in some embodiments, other antibodies to other regulatory molecules), and injected into the footpads of SCID mice as above. The extent of bystander suppression, indicating an antigen-specific regulatory response, is measured as inhibition of recall antigen (tetanus) response in the presence of PAP antigen (or prostate-specific antigen (PSA) as a negative control) and calculated as previously described [66].

Figure 2:
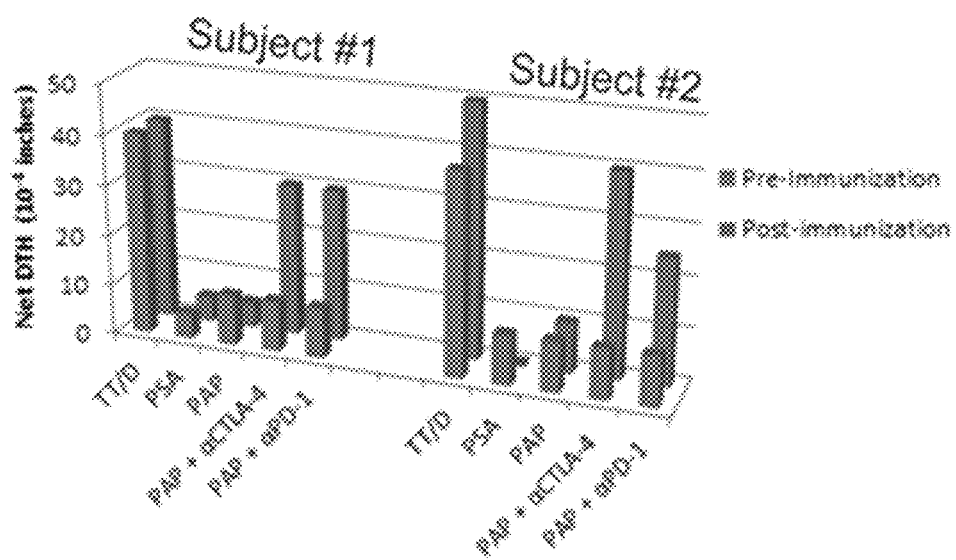
FIG. 2: Plot showing that patients treated with pTVG-HP develop T cell responses to PAP, the function of which is regulated by PD-1. PBMC obtained from 2 patients pre (blue) or 2 weeks post (red) a 12-week treatment with pTVG-HP were placed in the footpads of SCID mice with the 1 µg of the antigens listed (TT/D=tetanus toxoid, positive control, PSA=negative control), with or without 1 µg of anti-CTLA-4 or anti-PD1. DTH responses were read at 24 hours. As shown, both patients had responses to PAP after immunization that were "uncovered" by either CTLA-4 or PD-1 blockade.

In some embodiments, an antigen-specific (PAP-specific) regulatory response is an inhibition of a recall antigen (tetanus toxoid) DTH response by >50% when performed in the presence of PAP; e.g., a DTH response in the presence of PAP+TT that is <50% of that obtained with TT only. Further, in some embodiments, the identification of PD-1 (or CTLA-4) regulated responses is an increase ($>15\times10^{-4}$ inches) in a PAP-specific response in the presence of anti-PD-1 (or anti-CTLA-4) versus IgG control, as in FIG. 2.

In some embodiments, antigen-spread to other prostate-associated antigens is assessed, e.g., by high-throughput immunoblot (HTI). In some embodiments, tests are conducted to determine if treated patients develop "off-target" prostate cancer antigen-specific immune responses as evidence of antigen spread. For example, in some embodiments studies evaluate T-cell responses to non-targeted antigens. And, in some embodiments patients are evaluated to assess IgG responses to a panel of prostate-associated antigens (e.g., as has been observed in patients treated with vaccines or other immune-modulating agents) [67, 68, 69]. Tests are conducted to assess IgG specific for 126 antigens, including 29 cancer-testis antigens [70, 71]; further, in some embodiments 97 prostate antigens frequently immunologically recognized [72, 73, 74, 75] are identified by screening a high-density phage array expressing these individual antigens [67, 69, 70]. In some alternative embodiments, this approach includes evaluating responses to panels of protein antigens fixed to support membranes provided by commercial vendors. In some embodiments, the analysis is conducted using sera obtained at 6 months and compared with IgG responses identified at baseline to determine whether IgG specific for individual antigens are elicited over time. In some embodiments, other time points are assessed to determine the durability and kinetics of immune response development. In some embodiments, confirmatory ELISA studies are performed.

In some embodiments, a positive IgG response is an immunoreactive spot to a defined antigen (e.g., scored by at least 3 of 4 independent reviewers) and detectable to at least 2 of 3 replicates per immunoblot membrane [67, 76] or by statistically defined criteria using commercial antigen sources. In some embodiments, an IgG response resulting from immunization is defined as an immunoreactive antigen identified at the 6-month (or other post-treatment time for subsequent analyses) time point that was not identified at the pre-treatment time point.

In some embodiments, subjects are assessed for circulating tumor cells (CTC). In some embodiments, CTC are enumerated and characterized. In some embodiments, evaluation is performed at the same time points as for immune evaluation (e.g., at various time points such as at pre-treatment, after 6 weeks, and at quarterly intervals for up to one year) using flow cytometry. Specifically, PBMC are stained with fluorochrome-labeled antibodies specific for one or more of, e.g., CD45, EpCAM, PD-1, PD-L1, CTLA-4, and DAPI (see, e.g., FIG. 3). In some embodiments, CTC are detected as CD45−EpCAM+DAPI− cells, and the percentage of these events among all live cellular events are determined at the different time points. In some embodiments, the % of CTC expressing PD-L1, PD-L2, HVEM, or galectin molecules are also determined. In some embodiments, results are reported for the different time points, and general trends are assessed. In some embodiments, other methods of CTC capture and enumeration are used and, in some embodiments, further investigational studies are conducted with CTC collected by these methods.

In some embodiments, subjects are evaluated using histopathology. For example, in some embodiments, tissue biopsies are obtained from metastatic lesions (e.g., the same lesion per patient), e.g., prior to treatment and at week 12. In some embodiments, studies are conducted to test the association of immunization with PD-L1 expression on tumor cells, e.g., in the tumor (e.g., by eliciting tumor antigen-specific T cells secreting IFNγ), to test the association of concurrent treatment with anti-PD-1 mAb with infiltration of CD8+ T cells (e.g., causing an increase in infiltration), and to test the association of treatment with expression (e.g., increased expression) of other T-cell regulatory ligands on T cells (e.g., PD-1, CTLA-4, TIM-3, BTLA, LAG-3) or tumors (e.g., HVEM, phosphatidyl serine, PD-L2). Subsequently, in some embodiments biopsy specimens (e.g., obtained pre-treatment and after 12 weeks) are stained with antibodies, e.g., antibodies specific for CD3, CD4, CD8, FoxP3, PD-1, CTLA-4, TIM3, BTLA, LAG-3, PD-L1, PD-L2, phosphatidyl serine, HVEM and in some embodiments other markers. Staining and quantification are reviewed by a pathologist blinded to the treatment groups to determine CD8+ T cells per field, CD4+FoxP3+ (Treg):CD8+ T cell ratio, PD-L1 expression, and whether these parameters change over time, e.g., from pre-treatment to the 12 week time point.

In some embodiments, subjects are evaluated using total bone imaging (e.g., quantitative total bone imaging, QTBI) using NaF PET/CT. For example, in some embodiments an assessment of small volume bone metastatic disease and tumor growth rates are conducted using QTBI. For example, in some embodiments, the subject has a bone disease that is not detected by standard bone scintigraphy. In some embodiments, patients are assessed at various time points, e.g., at 1 month prior to treatment, at baseline, and at 3 months on treatment. In some embodiments, metastatic prostate cancer lesions in bone are localized and identified based on functional NaF PET uptake, assisted with the anatomical information provided by CT scans. In some embodiments, segmentation is performed using an automatic segmentation method (e.g., using a fixed SUV threshold), and adjusted with physician guidance. In some embodiments, scans from different time points are registered to one another using an articulated registration technique employing a rigid registration of skeletal elements (e.g., bones) from CT followed by registration optimization by combining with deformable registration of bones and lesions from NaF PET/CT. In some embodiments, the lesions between pre-treatment and follow-up scans are matched to establish longitudinal correspondence of lesions. For each patient, in some embodiments, comprehensive treatment response metrics are calculated, comprising, e.g., $SUV_{total}$ (total disease burden), $SUV_{max}$ (maximum intensity lesion), $SUV_{mean}$ (average intensity), the number of lesions, and total volume of bone lesions. In addition, imaging response metrics are calculated in some embodiments for each individual lesion. In some embodiments, this methodology is used to assess the growth rate of bone metastatic disease by evaluating changes over time, e.g., from pre-treatment to baseline and comparing this to measurements made from baseline to month 3.

Thus, the technology relates to treatment of a subject with a DNA vaccine and a PD-1 inhibitor to produce a clinical outcome in the subject. In some embodiments, the improvement is an increase or a decrease in a detectable characteristic of the subject relative to an earlier measurement of the detectable characteristic. In some embodiments, the earlier measurement is a measurement performed prior to the initiation of treatment (e.g., a "pre-treatment" measurement). In some embodiments, the earlier measurement is a measurement performed after treatment has been initiated.

For example, in some embodiments the methods provided herein produce an improvement in one or more of: the magnitude of PAP-specific T-cell responses; magnitude of expression of PD-1 on circulating T-cells (CD4+ or CD8+); magnitude of expression of PD-L1 on circulating epithelial (e.g., tumor) cells (e.g., CTC) in blood; magnitude of expression of PD-L1 on T-cells (e.g., as detected in tumor biopsies); amount of CTCs in blood; induction of, or change in, PAP-specific antibody quantification in blood; and/or elicitation of immune response to non-PAP prostate associated antigens (antigen spread).

In some embodiments, the improvement is an increased PAP-specific T-cell response; increased expression level of PD-1 or PD-L1 on circulating T-cells (CD4+ or CD8+); increased number or percentage of PD-L1 positive or of PD-L positive circulating epithelial (e.g., tumor) cells (e.g., CTC) in blood; increased expression of PD-L1 or PD-1 on T-cells (e.g., as detected in tumor biopsies); decreased amount of CTCs in blood; increased PAP-specific antibody in blood; and/or elicitation of immune response to non-PAP prostate associated antigens (antigen spread).

In some embodiments, the improvement is relative to the pre-treatment amounts of these various measures. In some embodiments, the improvement is relative to a measurement obtained at an earlier time.

In some embodiments, the treatments with the DNA vaccine and PD-1 inhibitor described herein produce an improvement in a pre-existing or treatment-induced expression of one or more regulatory molecules (e.g., TIM3, BTLA, and/or LAG3) on tumor-specific circulating or tumor resident T-cells. In some embodiments, the treatments with the DNA vaccine and PD-1 inhibitor described herein produce an improvement in a pre-existing or treatment-induced expression of regulatory molecules (e.g., HVEM, phosphatidyl serine, PD-L2) on tumor cells (e.g., on CTCs or in tumor biopsies). In some embodiments, the treatments with the DNA vaccine and PD-1 inhibitor described herein produce an improvement in a pre-existing or treatment-induced PD-1-regulated, PAP-specific T-cells. In some embodiments, the improvement is identified by a trans vivo Delayed Type Hypersensitivity (DTH) assay.

Kits

In some embodiments, the technology provides kits for treating a subject having prostate cancer or a subject at risk for prostate cancer. For example, some embodiments provide a first composition (e.g., a first pharmaceutical composition) comprising a nucleic acid (e.g., DNA) vaccine (e.g., comprising a nucleic acid comprising a nucleotide sequence from a PAP gene) and a second composition (e.g., a second pharmaceutical composition) comprising a PD-1 inhibitor. In addition, some kit embodiments further comprise a product insert providing a dosing schedule comprising instructions relating to the administration of the nucleic acid vaccine and the PD-1 inhibitor.

In some embodiments, the nucleic acid vaccine comprises pTVG-HP and the PD-1 inhibitor is a monoclonal antibody inhibitor of PD-1. In some embodiments, the nucleic acid vaccine comprises pTVG-HP and the PD-1 inhibitor is pembrolizumab. In some embodiments, the nucleic acid vaccine comprises pTVG-HP and the PD-1 inhibitor is nivolumab. In some embodiments, the DNA vaccine comprises an adjuvant, e.g., GM-CSF.

In some embodiments, the DNA vaccine and PD-1 inhibitor are provided as ready-to-use pharmaceutical compositions. In some embodiments, the DNA vaccine and PD-1 inhibitor are provided in a dried (e.g., lyophilized) state, e.g., for solubilization and/or resuspension in a pharmaceutically appropriate solution prior to administration.

In some embodiments, the kits comprise the DNA vaccine and the PD-1 inhibitor in a vessel such as a vial, ampule, bottle, etc. In some embodiments, the DNA vaccine and the PD-1 inhibitor are provided in single-dose amounts in a vessel such as a vial, ampule, bottle, etc. For instance, some kit embodiments comprise: 1) a first vial comprising a pharmaceutical composition comprising approximately 100 µg of the DNA vaccine (e.g., pTVG-HP) and approximately 208 µg of GM-CSF; and 2) a second vial comprising from 10 mg to 1000 mg of PD-1 inhibitor. In some embodiments, the first vial comprises approximately 200 to 300 µl of the pharmaceutical composition. In some embodiments, kits comprise two vials of the DNA vaccine to provide two doses of the DNA vaccine.

Some embodiments of the kits provide multiple doses of the DNA vaccine and PD-1 inhibitor, e.g., to provide a sufficient number of doses to complete a dosing schedule as described herein. For example, some embodiments of kits comprise 5 to 20 vials of the DNA vaccine and some embodiments of kits comprise 2 to 10 vials of the PD-1 inhibitor.

EXAMPLES

Example 1—Role of PD-1 in Patients Previously Receiving PAP Vaccine

While DNA vaccines elicit antigen-specific CD8+ T-cells in humans that persist over time scales on the order of years, the persistence of antigen-expressing tumors demonstrates that mechanisms of tumor escape are at play. For example, data collected in human trials indicated that some patients did not develop evidence of immune response, and even those that did still showed evidence of disease progression. Accordingly, to improve the immunological activity of DNA vaccines (e.g., in the development of a DNA vaccine for the treatment of prostate cancer), experiments were conducted during the development of embodiments of the technology to collect data related to mechanisms of tumor resistance.

Figure 3:
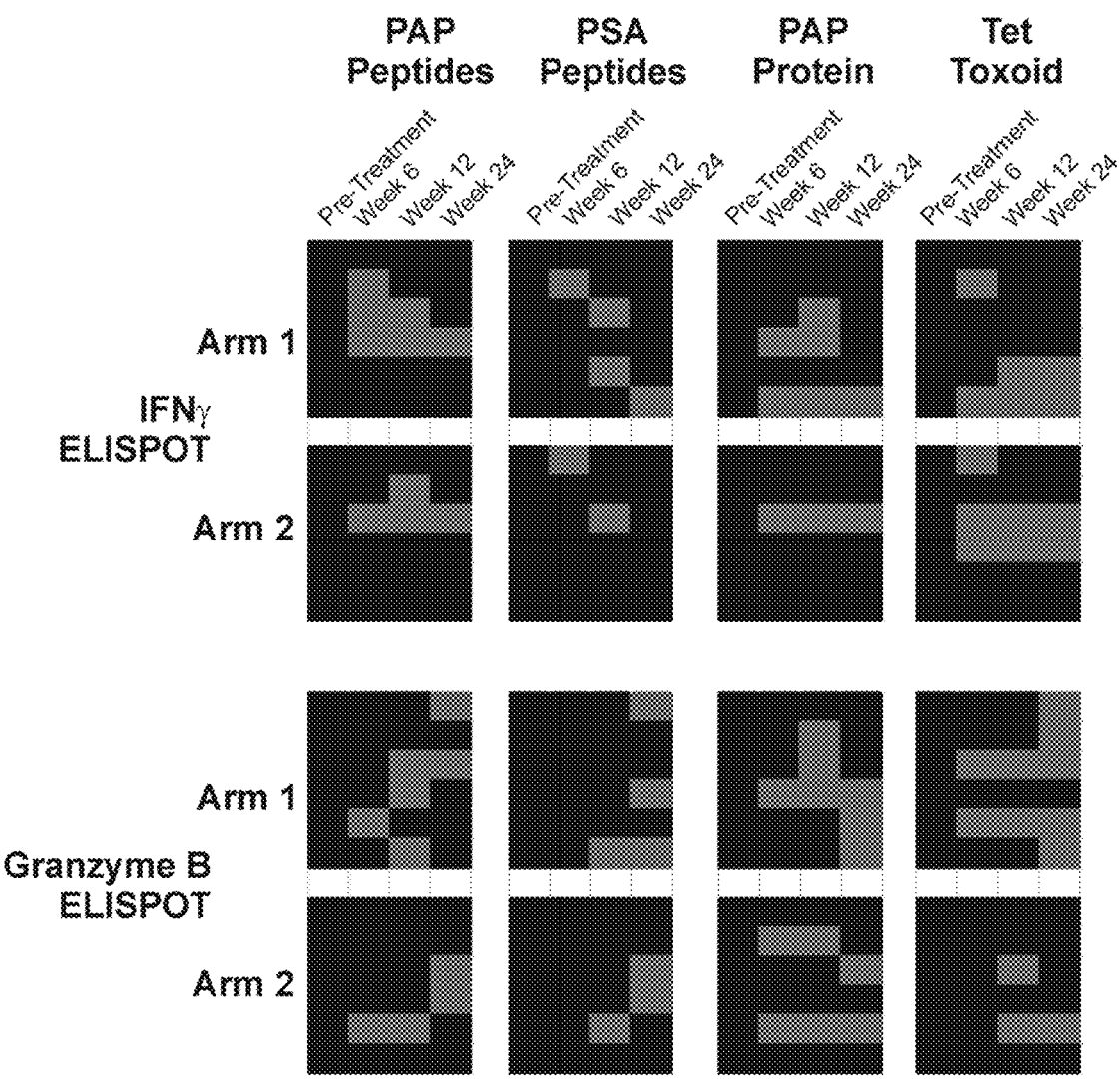
FIG. 3: Immunological response—IFNγ and Granzyme B ELISPOT. Peripheral blood mononuclear cells were collected from all subjects at baseline, 6 weeks, 12 weeks, and 24 weeks and evaluated for antigen-specific IFNγ or granzyme B secretion by ELISPOT. A positive antigen-specific response was defined as a statistically significant response (compared with media control) that was at least 3-fold over the baseline value and with a frequency of at least 1/100,000 cells. Shown are patients grouped by study arm. Red squares indicate positive responses.
Figure 4:
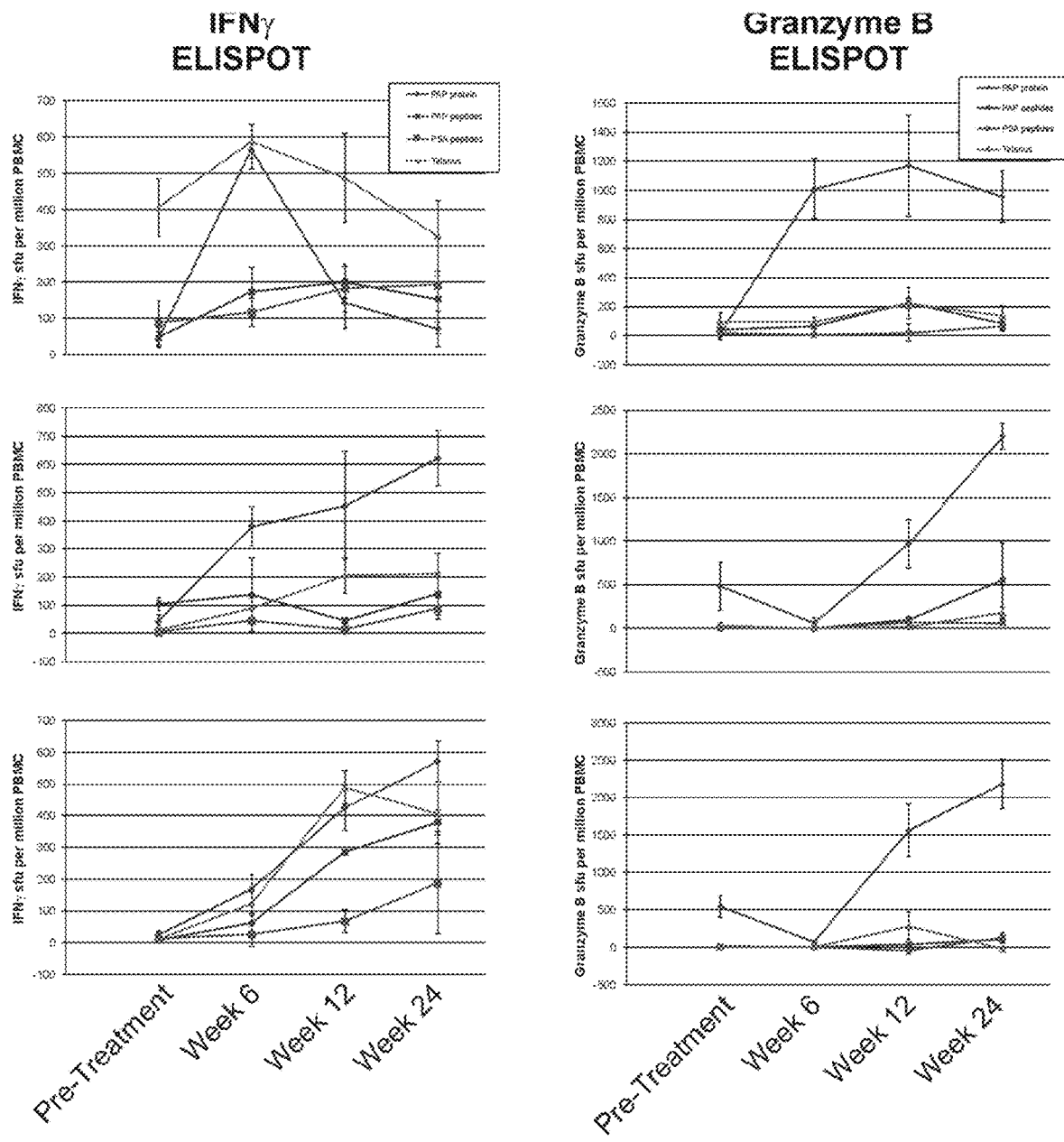
FIG. 4: IFNγ and Granzyme B ELISPOT data for individuals with persistent PAP-specific immunity. Shown is individual ELISPOT data for the three individuals who exhibited PAP-specific immunity at all post-treatment time points in FIG. 3. The top four panels were from two patients treated in Arm 1. The bottom panels were from a patient treated in Arm 2.

The role of PD-1 in patients who previously received a DNA vaccine encoding PAP was evaluated. In particular, experiments were conducted using a delayed-type hypersensitivity (DTH) model to evaluate mechanisms of immune regulation, similar to previously reported studies [56]. While a small number, it was found in 2 of 2 patients evaluated prior to and after DNA vaccination that PD-1 blockade, like CTLA-4 blockade, could restore effector function (as measured by DTH) of PAP-specific T cells elicited with vaccination (FIG. 3). It was also found in a patient previously treated with pTVG-HP, who then subsequently received sipuleucel-T for metastatic disease, that PD-L1 expression could be directly detected on circulating $CD45^-EpCAM^+$ cells (FIG. 4).

It is contemplated that the trans vivo DTH method can identify patients with antigen-specific PD-1-mediated regulation as either a predictive biomarker or measure of response, and that the presence of PD-L1 on circulating epithelial (tumor) cells is a predictive biomarker or measure of response similar to what has been proposed for other studies using PD-1 blocking antibodies [18].

Example 2—Clinical Results Obtained from Co-Administration of Pembrolizumab and pTVG-HP DNA Vaccine in Patients with Castration-Resistant Metastatic Prostate Cancer This example provides results obtained from co-administration of pembrolizumab and pTVG-HP DNA vaccine to patients with castration-resistant metastatic prostate cancer. Briefly, patients in the trial were divided into two arms. The first arm (the concurrent arm) received a concurrent administration of pembrolizumab and pTVG-HP DNA vaccine on day 1 and then subsequent administrations of pembrolizumab every 3 weeks thereafter and pTVG-HP DNA vaccine every 2 weeks thereafter through 10 weeks. The second arm (the sequential arm) received the pTVG-HP DNA vaccine every 2 weeks for a total of 10 weeks followed by administration of pembrolizumab every 3 weeks, beginning at week 12, through week 21. The administration schedules are summarized in FIG. 1. Results: While trial accrual continues, we report here that of the first 14 patients enrolled, grade 3 events included fatigue, diarrhea and hepatitis, and no grade 4 events were observed. One death occurred after treatment was discontinued, possibly related to pembrolizumab. 4/11 (36%) evaluable patients experienced PSA declines and 3/11 (27%) experienced decreases in tumor volume by radiographic imaging before treatment was discontinued. Expansion of PAP-specific Th1-biased T cells was detected in peripheral blood samples and were persistently elevated in two patients with the greatest PSA and radiographic changes. These data are the first report of a clinical trial combining an anti-tumor vaccine with PD-1 blockade, and suggest that the efficacy of anti-tumor vaccines can be augmented by combination with PD-1 blockade.

Materials and Methods:

Study Agent and Regulatory Information:

pTVG-HP is a plasmid DNA encoding the full-length human PAP cDNA downstream of a eukaryotic promoter[25]. The study protocol was reviewed and approved by all local and federal (FDA, NIH Recombinant DNA Advisory Committee) entities. All patients gave written informed consent for participation.

Patient Population:

Subjects were male patients with a histological diagnosis of adenocarcinoma of the prostate with metastases and evidence of castration resistance. Patients were required to continue androgen deprivation (surgical castration or GnRH analogue or antagonist treatment), and were required to have progressive disease, as defined by consecutive rise in serum PSA, and/or increase in disease burden by CT or bone scintigraphy, at the time of registration. No other concurrent anti-cancer therapy, or treatment within 28 days prior to registration was permitted. Prior treatment with abiraterone and/or enzalutamide was allowed, however treatment with cytotoxic chemotherapy within 6 months of registration was prohibited, and prior treatment with sipuleucel-T was prohibited. Inclusion criteria required that patients have an Eastern Cooperative Oncology Group performance score of ≤2, and normal bone marrow, liver and renal function as defined by a WBC≥2000/µL, hemoglobin ≥9.0 g/dL, platelet count ≥100,000/µL, AST and ALT≤2.5×institutional upper limit of normal, and serum creatinine ≤2.0 mg/dL.

Study Design:

This study is an open-label, single institution, randomized pilot trial designed to evaluate the immunological and clinical effect of pTVG-HP with recombinant human GM-CSF given as an adjuvant, and delivered concurrently or sequentially with pembrolizumab. The total accrual goal is 32 subjects, based on the goal of detecting an anticipated 45% increase in progression-free survival rate at 6 months in the concurrent treatment with 80% power at the one-sided 10% significance level.

Study Procedures:

The trial schema is shown in FIG. 1. Patients were treated six times at 14-day intervals with pTVG-HP plasmid admixed with 200 mcg GM-CSF (Leukine®, sargramostim). Vaccinations were administered intradermally with a 28-gauge needle on the lateral arm in two divided injections. Patients treated in Arm 1 received four doses of pembrolizumab (2 mg/kg administered intravenously) at 3-week intervals, beginning on the first day of immunization, over the first 12 weeks of treatment. Patients treated in Arm 2 received four doses of pembrolizumab (2 mg/kg administered intravenously) at 3-week intervals, but beginning 2 weeks after the last immunization, over weeks 12-24 of treatment. All patients underwent a leukapheresis procedure within two weeks of the first immunization and six months after beginning study treatment, and peripheral blood draws at week 6, 12, 36 and 48, for immunological assessments.

Patients also received a tetanus immunization immediately following the baseline leukapheresis. Blood tests were performed approximately every 3 weeks and included CBC, creatinine, electrolytes, glucose, bilirubin, ALT, AST, alkaline phosphatase, amylase, LDH, and TSH. All toxicities were graded according to the NCI Common Terminology Criteria Grading System, version 4.

Clinical Response Evaluation:

Serum PSA and PAP values were collected every 3-6 weeks from all individuals over the 24-week period. PSA values were available from all patients prior to enrollment. CT of chest/abdomen/pelvis and bone scans were obtained within 6 weeks prior to the first day of treatment, and then at 12-week intervals following day 1. Tumor response measurements were made as per Prostate Cancer Working Group 2 (PCWG2) recommendations[64].

Immunological Response Evaluation:

For each time point, measures of antigen-specific immune response were performed by ELISPOT with fresh (not cryopreserved) peripheral blood mononuclear cells (PBMC) as previously described[30,31]. Specifically, studies were conducted using monoclonal capture antibodies specific for IFNγ (Thermo Scientific, Pittsburgh, Pa.) or granzyme B (GeneTex Inc., Irvine, Calif.). Antigens used included tetanus toxoid protein (Calbiochem, San Diego, Calif.), PSA or PAP protein (Research Diagnostics Inc., Flanders, N.J.), or pools of 15-mer peptides spanning the amino acid sequence of PAP or PSA and overlapping by 11 amino acids (LifeTein, LLC, Hillsborough, N.J.). For these analyses, all antigens and sera used were from the same lots to control for possible variation over time. Plates were then washed, developed with biotinylated detection antibodies for either IFNγ (Thermo Scientific) or granzyme B (GeneTex Inc), and spots enumerated by automated ELISPOT reader. A response resulting from immunization was defined as a PAP-specific response detectable post-treatment that was both significant (compared to media only control), at least 3-fold higher than the pre-treatment value, and with a frequency >1:100,000 PBMC[31].

Statistical Analysis:

All clinical outcomes and immunological parameters were summarized using descriptive statistics in terms of means, standard deviations, medians and ranges or frequencies and percentages. A two-sample test was used to compare antigen-specific T-cell response to media control at the two-sided 0.05 significance level.

Results:

Patient Population and Course of Study:

Fourteen patients were enrolled in this trial between at the University of Wisconsin Carbone Cancer Center. The general schema for the treatment is shown in FIG. 1. The median age of participants was 69 years (range 54-83 years). Over the course of treatment, no grade 4 events were observed. One subject experienced grade 3 fatigue, another individual (Arm 2) experienced grade 3 hepatititis beginning at week 24, and another experienced grade 3 diarrhea. Grade 2 events believed at least possibly related to study treatment included fatigue, constipation, diarrhea, nausea, arthralgias, hot flashes, hypothyroidism, hyperthyroidism, and pain. The patient with grade 3 diarrhea (Arm 2) died within 30 days of being taken off trial, and 46 days after his last treatment with pembrolizumab, due to multi-organ failure that was felt to be at least possibly related to the diarrhea that was attributed to treatment with pembrolizumab. Two patients, one in each study arm, had evidence of progressive disease within the first month, came off study, and hence were not evaluable for immunological or clinical response.

Immunological Response:

Patients were evaluated prior to treatment, and at weeks 6, 12 and 24 for evidence of T cell immune response to the PAP target antigen by ELISPOT. As shown in FIG. 3, a significant increase in PAP-specific IFNγ-secreting T cells was detected in multiple subjects treated on either study arm. 4/12 (33%) individuals had evidence of persistent immunity, with significant increases in PAP-specific T cells detectable at more than one post-treatment time point. Cytolytic type responses specific for PAP, secreting granzyme B, were also detectable. As shown 3/12 (25%) of individuals had evidence of persistent immunity, with significant increases in PAP-specific granzyme B-secreting cells detected at more than one post-treatment time point. One individual had a response in vitro to the PAP protein but not the peptide library spanning the amino acid sequence of PAP. This suggests that the response elicited was to an epitope, or perhaps a small number of epitopes, not present in the peptide library. T cell responses to tetanus were detectable in multiple patients, as expected, given that patients received a tetanus immunization prior to study treatment to provide a positive control. While responses to PSA, as a negative control, were detectable at discreet time points based on the definition of immune response, persistent PSA-specific IFNγ-secreting responses, detectable at more than one post-treatment time point, were not detected. Three patients, two in Arm 1 and one in Arm 2, had evidence of PAP-specific IFNγ-secreting T cells at all post-treatment time points, as further illustrated in FIG. 4.

Figure 5A:
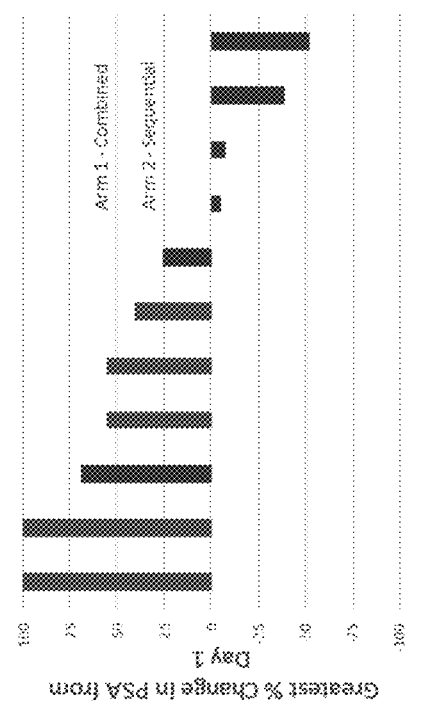
FIGS. 5A-D: Serum PSA responses. Serum PSA values were collected from all individuals prior to treatment and over the course of treatment. Serum PAP values were collected from individuals at baseline and over the course of treatment. Panel A: Percent changes in serum PSA values were evaluated from day 1 of study. Panel B: Percent changes in serum PSA values were evaluated from day of beginning pembrolizumab treatment (day 1 for patients in Arm 1, and week 12 for patients in Arm 2). Panel C: Maximum % change in serum PSA from day 1 of study. Panel D: Maximum % change in serum PAP from day 1 of study. (see FIG. 1 for administration schedule).
Figure 5C:
Figure 5B:
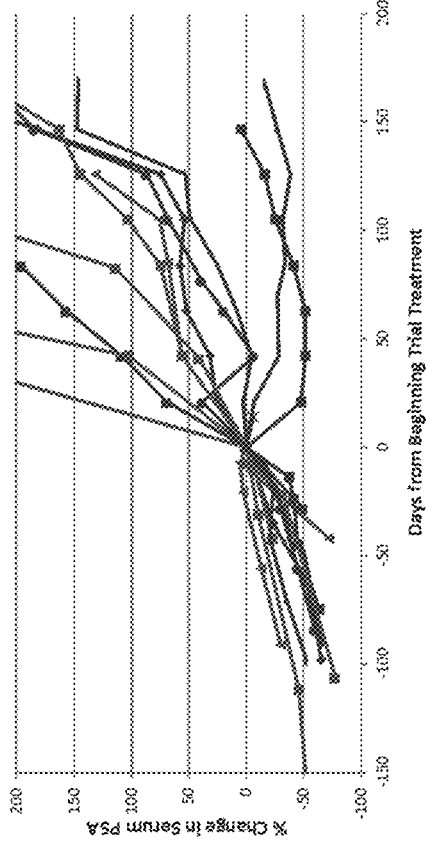
Figure 5D:
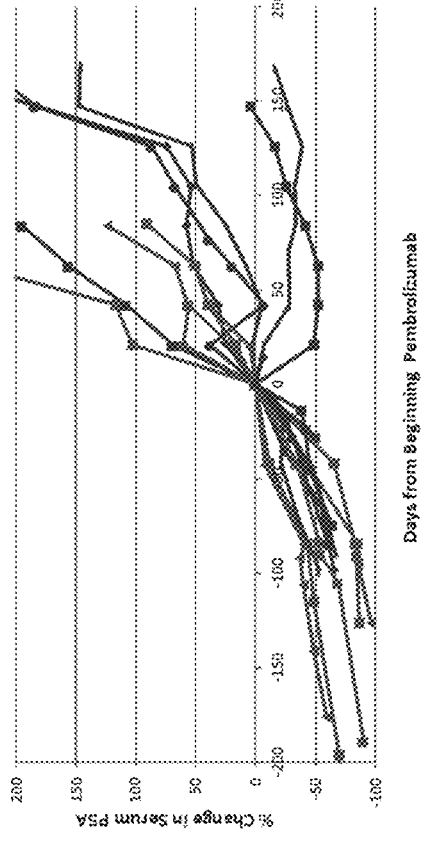

Clinical Effects:

In addition to two patients who came off study early, an additional patient was found at day 1 to have a lower PSA from screening, consistent with a delayed bicalutamide withdrawal response. Consequently his serum PSA and imaging were not included for response evaluation. There were no complete serum PSA responses, however 1/11 individuals experienced a ≥50% decrease in serum PSA (from 65 ng/mL to 31 ng/mL). % change in serum PSA from day 1 of study (first vaccination, with or without pembrolizumab) is shown for all patients with respect to treatment arm in FIG. 5A. In addition, to specifically evaluate the effect of pembrolizumab on serum PSA, FIG. 5B demonstrates % change in serum PSA from day 1 of treatment with pembrolizumab (day 1 of study for Arm 1, and week 12 of study for Arm 2). As demonstrated in FIG. 4C, any serum PSA declines from baseline were observed in 4/11 (36%) patients, and only in patients treated in Arm 1. Similarly, serum PAP declines (FIG. 5D) were observed in 5/11 (45%) of patients, and only in patients treated in Arm 1.

Figure 6:
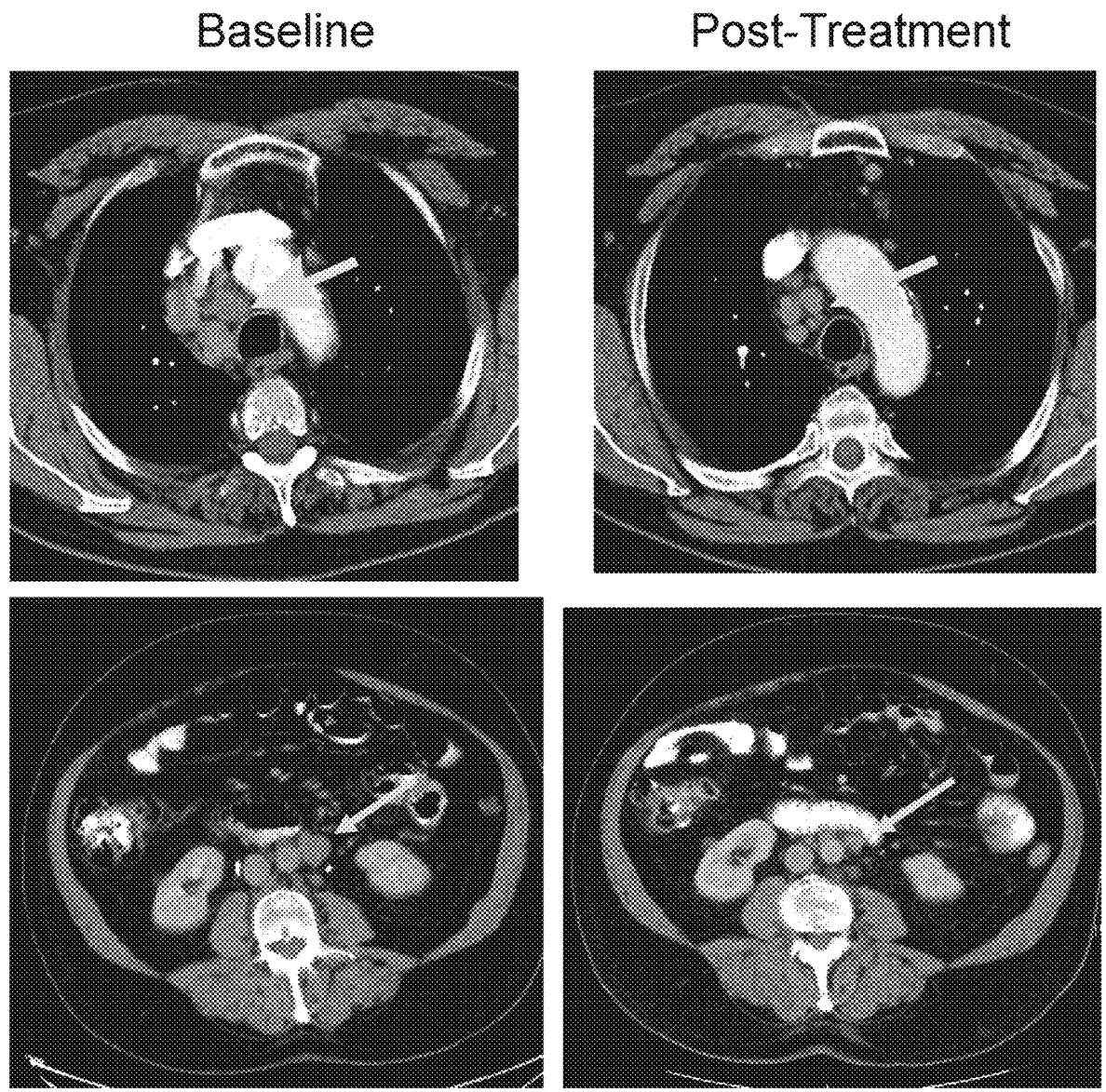
FIG. 6: Objective radiographic changes. Shown are CT images collected at baseline and 24 weeks (top panel) or 12 weeks (bottom panel) post-treatment for two individuals treated in Arm 1. Arrows point to lymph node metastases.

CT scans and bone scans were evaluated at 3 month intervals. As demonstrated in FIG. 6, one patient experienced an unconfirmed partial response, with >30% decrease in measurable disease at 3 months, but with increase in measurable lesions after treatment discontinuation by 6 months. Another individual had a decrease in measurable lesions not meeting criteria for partial response at 6 months. These individuals were the individuals with the greatest serum PSA and PAP declines demonstrated in FIG. 5, and also the individuals with the persistent PAP-specific IFNγ-secreting immunity shown in FIG. 4. A third individual in Arm 1 had a decrease in the size of a peri-rectal mass, identified as prostate cancer metastasis by biopsy pre-treatment, and which could not be identified on post-treatment biopsy.

Discussion:

Immune based therapies have demonstrated remarkable clinical effects in the last several years, leading Science to name cancer immunotherapy as the scientific breakthrough of the year for 2013[78]. A great part of this success has been due to T cell checkpoint inhibitors, including antibodies targeting PD-1/PD-L1 or CTLA-4, that have demonstrated efficacy for several cancer types. Notwithstanding, previous evaluation of these T cell checkpoint inhibitors as monotherapies in advanced prostate cancer has demonstrated little benefit[79,21,22]. A possible exception may be advanced tumors with defects in DNA repair genes or rare subtypes of "inflamed" prostate tumors that have higher numbers of infiltrating T cells and/or PD-L1 expression on tumor cells[80]. Conversely, T-cell activating therapies such as vaccines have demonstrated clinical effects, and in fact the only FDA approved anti-tumor vaccine is one targeting a prostate cancer antigen, PAP, for men with advanced, castration-resistant metastatic prostate cancer. The current trial, sought to determine if combining anti-tumor vaccination with PD-1 blockade might be synergistic in terms of eliciting anti-tumor immunity. This was based on preclinical studies demonstrating that the anti-tumor efficacy of DNA vaccines, in particular, could be increased with T-cell checkpoint blockade[81,82], and that PD-1 regulated T cell responses occurred in patients previously treated with a DNA vaccine encoding PAP[83]. To our knowledge, this is the first report of a clinical trial using an anti-tumor vaccine in combination with PD-1 blockade. Our results demonstrate that this approach can yield objective tumor responses, an elusive endpoint for anti-tumor vaccines in advanced prostate cancers to date, and thus could potentially be explored for other tumor types that have demonstrated little effect from PD-1 blockade alone.

The current trial was constructed to determine if there might be a preference for concurrent or sequential treatment with PD-1 blockade. That is, it has been demonstrated that PD-1 expression occurs with T cell activation, and hence it might be advantageous to block PD-1 at the time of initial T-cell activation with vaccination[84]. On the other hand, PD-L1 expression on tumors likely occurs in response to IFNγ in the tumor microenvironment, and thus may be increased by antigen-specific CD8+ T cells expressing IFNγ in response to immunization. In fact, we have previously demonstrated in mice that PD-L1 expression increases on tumors following immunization, and similarly that PD-L1 expression increases on circulating prostate cancer cells shortly after vaccination in patients with prostate cancer who developed PAP-specific IFNγ-secreting T cells, but declines over time[18,20]. Consequently, it was conceivable that it may be preferable to first elicit those cells with vaccination prior to PD-1 blockade. While preliminary, as this trial remains underway and the number of patients per arm at present is too small for definitive conclusions, our results suggest that there may be a preference for concurrent treatment, suggesting that PD-1 blockade at the time of T-cell activation is critical to elicit cells with anti-tumor efficacy that can mediate their effect prior to PD-L1 ligation in the tumor microenvironment.

Of note, objective responses and PSA declines were observed in the same individuals who also developed IFNγ-secreting PAP-specific immune responses. This suggests that the mechanism of anti-tumor response was specifically related to the vaccination, and not, for example due to defects in DNA repair as have been previously associated with response to PD-1 blockade[80]. Certainly, this will be explored in greater detail as this trial continues, but such defects are rare in prostate cancer. Moreover, the pattern of response and subsequent increase in tumor growth after the period of treatment ended as we observed is less consistent with the dramatic declines and stable regression as has been observed in individuals with DNA repair defects treated with pembrolizumab[80,85]. Rather, our findings are more consistent with a treatment effect from the concurrent treatment that stopped after 12 weeks when the treatment ended. As a result, unfortunately objective radiographic responses could not be confirmed after treatment was discontinued. Consequently, as a future direction, we plan to consider prolonged periods of treatment to treat to maximum effect rather than arbitrarily stop after 12 weeks of treatment.

REFERENCES

1. Siegel, R., Ma, J., Zou, Z. and Jemal, A. (2014). "Cancer statistics, 2014." *CA Cancer J Clin* 64: 9-29.
2. Oefelein, M. G., Smith, N. D., Grayhack, J. T., Schaeffer, A. J. and McVary, K. T. (1997). "Long-term results of radical retropubic prostatectomy in men with high grade carcinoma of the prostate." *J Urol* 158: 1460-5.
3. Crawford, E. D., Eisenberger, M. A., McLeod, D. G., Spaulding, J. T., Benson, R., Dorr, F. A., Blumenstein, B. A., Davis, M. A. and Goodman, P. J. (1989). "A controlled trial of leuprolide with and without flutamide in prostatic carcinoma." *N Engl J Med* 321: 419-24.
4. Tannock, I. F., de Wit, R., Berry, W. R., Horti, J., Pluzanska, A., Chi, K. N., Oudard, S., Theodore, C., James, N. D., Turesson, I., Rosenthal, M. A. and Eisenberger, M. A. (2004). "Docetaxel plus prednisone or mitoxantrone plus prednisone for advanced prostate cancer." *N Engl J Med* 351: 1502-12.
5. Petrylak, D. P., Tangen, C., Hussain, M., Lara, P. and al., e. (2004). "SWOG 99-16: Randomized phase III trial of docetaxel (D)/estramustine (E) versus mitoxantrone (M)/prednisone (p) in men with androgen-independent prostate cancer (AIPCA) (abstract #3)." *Proc Am Soc Clin Oncol* 22.
6. de Bono, J. S., Oudard, S., Ozguroglu, M., Hansen, S., Machiels, J. P., Kocak, I., Gravis, G., Bodrogi, I., Mackenzie, M. J., Shen, L., Roessner, M., Gupta, S. and Sartor, A. O. (2010). "Prednisone plus cabazitaxel or mitoxantrone for metastatic castration-resistant prostate cancer progressing after docetaxel treatment: a randomised open-label trial." *Lancet* 376: 1147-54.
7. Kantoff, P. W., Higano, C. S., Shore, N. D., Berger, E. R., Small, E. J., Penson, D. F., Redfern, C. H., Ferrari, A. C., Dreicer, R., Sims, R. B., Xu, Y., Frohlich, M. W. and Schellhammer, P. F. (2010). "Sipuleucel-T immunotherapy for castration-resistant prostate cancer." *N Engl J Med* 363: 411-22.
8. Scher, H. I., Fizazi, K., Saad, F., Taplin, M. E., Sternberg, C. N., Miller, K., de Wit, R., Mulders, P., Chi, K. N., Shore, N. D., Armstrong, A. J., Flaig, T. W., Flechon, A., Mainwaring, P., Fleming, M., Hainsworth, J. D., Hirmand, M., Selby, B., Seely, L., de Bono, J. S. and Investigators, A. (2012). "Increased survival with enzalutamide in prostate cancer after chemotherapy." *N Engl J Med* 367: 1187-97.
9. de Bono, J. S., Logothetis, C. J., Molina, A., Fizazi, K., North, S., Chu, L., Chi, K. N., Jones, R. J., Goodman, O. B., Jr., Saad, F., Staffurth, J. N., Mainwaring, P., Harland, S., Flaig, T. W., Hutson, T. E., Cheng, T., Patterson, H., Hainsworth, J. D., Ryan, C. J., Sternberg, C. N., Ellard, S. L., Flechon, A., Saleh, M., Scholz, M., Efstathiou, E., Zivi, A., Bianchini, D., Loriot, Y., Chieffo, N., Kheoh, T., Haqq, C. M. and Scher, H. I. (2011). "Abiraterone and increased survival in metastatic prostate cancer." *N Engl J Med* 364: 1995-2005.

10. Kirk, T. N. and Moyad, M. A. (2006). "National survey of advanced prostate cancer patients reveals disparity between perceptions and reality of treatment." *Proc. Amer. Soc. Clin. Oncol.* 24: 490s, abstract #8590.
11. McNeel, D. G. (2007). "Prostate cancer immunotherapy." *Curr Opin Urol* 17: 175-81.
12. McNeel, D. G. (2007). "Cellular immunotherapies for prostate cancer." *Biomed Pharmacother* 61: 315-22.
13. Ward, J. E. and McNeel, D. G. (2007). "GVAX: an allogeneic, whole-cell, GM-CSF-secreting cellular immunotherapy for the treatment of prostate cancer." *Expert Opin Biol Ther* 7: 1893-902.
14. Alam, S. and McNeel, D. G. (2010). "DNA vaccines for the treatment of prostate cancer." *Expert Rev Vaccines* 9: 731-45.
15. Wolchok, J. D., Kluger, H., Callahan, M. K., Postow, M. A., Rizvi, N. A., Lesokhin, A. M., Segal, N. H., Ariyan, C. E., Gordon, R. A., Reed, K., Burke, M. M., Caldwell, A., Kronenberg, S. A., Agunwamba, B. U., Zhang, X., Lowy, I., Inzunza, H. D., Feely, W., Horak, C. E., Hong, Q., Korman, A. J., Wigginton, J. M., Gupta, A. and Sznol, M. (2013). "Nivolumab plus ipilimumab in advanced melanoma." *N Engl J Med* 369: 122-33.
16. Hamid, O., Robert, C., Daud, A., Hodi, F. S., Hwu, W. J., Kefford, R., Wolchok, J. D., Hersey, P., Joseph, R. W., Weber, J. S., Dronca, R., Gangadhar, T. C., Patnaik, A., Zarour, H., Joshua, A. M., Gergich, K., Elassaiss-Schaap, J., Algazi, A., Mateus, C., Boasberg, P., Tumeh, P. C., Chmielowski, B., Ebbinghaus, S. W., Li, X. N., Kang, S. P. and Ribas, A. (2013). "Safety and tumor responses with lambrolizumab (anti-PD-1) in melanoma." *N Engl J Med* 369: 134-44.
17. Hodi, F. S., O'Day, S. J., McDermott, D. F., Weber, R. W., Sosman, J. A., Haanen, J. B., Gonzalez, R., Robert, C., Schadendorf, D., Hassel, J. C., Akerley, W., van den Eertwegh, A. J., Lutzky, J., Lorigan, P., Vaubel, J. M., Linette, G. P., Hogg, D., Ottensmeier, C. H., Lebbe, C., Peschel, C., Quirt, I., Clark, J. I., Wolchok, J. D., Weber, J. S., Tian, J., Yellin, M. J., Nichol, G. M., Hoos, A. and Urba, W. J. (2010). "Improved Survival with Ipilimumab in Patients with Metastatic Melanoma." *N Engl J Med* 363: 711-23.
18. Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., Leming, P. D., Spigel, D. R., Antonia, S. J., Horn, L., Drake, C. G., Pardoll, D. M., Chen, L., Sharfman, W. H., Anders, R. A., Taube, J. M., McMiller, T. L., Xu, H., Korman, A. J., Jure-Kunkel, M., Agrawal, S., McDonald, D., Kollia, G. D., Gupta, A., Wigginton, J. M. and Sznol, M. (2012). "Safety, activity, and immune correlates of anti-PD-1 antibody in cancer." *N Engl J Med* 366: 2443-54.
19. Brahmer, J. R., Drake, C. G., Wollner, I., Powderly, J. D., Picus, J., Sharfman, W. H., Stankevich, E., Pons, A., Salay, T. M., McMiller, T. L., Gilson, M. M., Wang, C., Selby, M., Taube, J. M., Anders, R., Chen, L., Korman, A. J., Pardoll, D. M., Lowy, I. and Topalian, S. L. (2010). "Phase I study of single-agent anti-programmed death-1 (MDX-1106) in refractory solid tumors: safety, clinical activity, pharmacodynamics, and immunologic correlates." *J Clin Oncol* 28: 3167-75.
20. Sfanos, K. S., Bruno, T. C., Meeker, A. K., De Marzo, A. M., Isaacs, W. B. and Drake, C. G. (2009). "Human prostate-infiltrating CD8+ T lymphocytes are oligoclonal and PD-1+." *Prostate* 69: 1694-703.
21. Olson, B. M. and McNeel, D. G. (2011). "Sipuleucel-T: immunotherapy for advanced prostate cancer." *Open Acc. J. Urol.* 3: 49-60.
22. Gutman, A. B. and Gutman, E. B. (1938). "An acid phosphatase in the serum of patients with metastasizing carcinoma of the prostate gland." *J. Clin. Invest.* 17: 473-9.
23. Terracio, L., Rule, A., Salvato, J. and Douglas, W. H. (1985). "Immunofluorescent localization of an androgen-dependent isoenzyme of prostatic acid phosphatase in rat ventral prostate." *Anat Rec* 213: 131-9.
24. Fong, L., Ruegg, C. L., Brockstedt, D., Engleman, E. G. and Laus, R. (1997). "Induction of tissue-specific autoimmune prostatitis with prostatic acid phosphatase immunization; implications for immunotherapy of prostate cancer." *J. Immunol.* 159: 3113-7.
25. Johnson, L. E., Frye, T. P., Arnot, A. R., Marquette, C., Couture, L. A., Gendron-Fitzpatrick, A. and McNeel, D. G. (2006). "Safety and immunological efficacy of a prostate cancer plasmid DNA vaccine encoding prostatic acid phosphatase (PAP)." *Vaccine* 24: 293-303.
26. Johnson, L. E., Frye, T. P., Chinnasamy, N., Chinnasamy, D. and McNeel, D. G. (2007). "Plasmid DNA vaccine encoding prostatic acid phosphatase is effective in eliciting autologous antigen-specific CD8+ T cells." *Cancer Immunol Immunother* 56: 885-95.
27. Laus, R., Yang, D. M., Ruegg, C. L., Shapero, M. H., Slagle, P. H., Small, E., Burch, P. and Valone, F. H. (2001). "Dendritic cell immunotherapy of prostate cancer: preclinical models and early clinical experience." *Canc Res Ther Control* 11: 1-10.
28. Fong, L., Brockstedt, D., Benike, C., Breen, J. K., Strang, G., Ruegg, C. L. and Engleman, E. G. (2001). "Dendritic Cell-Based Xenoantigen Vaccination for Prostate Cancer Immunotherapy." *J Immunol* 167: 7150-6.
29. McNeel, D. G., Dunphy, E. J., Davies, J. G., Frye, T. P., Johnson, L. E., Staab, M. J., Horvath, D. L., Straus, J., Alberti, D., Marnocha, R., Liu, G., Eickhoff, J. C. and Wilding, G. (2009). "Safety and immunological efficacy of a DNA vaccine encoding prostatic acid phosphatase in patients with stage D0 prostate cancer." *J Clin Oncol* 27: 4047-54.
30. Becker, J. T., Olson, B. M., Johnson, L. E., Davies, J. G., Dunphy, E. J. and McNeel, D. G. (2010). "DNA vaccine encoding prostatic acid phosphatase (PAP) elicits long-term T-cell responses in patients with recurrent prostate cancer." *J Immunother* 33: 639-47.
31. McNeel, D. G., Becker, J. T., Eickhoff, J. C., Johnson, L. E., Bradley, E., Pohlkamp, I., Staab, M. J., Liu, G., Wilding, G. and Olson, B. M. (2014). "Real-time immune monitoring to guide plasmid DNA vaccination schedule targeting prostatic acid phosphatase in patients with castration-resistant prostate cancer." *Clin Cancer Res* 20: 3692-704.
32. Griffiths, J. (1980). "Prostate-specific acid phosphatase: re-evaluation of radioimmunoassay in diagnosing prostatic disease." *Clin. Chem.* 26: 433-6.
33. Jobsis, A. C., De Vries, G. P., Anholt, R. R. and Sanders, G. T. (1978). "Demonstration of the prostatic origin of metastases: an immunohistochemical method for formalin-fixed embedded tissue." *Cancer* 41: 1788-93.
34. McNeel, D. G., Nguyen, L. D., Storer, B. E., Vessella, R., Lange, P. H. and Disis, M. L. (2000). "Antibody immunity to prostate cancer-associated antigens can be detected in the serum of patients with prostate cancer." *J. Urol.* 164: 1825-9.

35. McNeel, D. G., Nguyen, L. D., Ellis, W. J., Higano, C. S., Lange, P. H. and Disis, M. L. (2001). "Naturally occurring prostate cancer antigen-specific T cell responses of a Th1 phenotype can be detected in patients with prostate cancer." *Prostate* 47: 222-9.

36. Olson, B. M., Frye, T. P., Johnson, L. E., Fong, L., Knutson, K. L., Disis, M. L. and McNeel, D. G. (2010). "HLA-A2-restricted T-cell epitopes specific for prostatic acid phosphatase." *Cancer Immunol Immunother* 59: 943-53.

37. Robert, C., Ribas, A., Wolchok, J. D., Hodi, F. S., Hamid, O., Kefford, R., Weber, J. S., Joshua, A. M., Hwu, W. J., Gangadhar, T. C., Patnaik, A., Dronca, R., Zarour, H., Joseph, R. W., Boasberg, P., Chmielowski, B., Mateus, C., Postow, M. A., Gergich, K., Elassaiss-Schaap, J., Li, X. N., Iannone, R., Ebbinghaus, S. W., Kang, S. P. and Daud, A. (2014). "Anti-programmed-death-receptor-1 treatment with pembrolizumab in ipilimumab-refractory advanced melanoma: a randomised dose-comparison cohort of a phase 1 trial." *Lancet* 384: 1109-17.

38. Iwasaki, A., Torres, C. A., Ohashi, P. S., Robinson, H. L. and Barber, B. H. (1997). "The dominant role of bone marrow-derived cells in CTL induction following plasmid DNA immunization at different sites." *J Immunol* 159: 11-4.

39. La Cava, A., Billetta, R., Gaietta, G., Bonnin, D. B., Baird, S. M. and Albani, S. (2000). "Cell-mediated DNA transport between distant inflammatory sites following intradermal DNA immunization in the presence of adjuvant." *J Immunol* 164: 1340-5.

40. Corr, M., von Damm, A., Lee, D. J. and Tighe, H. (1999). "In vivo priming by DNA injection occurs predominantly by antigen transfer." *J Immunol* 163: 4721-7.

41. Irvine, K. R. and Restifo, N. P. (1995). "The next wave of recombinant and synthetic anticancer vaccines." *Seminars in Canc Biol* 6: 337-47.

42. Raz, E., Tighe, H., Sato, Y., Corr, M., Dudler, J. A., Roman, M., Swain, S. L., Spiegelberg, H. L. and Carson, D. A. (1996). "Preferential induction of a Th1 immune response and inhibition of specific IgE antibody formation by plasmid DNA immunization." *Proc Natl Acad Sci USA* 93: 5141-5.

43. Chen, Y., Webster, R. G. and Woodland, D. L. (1998). "Induction of CD8+ T cell responses to dominant and subdominant epitopes and protective immunity to Sendai virus infection by DNA vaccination." *J Immunol.* 160: 2425-32.

44. Thomson, S. A., Sherritt, M. A., Medveczky, J., Elliott, S. L., Moss, D. J., Fernando, G. J., Brown, L. E. and Suhrbier, A. (1998). "Delivery of multiple CD8 cytotoxic T cell epitopes by DNA vaccination." *J. Immunol* 160: 1717-23.

45. Cho, H. J., Takabayashi, K., Cheng, P. M., Nguyen, M. D., Corr, M., Tuck, S. and Raz, E. (2000). "Immunostimulatory DNA-based vaccines induce cytotoxic lymphocyte activity by a T-helper cell-independent mechanism." *Nat Biotechnol* 18: 509-14.

46. Corr, M., Lee, D. J., Carson, D. A. and Tighe, H. (1996). "Gene vaccination with naked plasmid DNA: mechanism of CTL priming." *J Exp Med* 184: 1555-60.

47. Svanholm, C., Bandholtz, L., Lobell, A. and Wigzell, H. (1999). "Enhancement of antibody responses by DNA immunization using expression vectors mediating efficient antigen secretion." *J Immunol Methods* 228: 121-30.

48. Rahman, F., Dahmen, A., Herzog-Hauff, S., Bocher, W. O., Galle, P. R. and Lohr, H. F. (2000). "Cellular and humoral immune responses induced by intradermal or intramuscular vaccination with the major hepatitis B surface antigen." *Hepatology* 31: 521-7.

49. (2010). "USDA licenses DNA vaccine for treatment of melanoma in dogs." *J Am Vet Med Assoc* 236: 495.

50. Bergman, P. J., McKnight, J., Novosad, A., Charney, S., Farrelly, J., Craft, D., Wulderk, M., Jeffers, Y., Sadelain, M., Hohenhaus, A. E., Segal, N., Gregor, P., Engelhorn, M., Riviere, I., Houghton, A. N. and Wolchok, J. D. (2003). "Long-term survival of dogs with advanced malignant melanoma after DNA vaccination with xenogeneic human tyrosinase: a phase I trial." *Clin Cancer Res* 9: 1284-90.

51. Zlotocha, S., Staab, M. J., Horvath, D., Straus, J., Dobratz, J., Oliver, K., Wasielewski, S., Alberti, D., Liu, G., Wilding, G., Eickhoff, J. and McNeel, D. G. (2005). "A phase I study of a DNA vaccine targeting prostatic acid phosphatase in patients with stage D0 prostate cancer." *Clin Genitourin Cancer* 4: 215-8.

52. Smith, H. A. and McNeel, D. G. (2011). "Vaccines targeting the cancer-testis antigen SSX-2 elicit HLA-A2 epitope-specific cytolytic T cells." *J Immunother* 34: 569-80.

53. Pajot, A., Michel, M. L., Fazilleau, N., Pancre, V., Auriault, C., Ojcius, D. M., Lemonnier, F. A. and Lone, Y. C. (2004). "A mouse model of human adaptive immune functions: HLA-A2.1-/HLA-DR1-transgenic H-2 class I-/class II-knockout mice." *Eur J Immunol* 34: 3060-9.

54. Olson, B. M. and McNeel, D. G. (2007). "Identification of HLA-A2-restricted cytotoxic T lymphocytes specific for the androgen receptor ligand binding domain in patients with prostate cancer." *Proc. Amer. Assn. Cancer Res.* 48: 5105.

55. Smith, H. A., Rekoske, B. T. and McNeel, D. G. (2014). "DNA vaccines encoding altered peptide ligands for SSX2 enhance epitope-specific CD8+ T-cell immune responses." *Vaccine* 32: 1707-15.

56. Olson, B. M., Jankowska-Gan, E., Becker, J. T., Vignali, D. A., Burlingham, W. J. and McNeel, D. G. (2012). "Human Prostate Tumor Antigen-Specific CD8+ Regulatory T Cells Are Inhibited by CTLA-4 or IL-35 Blockade." *J Immunol* 189: 5590-601.

57. Kantoff, P. W., Schuetz, T. J., Blumenstein, B. A., Glode, L. M., Bilhartz, D. L., Wyand, M., Manson, K., Panicali, D. L., Laus, R., Schlom, J., Dahut, W. L., Arlen, P. M., Gulley, J. L. and Godfrey, W. R. (2010). "Overall survival analysis of a phase II randomized controlled trial of a Poxviral-based PSA-targeted immunotherapy in metastatic castration-resistant prostate cancer." *J Clin Oncol* 28: 1099-105.

58. Disis, M. L., Bernhard, H., Shiota, F. M., Hand, S. L., Gralow, J. R., Huseby, E. S., Gillis, S. and Cheever, M. A. (1996). "Granulocyte-macrophage colony-stimulating factor: an effective adjuvant for protein and peptide-based vaccines." *Blood* 88: 202-10.

59. Disis, M. L., Grabstein, K. H., Sleath, P. R. and Cheever, M. A. (1999). "Generation of immunity to the HER-2/neu oncogenic protein in patients with breast and ovarian cancer using a peptide-based vaccine." *Clin. Cancer Res.* 5: 1289-97.

60. Bernhard, H., Disis, M. L., Heimfeld, S., Hand, S., Gralow, J. R. and Cheever, M. A. (1995). "Generation of immunostimulatory dendritic cells from human CD34+ hematopoietic progenitor cells of the bone marrow and peripheral blood." *Cancer Res.* 55: 1099-104.

61. Tarr, P. E., Lin, R., Mueller, E. A., Kovarik, J. M., Guillaume, M. and Jones, T. C. (1996). "Evaluation of tolerability and antibody response after recombinant human granulocyte-macrophage colony-stimulating factor (rhGM-CSF) and a single dose of recombinant hepatitis B vaccine." *Vaccine* 14: 1199-204.
62. McNeel, D. G., Schiffman, K. and Disis, M. L. (1999). "Immunization with recombinant human granulocyte-macrophage colony-stimulating factor as a vaccine adjuvant elicits both a cellular and humoral response to recombinant human granulocyte-macrophage colony-stimulating factor." *Blood* 93: 2653-9.
63. Devereux, S., Bull, H. A., Campos-Costa, D., Saib, R. and Linch, D. C. (1989). "Granulocyte macrophage colony stimulating factor induced changes in cellular adhesion molecule expression and adhesion to endothelium: in-vitro and in-vivo studies in man." *Br J Haematol* 71: 323-30.
64. Scher, H. I., Halabi, S., Tannock, I., Morris, M., Sternberg, C. N., Carducci, M. A., Eisenberger, M. A., Higano, C., Bubley, G. J., Dreicer, R., Petrylak, D., Kantoff, P., Basch, E., Kelly, W. K., Figg, W. D., Small, E. J., Beer, T. M., Wilding, G., Martin, A. and Hussain, M. (2008). "Design and end points of clinical trials for patients with progressive prostate cancer and castrate levels of testosterone: recommendations of the Prostate Cancer Clinical Trials Working Group." *J Clin Oncol* 26: 1148-59.
65. VanBuskirk, A. M., Burlingham, W. J., Jankowska-Gan, E., Chin, T., Kusaka, S., Geissler, F., Pelletier, R. P. and Orosz, C. G. (2000). "Human allograft acceptance is associated with immune regulation." *J Clin Invest* 106: 145-55.
66. Derks, R. A., Jankowska-Gan, E., Xu, Q. and Burlingham, W. J. (2007). "Dendritic cell type determines the mechanism of bystander suppression by adaptive T regulatory cells specific for the minor antigen HA-1." *J Immunol* 179: 3443-51.
67. Smith, H. A., Maricque, B. B., Eberhardt, J., Petersen, B., Gulley, J. L., Schlom, J. and McNeel, D. G. (2011). "IgG responses to tissue-associated antigens as biomarkers of immunological treatment efficacy." *J Biomed Biotech* 2011:454861.
68. Fong, L., Kwek, S. S., O'Brien, S., Kavanagh, B., McNeel, D. G., Weinberg, V., Lin, A. M., Rosenberg, J., Ryan, C. J., Rini, B. I. and Small, E. J. (2009). "Potentiating endogenous antitumor immunity to prostate cancer through combination immunotherapy with CTLA4 blockade and GM-CSF." *Cancer Res* 69: 609-15.
69. Zabransky, D. J., Smith, H. A., Thoburn, C. J., Zahurak, M., Keizman, D., Carducci, M., Eisenberger, M. A., McNeel, D. G., Drake, C. G. and Antonarakis, E. S. (2011). "Lenalidomide modulates IL-8 and anti-prostate antibody levels in men with biochemically recurrent prostate cancer." *Prostate*: (in press).
70. Dubovsky, J. A., Albertini, M. R. and McNeel, D. G. (2007). "MAD-CT-2 identified as a novel melanoma cancer-testis antigen using phage immunoblot analysis." *J Immunother* 30: 675-83.
71. Hoeppner, L. H., Dubovsky, J. A., Dunphy, E. J. and McNeel, D. G. (2006). "Humoral immune responses to testis antigens in sera from patients with prostate cancer." *Cancer Immun* 6: 1-7.
72. Dunphy, E. J., Eickhoff, J. C., Muller, C. H., Berger, R. E. and McNeel, D. G. (2004). "Identification of antigen-specific IgG in sera from patients with chronic prostatitis." *J. Clin. Immunol.* 24: 492-501.
73. Dunphy, E. J. and McNeel, D. G. (2005). "Antigen-specific IgG elicited in subjects with prostate cancer treated with flt3 ligand." *J Immunother* 28: 268-75.
74. Mooney, C. J., Dunphy, E. J., Stone, B. and McNeel, D. G. (2006). "Identification of autoantibodies elicited in a patient with prostate cancer presenting as dermatomyositis." *Int J Urol* 13: 211-7.
75. Morse, M. D. and McNeel, D. G. (2010). "Prostate Cancer Patients Treated with Androgen Deprivation Therapy Develop Persistent Changes in Adaptive Immune Responses." *Hum Immunol* 71: 496-504.
76. Maricque, B. B., Eickhoff, J. C. and McNeel, D. G. (2011). "Antibody responses to prostate-associated antigens in patients with prostatitis and prostate cancer." *Prostate* 71: 134-46.
77. Martin, T., Parker, S. E., Hedstrom, R., Le, T., Hoffman, S. L., Norman, J., Hobart, P. and Lew, D. (1999). "Plasmid DNA malaria vaccine: the potential for genomic integration after intramuscular injection." *Hum Gene Ther* 10: 759-68.
78. Couzin-Frankel J. Breakthrough of the year 2013. Cancer immunotherapy. Science. Dec. 20, 2013; 342(6165): 1432-1433.
79. Beer T M, Kwon E D, Drake C G, et al. Randomized, Double-Blind, Phase III Trial of Ipilimumab Versus Placebo in Asymptomatic or Minimally Symptomatic Patients With Metastatic Chemotherapy-Naive Castration-Resistant Prostate Cancer. J Clin Oncol. January 2017; 35(1):40-47.
80. Graff J N, Alumkal J J, Drake C G, et al. Early evidence of anti-PD-1 activity in enzalutamide-resistant prostate cancer. Oncotarget. Aug. 16, 2016; 7(33):52810-52817.
81. Rekoske B T, Smith H A, Olson B M, Maricque B B, McNeel D G. PD-1 or PD-L1 Blockade Restores Antitumor Efficacy Following SSX2 Epitope-Modified DNA Vaccine Immunization. Cancer immunology research. August 2015; 3(8):946-955.
82. Colluru V T, Zahm C D, McNeel D G. Mini-intronic plasmid vaccination elicits tolerant LAG3+ CD8 T cells and inferior anti-tumor responses. Oncoimmunology. 2016:(in press).
83. Rekoske B T, Olson B M, McNeel D G. Antitumor vaccination of prostate cancer patients elicits PD-1/PD-L1 regulated antigen-specific immune responses. Oncoimmunology. June 2016; 5(6):e1165377.
84. Oestreich K J, Yoon H, Ahmed R, Boss J M. NFATc1 regulates PD-1 expression upon T cell activation. J Immunol. Oct. 1, 2008; 181(7):4832-4839.
85. Le D T, Uram J N, Wang H, et al. PD-1 Blockade in Tumors with Mismatch-Repair Deficiency. N Engl J Med. Jun. 25, 2015; 372(26):2509-2520.

All publications and patents mentioned in the above specification (including, but not limited to those cited in the above section) are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for treating prostate cancer in a subject, the method comprising:
   (a) administering to a subject a pTVG-HP DNA vaccine; and
   (b) administering to the subject a human programmed death receptor-1 (PD-1) inhibitor selected from the group consisting of pembrolizumab and nivolumab, wherein the vaccine and the PD-1 inhibitor are first administered concurrently and wherein after the first concurrent administration of the vaccine and the PD-1 inhibitor, the vaccine is administered every 14 days and the PD-1 inhibitor is administered every 28 days.

2. The method of claim 1, wherein the nucleic acid further comprises a transcriptional regulatory element and/or an immunostimulatory sequence.

3. The method of claim 1, wherein the subject is a human.

4. The method of claim 1, wherein the vaccine and the PD-1 inhibitor are administered a plurality of times, and wherein after the first concurrent administration of the vaccine and the PD-1 inhibitor, the vaccine is administered every 14 days and the PD-1 inhibitor is administered every 28 days for a period of up to 90 days.

5. The method of claim 4, further comprising administering the vaccine every 10 to 21 days and the PD-1 inhibitor every 17 to 28 days for a period of from 91 days to 365 days.

6. The method of claim 5, wherein patients that exhibit a decrease in PSA or tumor regression after 90 days are selected for the administration of the vaccine every 10 to 21 days and the PD-1 inhibitor every 17 to 28 days for a period of from 91 days to 365 days.

7. The method of claim 5, further comprising administering the vaccine every 10 to 21 days and the PD-1 inhibitor every 17 to 28 days for a period of from 366 days to 730 days.

8. The method of claim 7, wherein patients that exhibit a decrease in PSA or tumor regression after 365 days are selected for the administration of the vaccine every 10 to 21 days and the PD-1 inhibitor every 17 to 28 days for a period of from 91 days to 365 days.

9. The method of claim 1, wherein the method increases the number of PAP-specific T cells.

10. The method of claim 1, wherein the method decreases the amount of circulating tumor cells in the subject's blood.

11. A method for treating prostate cancer in a subject, the method comprising:
    (a) administering to a subject a vaccine comprising a nucleic acid comprising a nucleotide sequence from a prostatic acid phosphatase (PAP) gene, wherein the nucleotide sequence encodes a polypeptide comprising the amino acid sequence at least 95% identical to an amino acid sequence selected from the group consisting of SEQ ID NO: 1, SEQ ID NO: 2, and SEQ ID NO: 3; and
    (b) administering to the subject a human programmed death receptor-1 (PD-1) inhibitor selected from the group consisting of pembrolizumab and nivolumab, wherein the vaccine is administered every 14 days and the PD-1 inhibitor is administered every 28 days after the first administration of said vaccine and said PD-1 inhibitor.

12. The method of claim 11, wherein said vaccine and said PD-1 inhibitor are administered within 48 hours of one another at the beginning of the overlapping schedule.

13. The method of claim 11, wherein after the first administration of the vaccine and the PD-1 inhibitor, the vaccine is administered every 14 days and the PD-1 inhibitor is administered every 28 days for a period of up to 90 days.

14. The method of claim 13, further comprising administering the vaccine every 10 to 21 days and the PD-1 inhibitor every 17 to 28 days for a period of from 91 days to 365 days.

15. The method of claim 14, wherein patients that exhibit a decrease in PSA or tumor regression after 90 days are selected for the administration of the vaccine every 10 to 21 days and the PD-1 inhibitor every 17 to 28 days for a period of from 91 days to 365 days.

16. The method of claim 14, further comprising administering the vaccine every 10 to 20 days and the PD-1 inhibitor every 17 to 28 days for a period of from 366 days to 730 days.

* * * * *

SEQUENCE LISTING

<160> NUMBER OF SEQ ID NOS: 4

<210> SEQ ID NO 1
<211> LENGTH: 386
<212> TYPE: PRT
<213> ORGANISM: homo sapiens

<400> SEQUENCE: 1

```
Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365
```

Ser Thr Glu Cys Met Thr Thr Asn Ser His Gln Gly Thr Glu Asp Ser
370                 375                 380

Thr Asp
385

<210> SEQ ID NO 2
<211> LENGTH: 381
<212> TYPE: PRT
<213> ORGANISM: homo sapiens

<400> SEQUENCE: 2

Met Arg Ala Val Pro Leu Pro Leu Ser Arg Thr Ala Ser Leu Ser Leu
1               5                   10                  15

Gly Phe Leu Leu Leu Leu Ser Leu Cys Leu Asp Pro Gly Gln Ala Lys
            20                  25                  30

Glu Leu Lys Phe Val Thr Leu Val Phe Arg His Gly Asp Arg Gly Pro
        35                  40                  45

Ile Glu Thr Phe Pro Thr Asp Pro Ile Thr Glu Ser Ser Trp Pro Gln
    50                  55                  60

Gly Phe Gly Gln Leu Thr Gln Trp Gly Met Glu Gln His Tyr Glu Leu
65                  70                  75                  80

Gly Ser Tyr Ile Arg Lys Arg Tyr Gly Arg Phe Leu Asn Asp Thr Tyr
                85                  90                  95

Lys His Asp Gln Ile Tyr Ile Arg Ser Thr Asp Val Asp Arg Thr Leu
            100                 105                 110

Met Ser Ala Met Thr Asn Leu Ala Ala Leu Phe Pro Pro Glu Gly Ile
        115                 120                 125

Ser Ile Trp Asn Pro Arg Leu Leu Trp Gln Pro Ile Pro Val His Thr
    130                 135                 140

Val Ser Leu Ser Glu Asp Arg Leu Leu Tyr Leu Pro Phe Arg Asp Cys
145                 150                 155                 160

Pro Arg Phe Glu Glu Leu Lys Ser Glu Thr Leu Glu Ser Glu Glu Phe
                165                 170                 175

Leu Lys Arg Leu His Pro Tyr Lys Ser Phe Leu Asp Thr Leu Ser Ser
            180                 185                 190

Leu Ser Gly Phe Asp Asp Gln Asp Leu Phe Gly Ile Trp Ser Lys Val
        195                 200                 205

Tyr Asp Pro Leu Phe Cys Glu Ser Val His Asn Phe Thr Leu Pro Ser
    210                 215                 220

Trp Ala Thr Glu Asp Ala Met Ile Lys Leu Lys Glu Leu Ser Glu Leu
225                 230                 235                 240

Ser Leu Leu Ser Leu Tyr Gly Ile His Lys Gln Lys Glu Lys Ser Arg
                245                 250                 255

Leu Gln Gly Gly Val Leu Val Asn Glu Ile Leu Lys Asn Met Lys Leu
            260                 265                 270

Ala Thr Gln Pro Gln Lys Tyr Lys Lys Leu Val Met Tyr Ser Ala His
        275                 280                 285

Asp Thr Thr Val Ser Gly Leu Gln Met Ala Leu Asp Val Tyr Asn Gly
    290                 295                 300

Val Leu Pro Pro Tyr Ala Ser Cys His Met Met Glu Leu Tyr His Asp
305                 310                 315                 320

Lys Gly Gly His Phe Val Glu Met Tyr Tyr Arg Asn Glu Thr Gln Asn
                325                 330                 335

Glu Pro Tyr Pro Leu Thr Leu Pro Gly Cys Thr His Ser Cys Pro Leu
            340                 345                 350

```
Glu Lys Phe Ala Glu Leu Leu Asp Pro Val Ile Ser Gln Asp Trp Ala
            355                 360                 365

Thr Glu Cys Met Ala Thr Ser Ser His Gln Gly Arg Asn
    370                 375                 380

<210> SEQ ID NO 3
<211> LENGTH: 381
<212> TYPE: PRT
<213> ORGANISM: homo sapiens

<400> SEQUENCE: 3

Met Arg Ala Val Pro Leu His Leu Val Gly Thr Ala Ser Leu Thr Leu
1               5                   10                  15

Gly Phe Leu Leu Leu Ser Leu Arg Leu Asp Pro Gly Gln Ala Lys
            20                  25                  30

Glu Leu Lys Phe Val Thr Leu Val Phe Arg His Gly Asp Arg Gly Pro
            35                  40                  45

Ile Glu Thr Phe Pro Asn Asp Pro Ile Lys Glu Ser Ser Trp Pro Gln
    50                  55                  60

Gly Phe Gly Gln Leu Thr Lys Trp Gly Met Gly Gln His Tyr Glu Leu
65                  70                  75                  80

Gly Ser Tyr Ile Arg Arg Arg Tyr Gly Arg Phe Leu Asn Asn Ser Tyr
                85                  90                  95

Lys His Asp Gln Val Tyr Ile Arg Ser Thr Asp Val Asp Arg Thr Leu
            100                 105                 110

Met Ser Ala Met Thr Asn Leu Ala Ala Leu Phe Pro Pro Glu Gly Ile
            115                 120                 125

Ser Ile Trp Asn Pro Arg Leu Leu Trp Gln Pro Ile Pro Val His Thr
    130                 135                 140

Val Ser Leu Ser Glu Asp Arg Leu Leu Tyr Leu Pro Phe Arg Asp Cys
145                 150                 155                 160

Pro Arg Phe Gln Glu Leu Lys Ser Glu Thr Leu Lys Ser Glu Glu Phe
                165                 170                 175

Leu Lys Arg Leu Gln Pro Tyr Lys Ser Phe Ile Asp Thr Leu Pro Ser
            180                 185                 190

Leu Ser Gly Phe Glu Asp Gln Asp Leu Phe Glu Ile Trp Ser Arg Leu
        195                 200                 205

Tyr Asp Pro Leu Tyr Cys Glu Ser Val His Asn Phe Thr Phe Arg Thr
    210                 215                 220

Trp Ala Thr Glu Asp Ala Met Thr Lys Leu Lys Glu Leu Ser Glu Leu
225                 230                 235                 240

Ser Leu Leu Ser Leu Tyr Gly Ile His Lys Gln Lys Glu Lys Ser Arg
                245                 250                 255

Leu Gln Gly Gly Val Leu Val Asn Glu Ile Leu Lys Asn Met Lys Leu
            260                 265                 270

Ala Thr Gln Pro Gln Lys Ala Arg Lys Leu Ile Met Tyr Ser Ala Tyr
        275                 280                 285

Asp Thr Thr Val Ser Gly Leu Gln Met Ala Leu Glu Leu Tyr Asn Gly
    290                 295                 300

Leu Leu Pro Pro Tyr Ala Ser Cys His Ile Met Glu Leu Tyr Gln Asp
305                 310                 315                 320

Asn Gly Gly Thr Phe Val Glu Met Tyr Tyr Arg Asn Glu Thr Gln Asn
                325                 330                 335

Glu Pro Tyr Pro Leu Thr Leu Pro Gly Cys Thr His Ser Cys Pro Leu
```

-continued

```
                340                 345                 350
Glu Lys Phe Ala Glu Leu Leu Asp Pro Val Ile Pro Gln Asp Trp Ala
            355                 360                 365

Thr Glu Cys Met Gly Thr Ser Asn His Gln Ala Ser Leu
    370                 375                 380

<210> SEQ ID NO 4
<211> LENGTH: 24
<212> TYPE: DNA
<213> ORGANISM: homo sapiens

<400> SEQUENCE: 4
tcgtcgtttt gtcgttttgt cgtt                                          24
```